United States Patent
Thayumanavan et al.

(10) Patent No.: US 11,746,172 B2
(45) Date of Patent: Sep. 5, 2023

(54) PROTEIN-POLYMER NANOASSEMBLIES AND INTRACELLULAR PROTEIN DELIVERY

(71) Applicant: University of Massachusetts, Boston, MA (US)

(72) Inventors: Sankaran Thayumanavan, Amherst, MA (US); Bin Liu, Hopkinton, MA (US)

(73) Assignee: University of Massachusetts, Boston, MA (US)

( * ) Notice: Subject to any disclaimer, the term of this patent is extended or adjusted under 35 U.S.C. 154(b) by 547 days.

(21) Appl. No.: 16/932,774

(22) Filed: Jul. 19, 2020

(65) Prior Publication Data

US 2021/0017314 A1    Jan. 21, 2021

Related U.S. Application Data

(60) Provisional application No. 62/876,441, filed on Jul. 19, 2019.

(51) Int. Cl.
| | | |
|---|---|---|
| *C08F 220/28* | (2006.01) | |
| *A61K 47/65* | (2017.01) | |
| *A61K 47/60* | (2017.01) | |
| *C08F 220/36* | (2006.01) | |
| *C08F 8/12* | (2006.01) | |

(52) U.S. Cl.
CPC .......... *C08F 220/281* (2020.02); *A61K 47/60* (2017.08); *A61K 47/65* (2017.08); *C08F 220/36* (2013.01)

(58) Field of Classification Search
CPC .......... C08F 220/281; C08F 220/36; C08F 2438/03; C08F 220/283; C08F 8/12; A61K 47/60; A61K 47/65
See application file for complete search history.

(56) References Cited

PUBLICATIONS

Dutta, K., D. Hu, B. Zhao, A. Ribbe, J. Zhuang and S. Thayumanavan, "Templated Self-Assembly of a Covalent Polymer Network for Intracellular Protein Delivery and Traceless Release", J. Am. Chem. Soc. 2017, 139, pp. 5676-5679. (Year: 2017).*

* cited by examiner

*Primary Examiner* — Joseph R Kosack
*Assistant Examiner* — Sagar Patel
(74) *Attorney, Agent, or Firm* — Milstein Zhang & Wu LLC

(57) ABSTRACT

The invention provides novel polymer-protein conjugates and molecular assemblies for controlled intracellular delivery of proteins, and compositions and methods of preparation and use thereof.

10 Claims, 36 Drawing Sheets

Scheme 1

PROTEIN-POLYMER NANOASSEMBLIES AND INTRACELLULAR PROTEIN DELIVERY

PRIORITY CLAIMS AND RELATED APPLICATIONS

This application claims the benefit of priority to U.S. Provisional Application No. 62/876,441, filed Jul. 20, 2019, the entire content of each of which is incorporated herein by reference for all purposes.

STATEMENT REGARDING FEDERALLY FUNDED RESEARCH OR DEVELOPMENT

This invention was made with government support under grant number GM128181. awarded by the National Institutes of Health. The Government has certain rights in the invention.

TECHNICAL FIELDS OF THE INVENTION

The invention generally relates to polymer-protein conjugates and protein delivery. More particularly, the invention relates to molecular assemblies of polymer-protein conjugates and controllable intracellular delivery of proteins in response to specific microenvironment, and compositions and methods of preparation and use thereof.

BACKGROUND OF THE INVENTION

Reaction between large molecules is an inherently slow process, especially when one of the reactive components involve functional groups on protein surfaces, because the reactive functionalities are heterogeneously distributed in low densities across large surfaces. Compared to the classical small molecule-based organic reactions that are typically carried out at high mM concentrations, proteins have lower reaction concentration limits ($\mu$M) and lower conjugation efficiency. In addition, the larger sizes of the reactive components would contribute to slow diffusion rates and low collision frequency. (White, et al. *ACS Cent. Sci.* 2018, 4, 197-206.)

Programmable polymer-protein conjugates have implications in several applications, including sensing in complex environments, enzyme catalysis in incompatible media, and delivery of biologics. (Cobo, et al. *Nat. Mater.* 2015, 14, 143-159; Droumaguet, et al. *Angew. Chem. Int. Ed.* 2008, 47, 6263-6266; Huang, et al. *Nat. Commun.* 2013, 4, 2239; Velonia, et al. *J. Am. Chem. Soc.* 2002, 124, 4224-4225; Nguyen, et al. *Nat. Chem.* 2013, 5, 221-227; Baslé, et al. *Chem. Biol.* 2010, 17, 213-227; Brodin, et al. *J. Am. Chem. Soc.* 2015, 137, 14838-14841; Danial, et al. *J. Am. Chem. Soc.* 2014, 136, 8018-8026; Dutta, et al. *J. Am. Chem. Soc.* 2017, 139, 5676-5679; Ventura, et al. *Biomacromolecules* 2015, 16, 3161-3171.)

Despite its potential in several diseases, transporting proteins across the cellular membrane remains a challenge that requires urgent attention. As proteins orchestrate most of the critical cellular processes, imbalance in the activity of intracellular proteins forms the basis for many human diseases. Although straightforward in principle to simply use the deficient protein itself as the therapeutic, such an approach is complicated by the fact that proteins are structurally fragile in non-native environments and are impermeable to cellular membrane. Several protein delivery systems are being developed to mitigate these risks. However, vast majority of these approaches have focused on extracellular targets, such as with delivering antibodies to cell surfaces and addressing insulin deficiencies. (D'Astolfo, et al. *Cell* 2015, 161, 674-690; Zhou, H et al. *Cell Stem Cell* 2009, 4, 381-384; Jakka, et al. *Angew. Chem. Int. Ed.* 2019, 58, 7713-7717; Yin, et al. *Nat. Biotechnol.* 2016, 34, 328-333; Zuris, et al. *Nat. Biotechnol.* 2014, 33, 73-80; Jo, et al. *Nat. Med.* 2005, 11, 892-898; Cardinale, et al. *Trends Mol. Med.* 2008, 14, 373-380; Mo, et al. *Chem. Soc. Rev.* 2014, 43, 3595; Leader, et al. *Nat. Rev. Drug Discov.* 2008, 7, 21-39; Pavlou, et al. *Nat. Biotech.* 2004, 22, 1513-1519; Caravella, et al. *Curr. Opinion Chem. Biol.* 2010, 14, 520-528.)

There have been previous reports of encapsulating and delivering proteins. Encapsulation using polyelectrolyte complexes and liposomal assemblies constitute two of the major approaches. The polyelectrolyte method is simple and fast, which typically utilizes a positively charged polymer or nanoparticle to bind to a negatively charged protein. (Zuris, et al. *Nat. Biotechnol.* 2014, 33, 73-80; Salmaso, et al. *Int. J. Pharm.* 2013, 440, 111-123; Scaletti, et al. *Chem. Soc. Rev.* 2018, 47, 3421-3432; Liu, et al. *ACS Appl. Mater. Interfaces* 2017, 9, 2023-2028; Fegan, et al. *Chem. Rev.* 2010, 110, 3315-3336; Luo, et al. *Chem. Rev.* 2016, 116, 13571-13632; Dun, et al. *J. Am. Chem. Soc.* 2017, 139, 13960-13968; Matsuurua, et al. *RSC Adv.* 2014, 4, 2942-2953; Doolan, et al. *Chem. Eur.* 1 2018, 24, 984-991; Gu, et al. *Chem. Soc. Rev.* 2011, 40, 3638-3655; Lu, et al. *J. Controlled Release* 2014, 194, 1-19; Lam, et al. *Biomacromolecules* 2016, 17, 2820-2829; Lee, et al. *Angew. Chem., Int. Ed.* 2009, 48, 5309-5312; Ghosh, et al. *J. Am. Chem. Soc.* 2010, 132, 2642-2645; Gonzalez-Toro, et al. *J. Am. Chem. Soc.* 2012, 134, 6964-6967.)

As the overall surface charge of these complexes is positive, they exhibit the tendency to be transported across the negatively charged cellular membrane. However, these complexes with positive surface charges do tend to suffer from non-specific fouling by serum proteins and associated toxicities. (Lv, et al. *J. Controlled Release* 2006, 114, 100-109; Fröhlich, et al. *Int. J. Nanomedicine* 2012, 7, 5577-5591; Intra, et al. *J. Controlled Release* 2008, 130, 129-138.)

Liposome surfaces, on the other hand, can be made to avoid non-specific fouling by using charge-neutral lipids, but the amount of proteins that can be loaded in a unit volume of these assemblies tends to be quite limited. This is due to the lack of a driving force for the water-soluble proteins to be sequestered within the aqueous lumen of the liposomes, compared to the bulk aqueous phase. (Swaminathan, et al. *Expert Opin. Drug Delivery* 2012, 9, 1489-1503; Chatin, et al. *Mol. Ther. Nucleic Acids* 2015, 4, e244.)

Covalent conjugation of polymeric molecules to proteins has been explored, especially in the context of stabilizing the latter, a popular example being the so-called PEGylation of proteins. Earlier approaches to attaching polymers to proteins involved the formation of stable conjugates, where the success metrics relied on whether the modification affected the native activity of the protein. (Cobo, et al. *Nat. Mater.* 2015, 14, 143-159; Droumaguet, et al. *Angew. Chem. Int. Ed.* 2008, 47, 6263-6266; Huang, et al. *Nat. Commun.* 2013, 4, 2239; Velonia, et al. *J. Am. Chem. Soc.* 2002, 124, 4224-4225; Nguyen, et al. *Nat. Chem.* 2013, 5, 221-227; Basle, et al. *Chem. Biol.* 2010, 17, 213-227; Brodin, et al. *J. Am. Chem. Soc.* 2015, 137, 14838-14841; Danial, et al. *J. Am. Chem. Soc.* 2014, 136, 8018-8026; Dutta, et al. *J. Am. Chem. Soc.* 2017, 139, 5676-5679; Ventura, et al. *Biomacromolecules* 2015, 16, 3161-3171; Gu, et al. *Chem. Soc. Rev.* 2011, 40, 3638-3655; Mummidivarapu, et al. *Bioconjugate*

*Chem.* 2018, 29, 3999-4003; Khondee, S et al. *Biomacromolecules* 2011, 12, 3880-3894; Ellis, et al. *J. Am. Chem. Soc.* 2012, 134, 3631-3634; Rudolph, et al. *In Protein Function: A Practical Approach,* 2nd ed.; Creighton, T. E., Ed.; Oxford: New York, 1997; p 64.)

As these modifications did affect protein activities in many cases, there have been a few reports that introduced conjugation through reversible chemical bonds. Despite the promise and many great advances in efficient organic synthetic methodologies, there is a dearth of successful methodologies for the transmembrane transport of active proteins using these approaches. (Dutta, et al. *J. Am. Chem. Soc.* 2017, 139, 5676-5679; Ventura, et al. *Biomacromolecules* 2015, 16, 3161-3171; Chiper, et al. *Adv. Healthcare Mater.* 2018, 7, 1701040; Qian, et al. *Angew. Chem. Int. Ed.* 2018, 57, 1532-1536; Wang, et al. *Angew. Chem., Int. Ed.* 2014, 53, 13444-13448.)

Accordingly, an ongoing need remains for an effective delivery vehicle for proteins, one that is preferably capable of traceless release of proteins that retain their native activities permitting practical therapeutic applications.

SUMMARY OF THE INVENTION

The invention provides a novel delivery platform for intracellular delivery of proteins that offers rapid and reversible conjugation capabilities. Surface modified proteins can be rapidly conjugated with polymers, which can be fully reversed in the presence of a specific and biologically relevant stimulus at the delivery site, e.g., reactive oxygen species, reducing environment, or variations in pH. The utility of this self-assembly process is demonstrated with intracellular delivery of proteins with retained function.

Modifications in the linker chemistry offers the ability to trigger these assemblies with various chemical inputs. Efficient formation of nanoassemblies based on polymer-protein conjugates has implications in a variety of areas at the interface of chemistry with materials and biology, such as in the generation of active surfaces and in delivery of biologics.

In one aspect, the invention generally relates to a functionalized copolymer, comprising: a first monomer of PEG-methacrylate (PEG-MA); and a second monomer of methacrylate having a side chain modified with a salicylhydroxamate moiety.

In another aspect, the invention generally relates to a surface modified protein comprising arylboronic acid modifications of one or more lysine residues.

In yet another aspect, the invention generally relates to a polymer-protein conjugate, comprising: a copolymer comprising a first monomer of PEG-methacrylate (PEG-MA) and a second monomer of methacrylate having a side chain conjugated to a protein via a degradable linker.

In yet another aspect, the invention generally relates to a molecular assembly comprising the polymer-protein conjugate disclosed herein.

In yet another aspect, the invention generally relates to a composition comprising the molecular assembly disclosed herein.

In yet another aspect, the invention generally relates to a method for delivering a protein, comprising: surface functionalizing the protein with arylboronic acid modifications of one or more lysine residues on the protein; forming a polymer-protein conjugate by reacting the surface functionalized protein with a copolymer comprising a first monomer of PEG-methacrylate (PEG-MA) and a second monomer of methacrylate having a side chain modified by a salicylhydroxamate moiety thereby forming a molecular assembly comprising the polymer-protein conjugate, wherein the polymer-protein conjugate comprises a degradable linker; transporting the molecular assembly to a target site to degrade the linker (and thus the molecular assembly) thereby releasing the protein at the target site.

In yet another aspect, the invention generally relates to a method for forming a molecular assembly, comprising: surface functionalizing the protein with arylboronic acid modifications of one or more lysine residues on the protein; and reacting the surface functionalized protein with a copolymer comprising a first monomer of PEG-methacrylate (PEG-MA) and a second monomer of methacrylate having a side chain modified by a salicylhydroxamate moiety thereby forming a molecular assembly comprising the polymer-protein conjugate.

BRIEF DESCRIPTION OF THE FIGURES

FIG. 8. $^1$H NMR spectrum of molecule 3a.
FIG. 24. $^1$H NMR spectrum of molecule 7a.
FIG. 25. $^{13}$C NMR spectrum of molecule 7a.

modification of lysine surface functional groups in proteins with boronic acid with an intervening pH-sensitive linker, where lowering the pH would result in traceless protein release; b) SDS-PAGE gel data, illustrating the complexation and stimulus-induced disassembly of the complex (lane 1: RNase A-BA_pH; lane 2: complex, lane 3: complex @ acidic condition); c) cytotoxicity of RNaseA-BA with the pH sensitive linker attached to the protein (after 48 h incubation), which indicates that RNaseA-BA with pH sensitive linker by itself does not have access to the cytosol of cells; d) cytotoxicity of the pH-sensitive RNaseA-polymer complex after incubation with HeLa cells.

Figure 51:
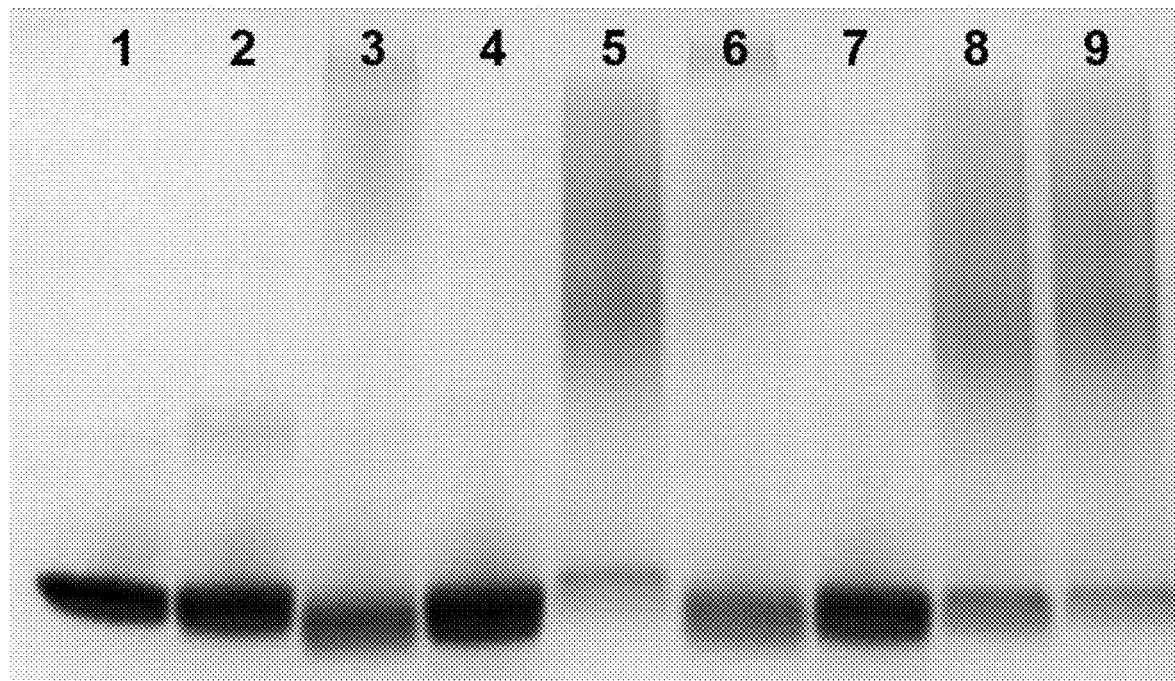

FIG. 51. Gel for redox responsiveness of RNase A and related complex. Lane 1, RNase A; Lane 2, RNase A-SS-BA; Lane 3, RNase A-SS-BA+GSH (10 mM); Lane 4, RNase A+polymer (1:10); Lane 5, RNase A-SS-13A+polymer (1:10); Lane 6, 5+GSH (10 mM); Lane 7, 5+DTT (10 mM); Lane 8, 5+$H_2O_2$ (10 mM); Lane 9, 5+Glucose (2 mg/mL).

Figure 52:
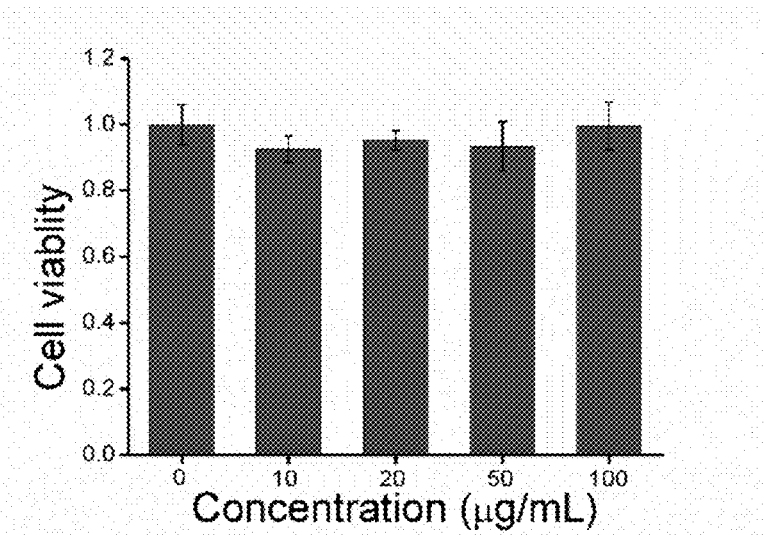

FIG. 52. Cytotoxicity of RNase A-SS-BA after 48 h incubation (HeLa cell, MTT assay).

Figure 53:
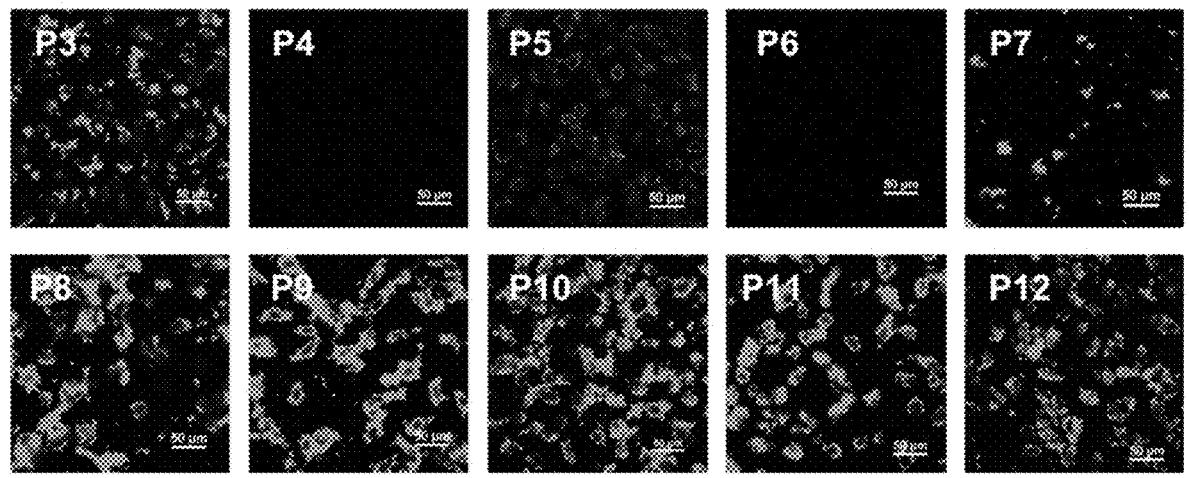

FIG. 53. Confocal images for cell uptake based on different polymers.

Figure 54:
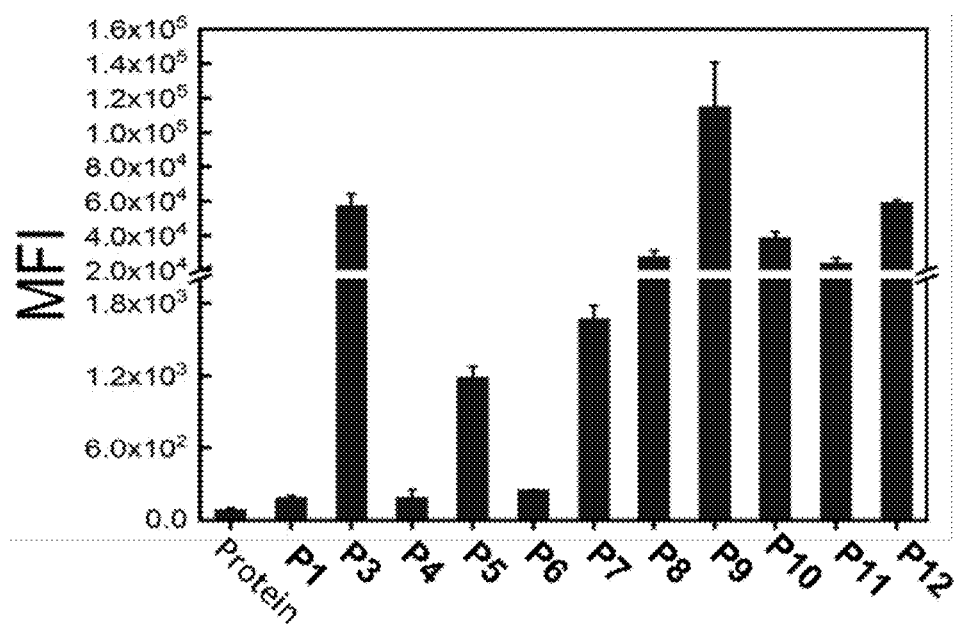

FIG. 54. Flow cytometry for quantification of cell uptake based on different polymers.

Figure 55:
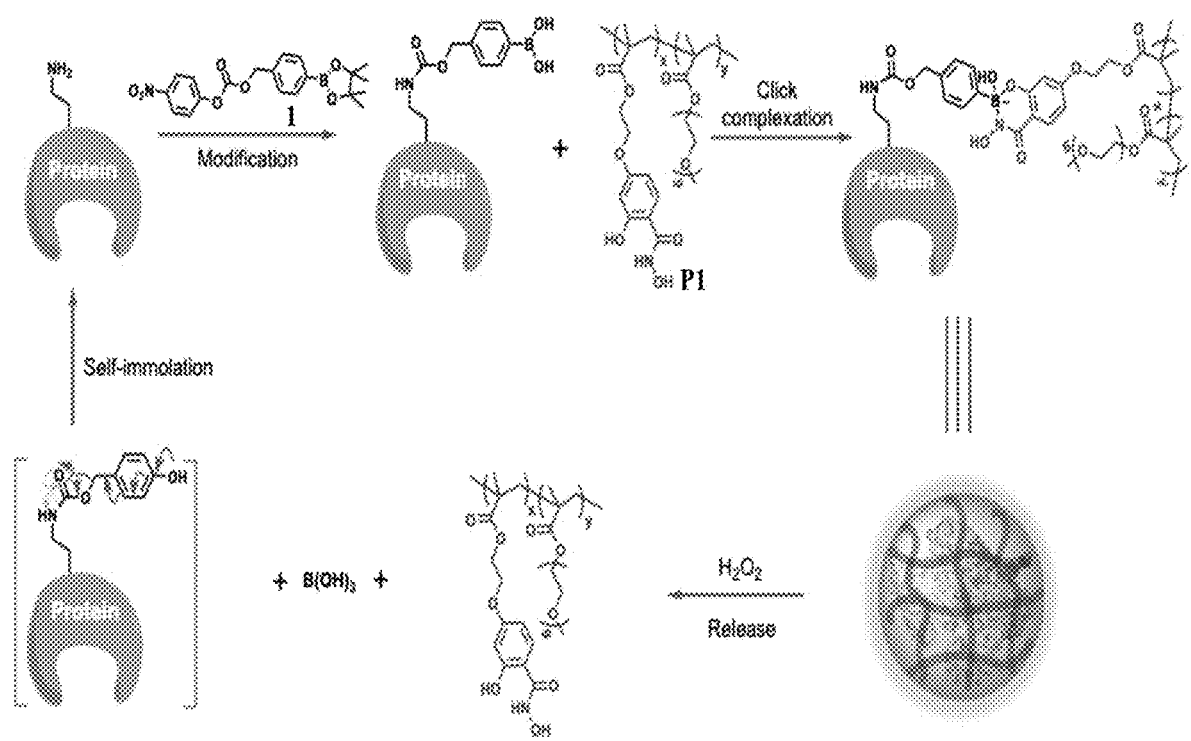

FIG. 55. Structure of the molecule 1, involved in the modification of surface lysines in proteins, structure of the polymer P1, used for the click-induced formation of the polymer-protein complex. This complex can then be degraded to afford the protein, without any remnants of the polymer in the presence of a reactive oxygen species stimulus.

Figure 56:
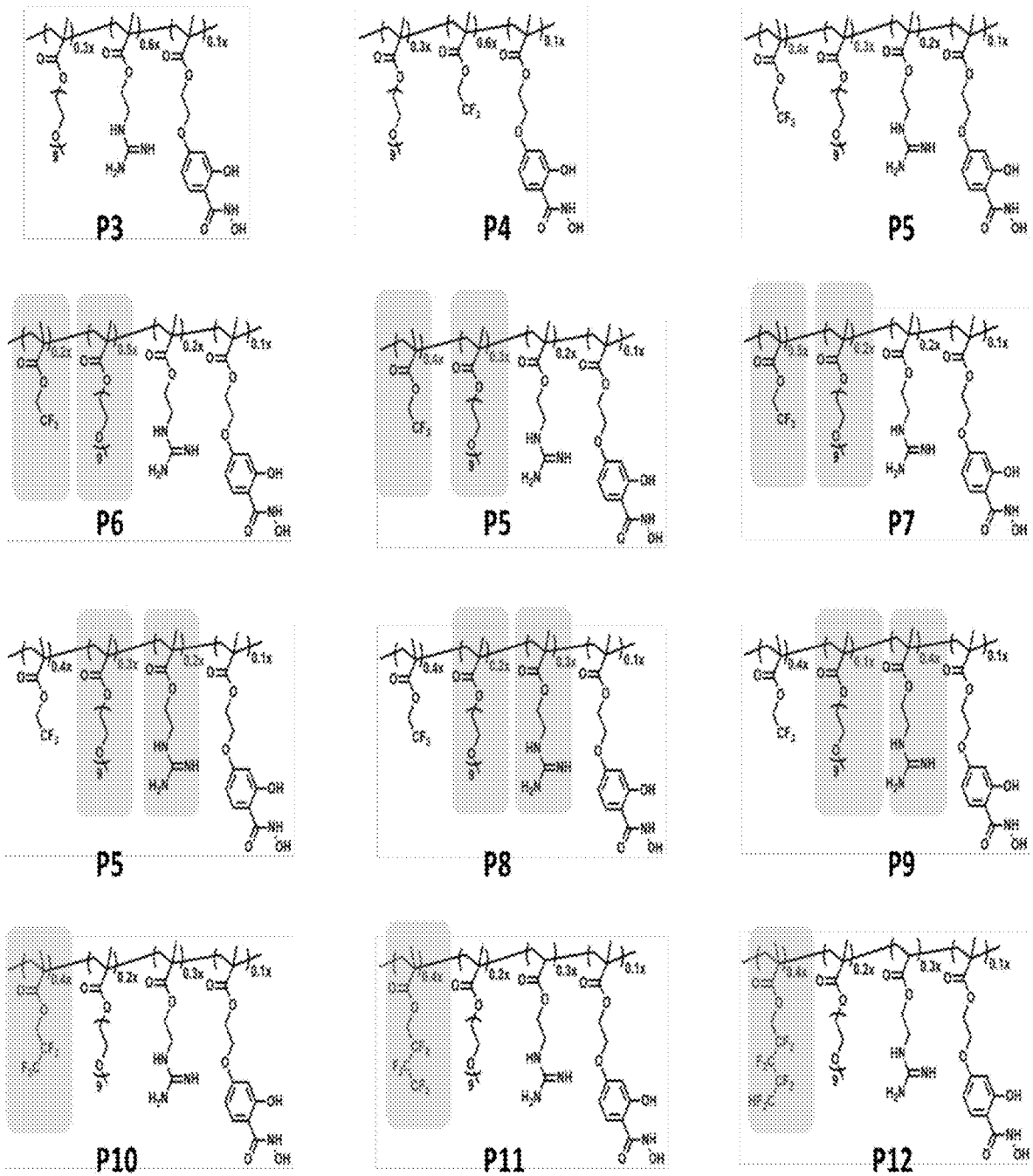

FIG. 56. Structures of certain exemplified polymers.

Figure 57:
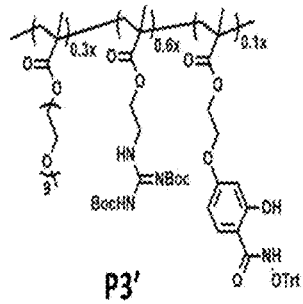
Figure 57:
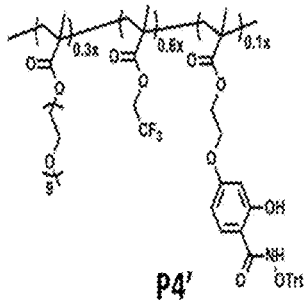
Figure 57:
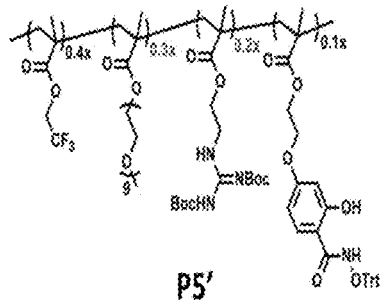
Figure 57:
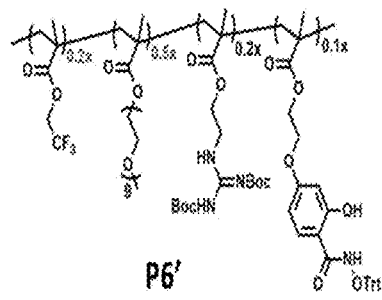
Figure 57:
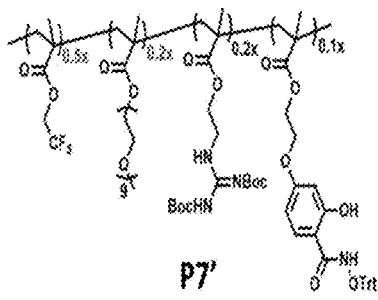
Figure 57:
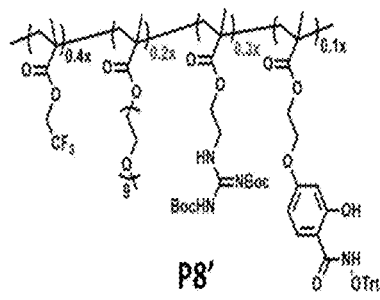
Figure 57:
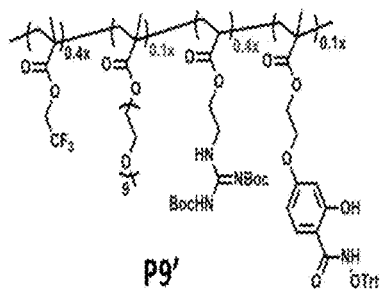
Figure 57:
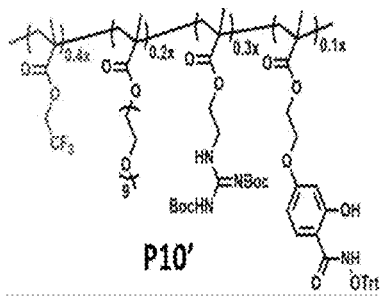
Figure 57:
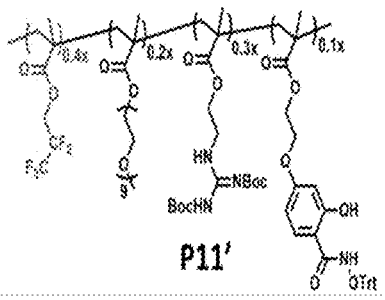
Figure 57:
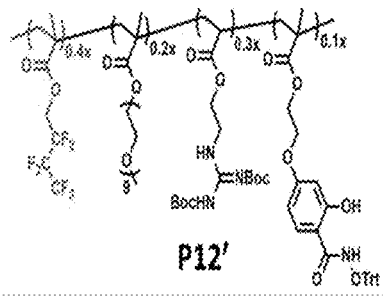

FIG. 57. Structures of polymer structures P3'-P12'.

DETAILED DESCRIPTION OF THE INVENTION

The present invention provides an efficient and effective delivery platform for intracellular delivery of proteins. The protein delivery system disclosed herein is a simple click chemistry approach, a simple and rapid 'mix and go' approach, that offers rapid and reversible conjugation capabilities, which are typical to non-covalent interactions, combined with the robust conjugate stability, a key characteristic of covalent methods.

Figure 1:
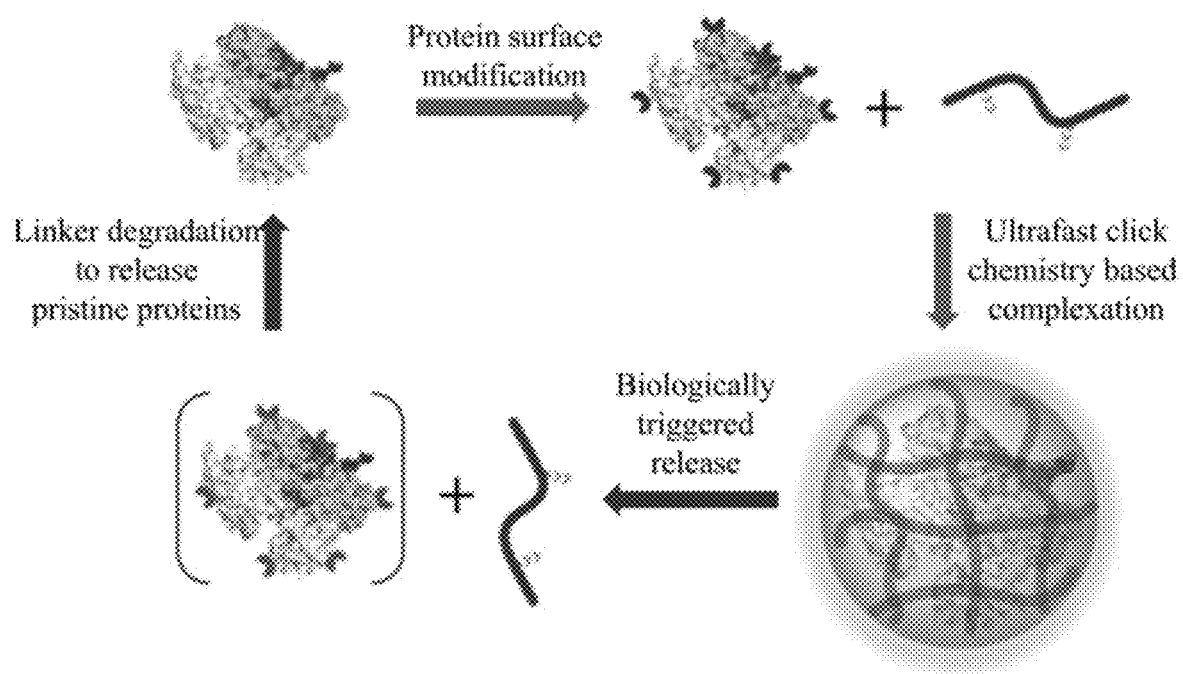
FIG. 1. Polymer-protein assembly formation and disassembly process. Modification of lysine surface functional groups in proteins with arylboronic acid; Protein-polymer complexation through a reversible click reaction between protein and polymer; Stimuli induced disassembly of the protein-polymer complex to release the protein with a traceless form.

As illustrated in FIG. 1, the protein delivery approach has the potential to present a non-fouling surface with robust conjugate stability characteristics offered by the covalent methods.

Construction of polymer-protein nanoassemblies is a challenge as reactions between macromolecules, especially those involving proteins, are inherently inefficient owing to the sparse reactive functional groups and low concentration requirements. This challenge was addressed herein using an ultrafast and reversible click reaction, which forms the basis for a covalent self-assembly strategy between side-chain functionalized polymers and surface-modified proteins.

Linkers embedded in the molecular assembly have been programmed to release the incarcerated proteins in its native form, only when subjected to the presence of a specific trigger. The generality and the versatility of the approach are herein demonstrated by showing that the disclosed approach can be used for proteins of different sizes and isoelectric points.

Surface modified proteins can be rapidly conjugated with polymers, which can be fully reversed in the presence of a specific and biologically relevant stimulus. The broad applicability of the molecular design strategy has been illustrated with encapsulations of proteins of different sizes and isoelectric points (pI) and the release of encapsulated proteins in response to three different stimuli, viz. reactive oxygen species (ROS), reducing environment, and variations in pH. In addition to the encapsulation and release of proteins, the utility of this self-assembly process is also demonstrated with intracellular delivery of these proteins with retention of function.

Modifications in the linker chemistry offers the ability to trigger these assemblies with various chemical inputs. Efficient formation of nanoassemblies based on polymer-protein conjugates has implications in a variety of areas at the interface of chemistry with materials and biology, such as in the generation of active surfaces and in delivery of biologics.

In one aspect, the invention generally relates to a functionalized copolymer, comprising: a first monomer of PEG-methacrylate (PEG-MA); and a second monomer of methacrylate having a side chain modified with a salicylhydroxamate moiety.

In certain embodiments of the functionalized copolymer, the first monomer is the majority monomer and the second monomer is the minority monomer.

In certain embodiments, the first monomer comprises a side chain comprising from about 1 to about 20 (e.g., from about 1 to about 15, from about 1 to about 10, from about 1 to about 5, from about 5 to about 20, from about 10 to about 20, from about 5 to about 15, from about 5 to about 10) ethylene-oxide units.

In certain embodiments, the first monomer has the structure of:

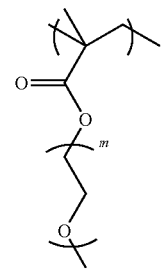

where m is an integer in the range of 1 to 20 (e.g., from about 1 to about 15, from about 1 to about 10, from about 1 to about 5, from about 5 to about 20, from about 10 to about 20, from about 5 to about 15, from about 5 to about 10).

In certain embodiments, the second monomer comprises:

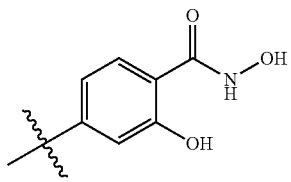

or a protected form thereof.

In certain embodiments, the second monomer has the structure of:

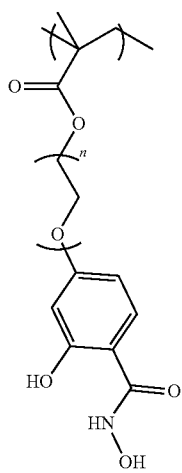

or a protected form thereof, where n is an integer in the range of 1 to 20 (e.g., from about 1 to about 15, from about 1 to about 10, from about 1 to about 5, from about 5 to about 20, from about 10 to about 20, from about 5 to about 15, from about 5 to about 10).

In certain embodiments, the functionalized copolymer has the structural formula:

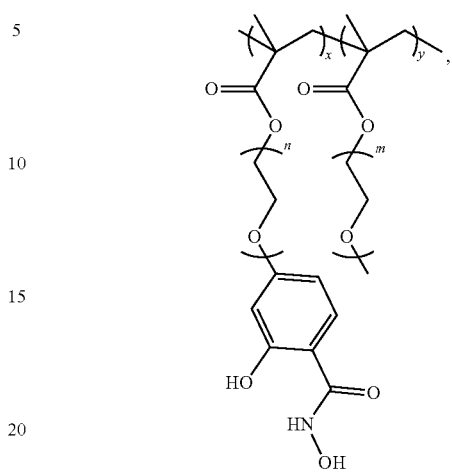

wherein each of m and n is independently an integer in the range of 1 to 20 (e.g., from about 1 to about 15, from about 1 to about 10, from about 1 to about 5, from about 5 to about 20, from about 10 to about 20, from about 5 to about 15, from about 5 to about 10), and x:y is in the range from about 5:95 to about 70:30 (e.g., from about 5:95 to about 60:40, from about 5:95 to about 50:50, from about 10:90 to about 70:30, from about 20:80 to about 70:30, from about 30:70 to about 70:30, from about 40:60 to about 70:30, from about 50:50 to about 70:30, about 1:1).

In certain embodiments, the functionalized copolymer has a molecular weight ($M_w$) in the range of about 1 k to about 200 k (e.g., about 1 k to about 100 k, about 1 k to about 50 k, about 1 k to about 20 k, about 1 k to about 10 k, about 5 k to about 200 k, about 10 k to about 200 k, about 20 k to about 200 k, about 50 k to about 200 k, about 5 k to about 50 k, about 5 k to about 20 k).

In another aspect, the invention generally relates to a surface modified protein comprising arylboronic acid modifications of one or more lysine residues.

In certain embodiments of the surface modified protein, the arylboronic acid is a phenylboronic acid.

In certain embodiments, one or more lysine residues of the protein is modified by

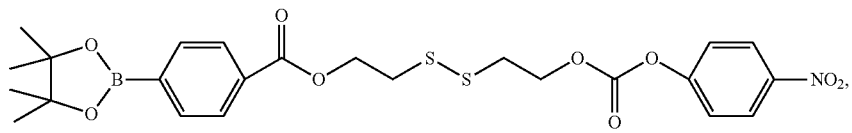

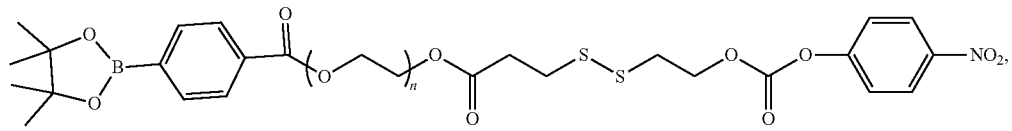

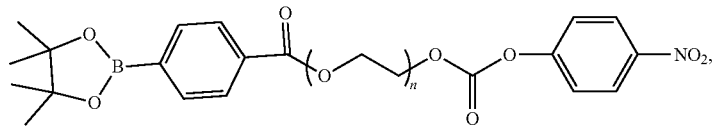

-continued

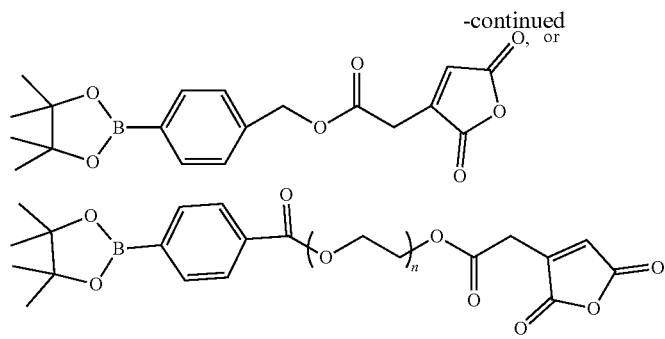

wherein n is an integer in the range of 1 to 20 (e.g., from about 1 to about 15, from about 1 to about 10, from about 1 to about 5, from about 5 to about 20, from about 10 to about 20, from about 5 to about 15).

In certain embodiments, the arylboronic acid modification is conjugated to the protein via a degradable linker sensitive to reactive oxygen species, a reducing environment, or change in pH.

In certain embodiments, the reactive oxygen species is hydrogen peroxide. In certain embodiments, the reducing environment is offered by higher intracellular glutathione (GSH) concentrations. In certain embodiments, change in pH is caused by a lower pH of cellular microenvironments (e.g., in cancer cells and in endosomal/lysosomal compartments).

In certain embodiments, the arylboronic acid modification is conjugated to the protein via a boronate ester linker. In certain embodiments, the arylboronic acid modification is conjugated to the protein via a disulfide linker. In certain embodiments, the arylboronic acid modification is conjugated to the protein via a cis-aconityl linker.

In certain embodiments, the protein has a molecular weight in the range of about 10 k to about 500 k (e.g., about 20 k to about 500 k, about 50 k to about 500 k, about 100 k to about 500 k, about 10 k to about 100 k, about 10 k to about 50 k).

In certain embodiments, the protein has an isoelectric points (pI) in the range of about 3.0 to about 12.0 (e.g., about 5.0 to about 12.0, about 7.0 to about 12.0, about 9.0 to about 12.0, about 3.0 to about 9.0, about 3.0 to about 7.0, about 3.0 to about 5.0, about 5.0 to about 10.0).

In yet another aspect, the invention generally relates to a polymer-protein conjugate, comprising: a copolymer comprising a first monomer of PEG-methacrylate (PEG-MA) and a second monomer of methacrylate having a side chain conjugated to a protein via a degradable linker.

In certain embodiments of the polymer-protein conjugate, wherein the degradable linker is sensitive to reactive oxygen species, a reducing environment, or change in pH. In certain embodiments, the reactive oxygen species is hydrogen peroxide ($H_2O_2$). In certain embodiments, the reducing environment is offered by higher intracellular glutathione concentrations. In certain embodiments, change in pH is caused by a lower pH of cellular microenvironments (e.g., in cancer cells and in endosomal/lysosomal compartments).

In certain embodiments, the degradable linker comprises a boronate ester linker. In certain embodiments, the degradable linker comprises a disulfide linker. In certain embodiments, the degradable linker comprises a cis-aconityl linker.

In yet another aspect, the invention generally relates to a molecular assembly comprising the polymer-protein conjugate disclosed herein.

In certain embodiments of the molecular assembly, the polymer:protein ratio by weight is in the range from about 1:1 to about 50:1 (e.g., from about 1:1 to about 30:1, from about 1:1 to about 20:1, from about 1:1 to about 10:1, from about 1:1 to about 5:1, from about 1:1 to about 3:1, from about 5:1 to about 50:1, from about 10:1 to about 50:1, from about 20:1 to about 50:1, from about 2:1 to about 10:1, from about 2:1 to about 8:1, from about 2:1 to about 5:1, from about 5:1 to about 10:1).

In certain embodiments, the polymer-protein conjugate is adapted to release the protein in its native form upon degradation of the degradable linker.

In certain embodiments, the degradable linker comprises a boronate ester linker. In certain embodiments, the degradable linker comprises a disulfide linker. In certain embodiments, the degradable linker comprises a cis-aconityl linker.

In certain embodiments, the polymer-protein conjugate is adapted to release the protein in the presence of a specific and biologically relevant stimulus inside cells. In certain embodiments, the polymer-protein conjugate is adapted to release the protein in the presence of a specific and biologically relevant stimulus in the cytosol.

In certain embodiments, the protein has a molecular weight in the range of about 10 k to about 500 k (e.g., about 20 k to about 500 k, about 50 k to about 500 k, about 100 k to about 500 k, about 10 k to about 100 k, about 10 k to about 50 k).

In certain embodiments, the protein has an isoelectric point (pI) in the range of about 3.0 to about 12.0 (e.g., about 5.0 to about 12.0, about 7.0 to about 12.0, about 9.0 to about 12.0, about 3.0 to about 9.0, about 3.0 to about 7.0, about 3.0 to about 5.0, about 5.0 to about 10.0).

In yet another aspect, the invention generally relates to a composition comprising the molecular assembly disclosed herein.

In yet another aspect, the invention generally relates to a method for delivering a protein, comprising: surface functionalizing the protein with arylboronic acid modifications of one or more lysine residues on the protein; forming a polymer-protein conjugate by reacting the surface functionalized protein with a copolymer comprising a first monomer of PEG-methacrylate (PEG-MA) and a second monomer of methacrylate having a side chain modified by a salicylhydroxamate moiety thereby forming a molecular assembly comprising the polymer-protein conjugate, wherein the polymer-protein conjugate comprises a degradable linker; transporting the molecular assembly to a target site to degrade the linker (and thus the molecular assembly) thereby releasing the protein at the target site.

In certain embodiments of the method, the target site is inside a cell. In certain embodiments, the protein is released for its native function in the presence of a specific and biologically relevant stimulus inside cells.

In certain embodiments, the target site is cytosol. In certain embodiments, the polymer-protein conjugate is adapted to release the protein in the presence of a specific and biologically relevant stimulus in the cytosol.

In certain embodiments, the specific and biologically relevant stimulus are reactive oxygen species (e.g., hydrogen peroxide). In certain embodiments, the specific and biologically relevant stimulus is a reducing environment offered by higher intracellular glutathione concentrations. In certain embodiments, the specific and biologically relevant stimulus is a change in pH is caused by a lower pH of cellular microenvironments (e.g., in cancer cells and in endosomal/lysosomal compartments).

In certain embodiments, the polymer:protein ratio by weight is in the range from about 1:1 to about 50:1 (e.g., from about 1:1 to about 30:1, from about 1:1 to about 20:1, from about 1:1 to about 10:1, from about 1:1 to about 5:1, from about 1:1 to about 3:1, from about 5:1 to about 50:1, from about 10:1 to about 50:1, from about 20:1 to about 50:1, from about 2:1 to about 10:1, from about 2:1 to about 8:1, from about 2:1 to about 5:1, from about 5:1 to about 10:1).

In certain embodiments, the protein is released in its native form for its native function. In certain embodiments, the released protein retains at least 70% (e.g., at least 80%, at least 90%, at least 95%, at least 99%) of the activity of the native protein (i.e., the protein's native function).

The term "protein" as used herein refers to a polymer of amino acid residues (a "polypeptide") and is not limited to a minimum length. Thus, peptides, oligopeptides, dimers, multimers, and the like, are included within the definition. Both full-length proteins and fragments thereof are encompassed by the definition. The terms also include post-expression modifications of the polypeptide, for example, glycosylation, acetylation, phosphorylation, and the like. Furthermore, a polypeptide may refer to a protein which includes modifications, such as deletions, additions, and substitutions (generally conservative in nature), to the native sequence, as long as the protein maintains the desired activity. These modifications may be deliberate or may be accidental. Amino acids can be referred to herein by either their commonly known three letter symbols or by the one-letter symbols recommended by the IUPAC-IUB Biochemical Nomenclature Commission.

In certain embodiments, wherein the degradable linker comprises a boronate ester linker. In certain embodiments, the degradable linker comprises a disulfide linker. In certain embodiments, the degradable linker comprises a cis-aconityl linker.

In certain embodiments, the protein has a molecular weight in the range of about 10 k to about 500 k (e.g., about 20 k to about 500 k, about 50 k to about 500 k, about 100 k to about 500 k, about 10 k to about 100 k, about 10 k to about 50 k).

In certain embodiments, the protein has an isoelectric points (pI) in the range of about 3.0 to about 12.0 (e.g., about 5.0 to about 12.0, about 7.0 to about 12.0, about 9.0 to about 12.0, about 3.0 to about 9.0, about 3.0 to about 7.0, about 3.0 to about 5.0, about 5.0 to about 10.0).

In yet another aspect, the invention generally relates to a method for forming a molecular assembly, comprising: surface functionalizing the protein with arylboronic acid modifications of one or more lysine residues on the protein; and reacting the surface functionalized protein with a copolymer comprising a first monomer of PEG-methacrylate (PEG-MA) and a second monomer of methacrylate having a side chain modified by a salicylhydroxamate moiety thereby forming a molecular assembly comprising the polymer-protein conjugate.

In certain embodiments of the method, wherein the first monomer of the copolymer comprises a side chain comprising from about 1 to about 20 (e.g., from about 1 to about 15, from about 1 to about 10, from about 1 to about 5, from about 5 to about 20, from about 10 to about 20, from about 5 to about 15) ethylene-oxide units.

In certain embodiments, the first monomer has the structure of:

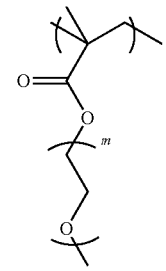

where m is an integer in the range of 1 to 20 (e.g., from about 1 to about 15, from about 1 to about 10, from about 1 to about 5, from about 5 to about 20, from about 10 to about 20, from about 5 to about 15).

In certain embodiments, the second monomer of the copolymer comprises:

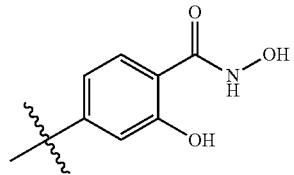

or a protected form thereof.

In certain embodiments, the second monomer has the structure of:

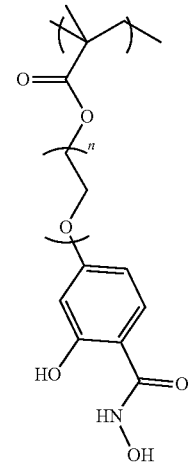

or a protected form thereof, where n is an integer in the range of 1 to 20 (e.g., from about 1 to about 15, from about 1 to about 10, from about 1 to about 5, from about 5 to about 20, from about 10 to about 20, from about 5 to about 15).

In certain embodiments, the copolymer has the structural formula:

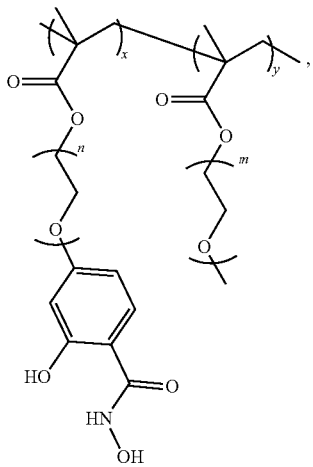

wherein each of m and n is independently an integer in the range of 1 to 20 (e.g., from about 1 to about 15, from about 1 to about 10, from about 1 to about 5, from about 5 to about 20, from about 10 to about 20, from about 5 to about 15), and x:y is in the range from about 5:95 to about 70:30 (e.g., from about 5:95 to about 60:40, from about 5:95 to about 50:50, from about 10:90 to about 70:30, from about 20:80 to about 70:30, from about 30:70 to about 70:30, from about 40:60 to about 70:30, from about 50:50 to about 70:30, about 1:1).

In certain embodiments, the copolymer has a molecular weight (MW) in the range of about 1 k to about 200 k (e.g., about 1 k to about 50 k, about 1 k to about 20 k, about 1 k to about 10 k, about 5 k to about 200 k, about 10 k to about 200 k, about 20 k to about 200 k, about 50 k to about 200 k, about 5 k to about 100 k, about 5 k to about 50 k).

In certain embodiments, one or more lysine residues of the protein is modified by

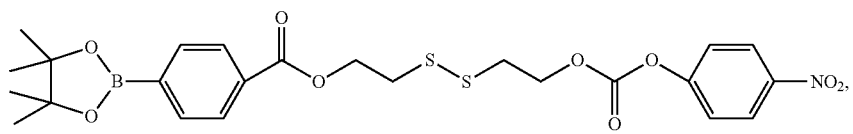

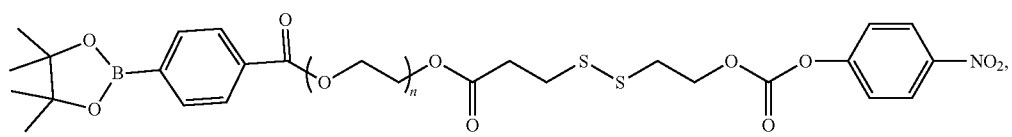

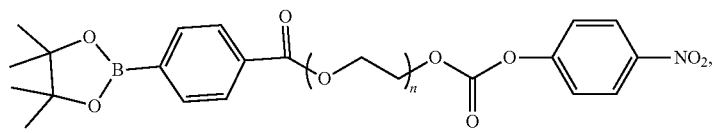

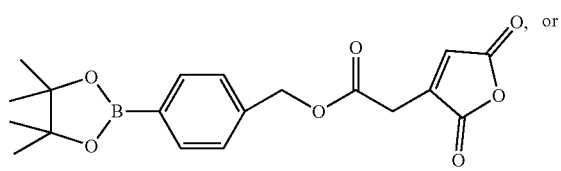

, or

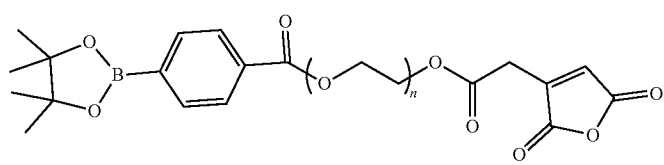

wherein n is an integer in the range of 1 to 20 (e.g., from about 1 to about 15, from about 1 to about 10, from about 1 to about 5, from about 5 to about 20, from about 10 to about 20, from about 5 to about 15).

Examples

Salicylhydroxamate-arylboronic acid combination was chosen as the click reaction of choice, because of its high efficiency with a typical reaction rate of $7 \times 10^6$ $M^{-2}s^{-1}$. (Arzt, et al. Chem. Asian J. 2014, 9, 1994-2003; Ng, et al. Angew. Chem. Int. Ed. 2014, 53, 324-328; Shin, et al. Chem. Biol. 2010, 17, 1171-1176.)

Neither of these functional groups, however, are natively present in proteins. Therefore, in order to use this click reaction as the key step in the polymer-protein conjugate formation, one of these functional groups must be installed on the protein surface. To insure broad applicability of this approach, it is also critical that an amino acid side chain functionality is chosen that is ubiquitous on protein surfaces. Thus, lysines were chosen as the functional handles to carry out the modification, as >80% of globular proteins have more than one lysine residue on their surface. Arylboronic acid was reportedly used to modify lysines. (Wong, et al. Adv. Drug Delivery Rev. 2012, 64, 1031-1045; Roth, et al. Chem. Rev. 2016, 116, 1309-1352; Blencowe, et al. Polym. Chem. 2011, 2, 773-790.)

Scheme 1 (FIG. 55) shows the molecular design of the disclosed approach, where lysines on protein surfaces are treated with the p-nitrophenylcarbonate of 4-hydroxymethyl-phenylboronate ester 1. The resultant lysine modification is hydrolytically stable. However, when the boronic acid moiety is converted to the corresponding phenol under oxidizing conditions, this functionality rapidly degrades back to the amine. This hydrogen peroxide induced reversibility of the lysine modification forms the basis for the traceless release of the proteins under ROS conditions.

To conjugate the polymer to the protein, the salicylhydroxamate moiety was installed on to a polymer. The targeted polymer structure is shown as P1 in Scheme 1. P1 contains a high percentage of polyethyleneglycol (PEG) functionalities (90%), because of a PEG-methacrylate (PEG-MA) is used as a comonomer. PEG-MA is used as a majority co-monomer in P1, as this should endow the polymer with water solubility and charge-neutral polymer-protein nanoassembly with non-fouling characteristics.

To achieve a salicylhydroxamate-based monomer, selective functionalization of the phenolic group at the para-position of 2,4-dihydroxybenzoic acid (2) was carried out to allow the installation of a polymerizable methacrylate moiety (molecule 3, Scheme 2). The precursor monomer in its trityl protected form, 4, was achieved by coupling the carboxylic acid moiety of 3 with protected hydroxylamine. The resultant monomer 4 was then copolymerized with PEG-MA (5) in 1:9 ratio to obtain the salicylhydroxamate functionalized polymer P1, as shown in Scheme 2. The polymerization was carried out under reversible-addition-fragmentation-chain-transfer (RAFT) reaction conditions.

Characterization of the polymer with $^1$H NMR revealed that the ratio of the two monomers correlated well with the feed ratio in the reaction. Gel permeation chromatography (GPC) characterization showed that the apparent molecular weight of the polymer is ~16 kDa with the polydispersity (Đ) of ~1.1. This medium sized polymer was chosen for efficient reaction between polymer and protein to prepare nanoassemblies. Finally, the salicylhydroxamate group was liberated by deprotection of the trityl group using trifluoroacetic acid.

Scheme 2. Synthesis of a) monomer 4, and b) polymer P1.

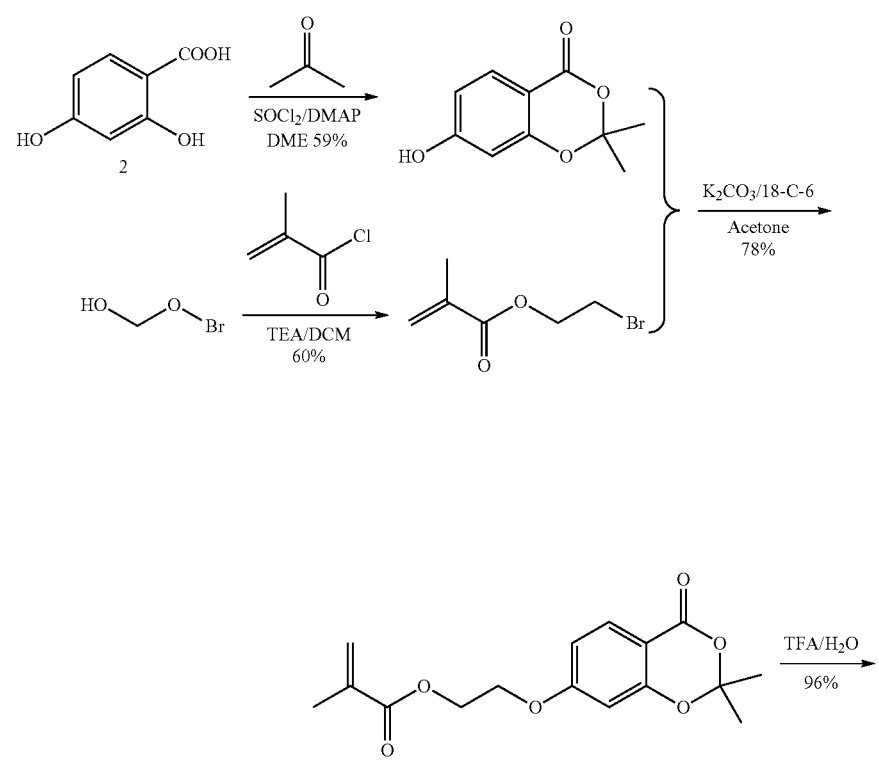

a

-continued
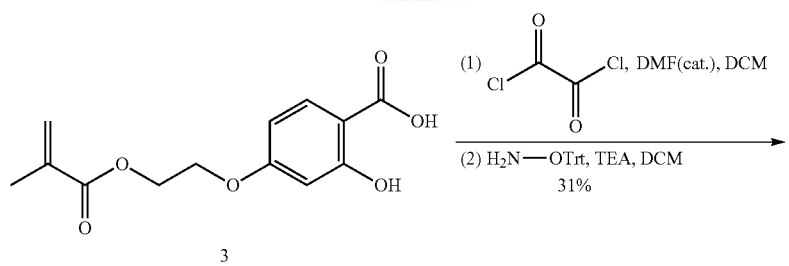
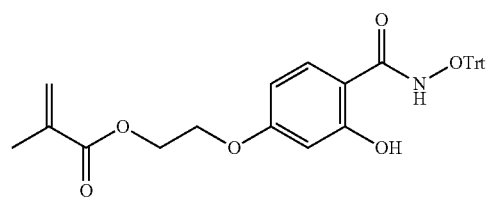
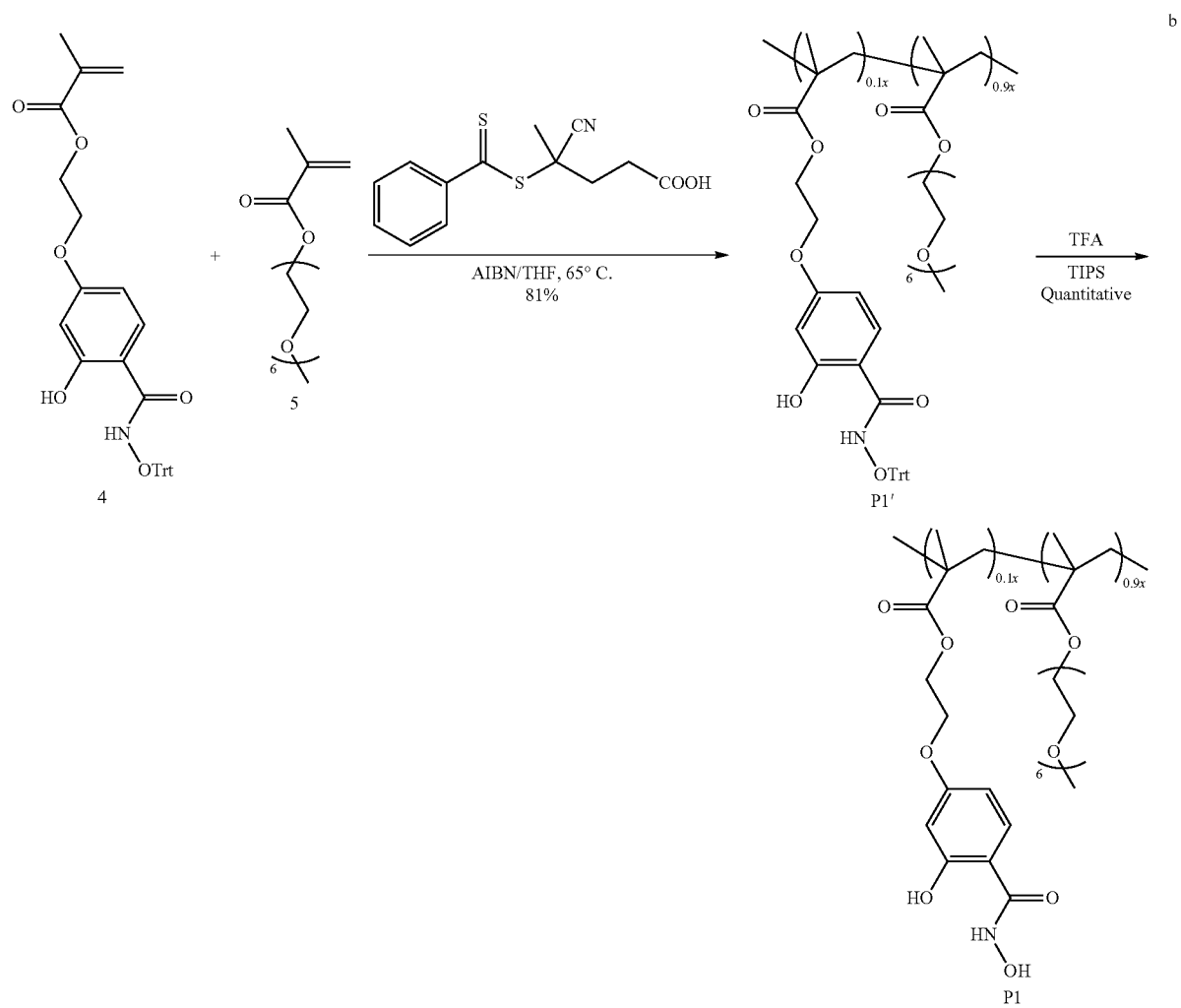

The fast reaction between the salicylhydroxamate moiety side chain in the polymer and the boronic acid surface functionalities in the protein should result in a rapid self-assembly to produce a nanoassembly, as illustrated in Scheme 1. To test this possibility, ribonuclease A (RNaseA, from bovine pancreas) was used as the model protein, which was chosen for its well-established fluorescence assay for enzymatic activity and apoptotic cellular activity. (Raines, et al. *Chem. Rev.* 1998, 98, 1045-1066.)

Figure 30:
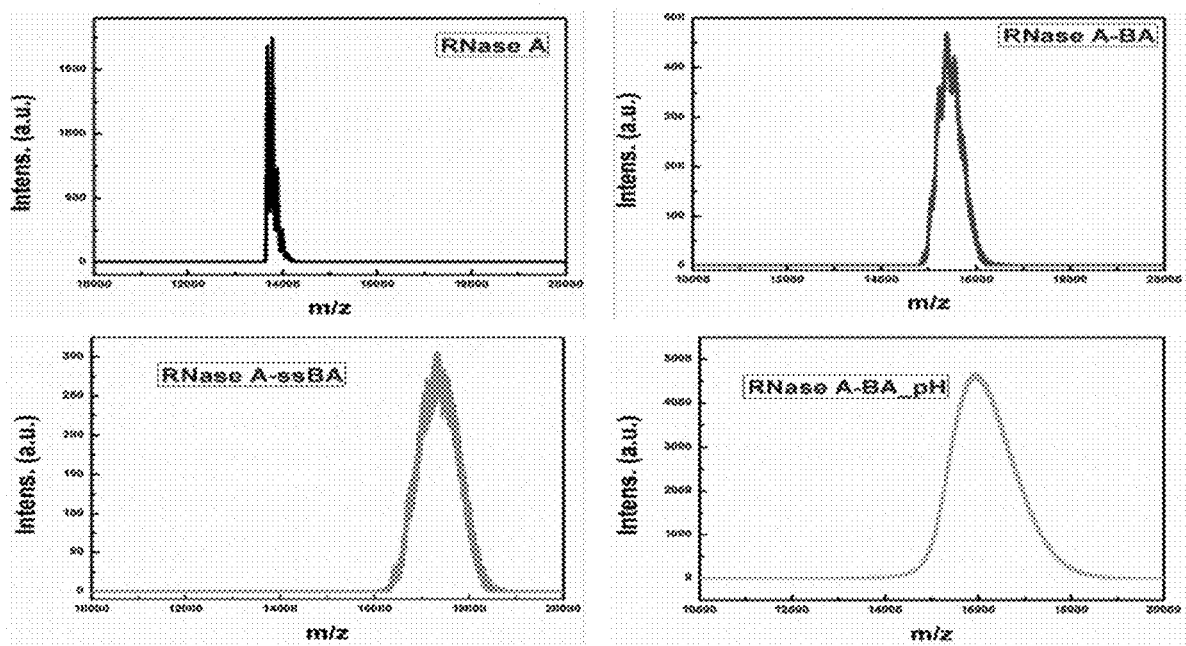
FIG. 30. MADLI-MS of RNase A before and after different sensitive linker modification. The Mw of unmodified RNase is 13700 Da. The average MWs for RNase A-BA, RNase A-SS-BA and RNase A-BA_pH are 15380, 17128 and 15930 respectively. Based on the calculation, the average amount of modification for RNase A-BA, RNase A-SS-BA and RNase A-BA_pH are 9, 10 and 8 respectively.

Treatment of RNaseA with 1 resulted in ~9 of the total of 11 lysine units on the protein surface to be modified to the corresponding arylboronic acid moiety, as estimated by MALDI-MS (FIG. 30).

Figure 2:
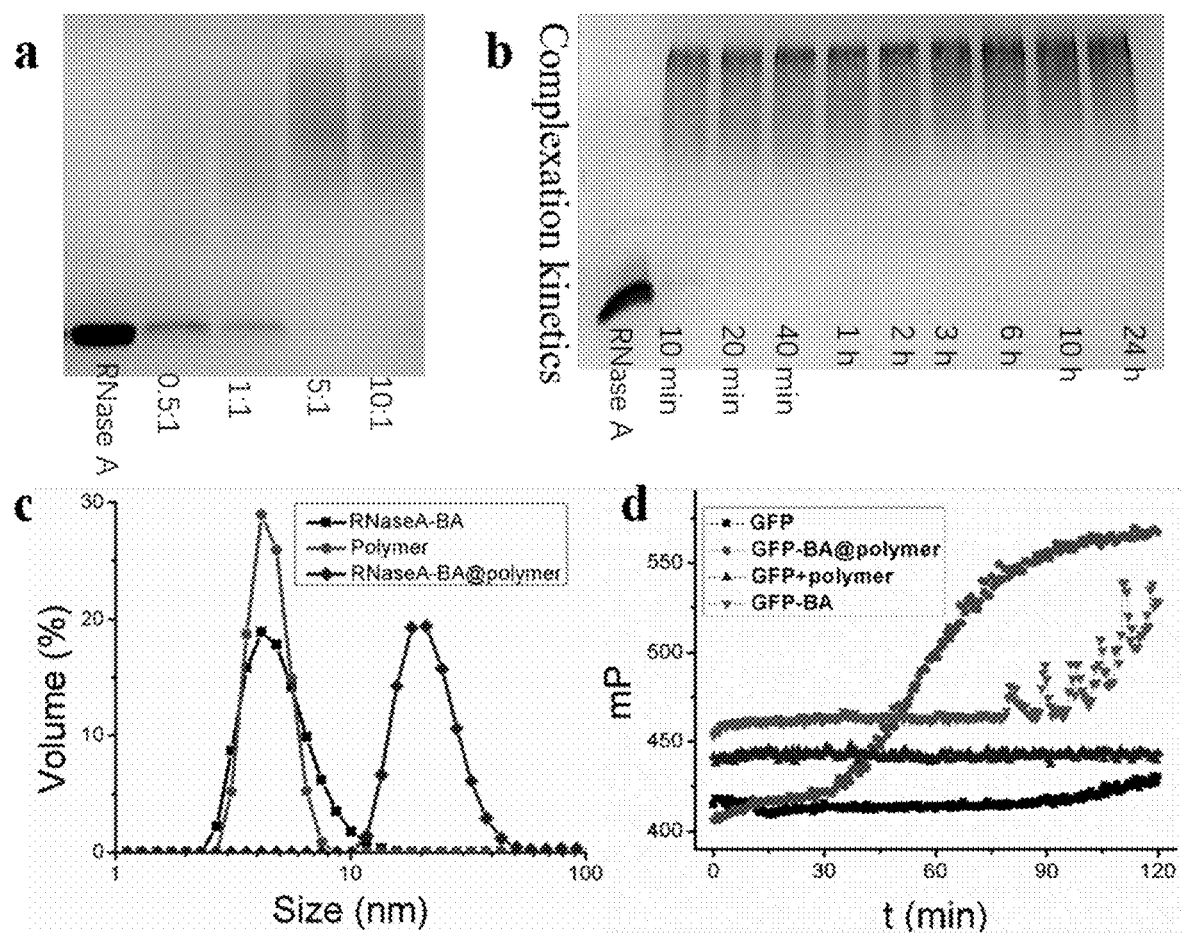
FIG. 2. Protein-polymer complex formation. a) SDS-PAGE gel for complexation between modified RNaseA and polymer P1 at 29 μM concentration of RNaseA; b) Complexation kinetics monitored through temporal evolution of the free protein concentration upon mixing modified RNaseA with the polymer P1; c) Analysis of size distribution of the protein, polymer, and the polymer-protein complex; d) Temporal evolution fluorescence polarization of the green fluorescent protein (GFP) in the presence of the polymer with time at 2.3 nM concentration at 1:10 ratio.
Figure 31:
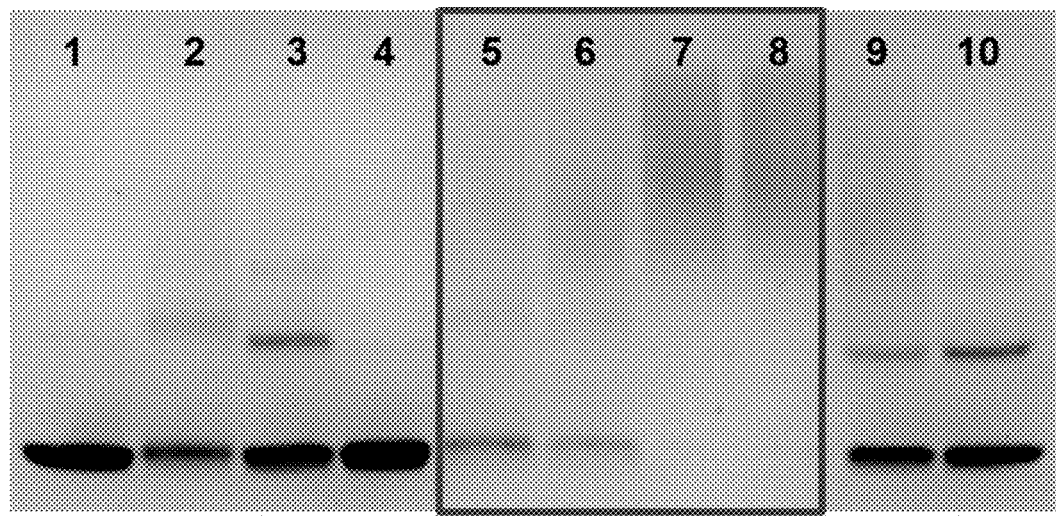
FIG. 31. Full gel for RNase A related complex. 1, RNase A; 2, RNase A-BA; 3, RNase A-BA+$H_2O_2$ (10 mM); 4, RNase A+polymer (1:10); 5-8, RNase A+polymer with different ratios (5, 1:0.5; 6, 1:1; 7, 1:5, 8, 1:10); 9-10, complex 7+$H_2O_2$ (9, 1 mM; 10, 10 mM).

The targeted protein-polymer complex was prepared by simply mixing the polymer P1 with the arylboronic acid-modified protein in water or PBS buffer. The product of this self-assembly process was characterized using a variety of techniques. First, dynamic light scattering (DLS) studies revealed that the solution size of the complex is ~20 nm, which is significantly higher than any of the control samples, i.e. the modified protein, unmodified protein, polymer P1, and the physical mixture of unmodified protein and P1 (FIG. 2c). Gel electrophoresis (SDS-PAGE) of the protein and the boronic acid modified protein showed a well-defined narrow band, as anticipated (FIGS. 2a and 31).

On the other hand, RNaseA-BA@polymer complex showed a relatively smeared band at the molecular weight range, which is substantially higher than that of both the polymer and the protein (FIG. 2a). Similarly, a physical mixture of the polymer and the unmodified protein did not cause the formation of any new band (FIG. 31).

These results indicate that the mixture of modified protein and the polymer results in the formation of a higher molecular weight protein complex, likely due to the rapid click reaction between the salicylhydroxamate and the aryl boronic acid moieties.

The complexation kinetics was evaluated using SDS-PAGE. The reaction between the polymer and the protein seemed to be complete even in 10 minutes with small remnants of unreacted protein (FIG. 2b). In under one hour, no discernible free protein could be observed in the gel. These data show that the complexation process is quantitative and fast, even at µM concentrations of the protein.

In order to further evaluate whether this reaction can be carried out at even lower concentrations, fluorescence was used as the probe to evaluate the conversion of the protein to the polymer-protein nanoassembly. To this end, green fluorescent protein (GFP, recombinant protein originated from *Aequorea Victoria*) was used as a model protein, as its intrinsic fluorescence can be utilized to monitor the complexation process with fluorescent polarization measurements. Syntheses and characterization of the arylboronic acid-modified GFP and GFP-BA@P1 complex are detailed in the SI. The fluorescent polarization of the GFP and GFP-BA, by themselves, did not show any change with time. On the other hand, as the presumed complex between P1 and GFP-BA should result in a nanoassembly with substantially higher molecular weight, the fluorescent polarization of the complexed GFP should be much higher.

Indeed, it was observed that there is a temporal evolution of the polarization, where there is a sharp increase at ~30 minutes and was complete in ~70 min (FIG. 2d). The reason for the lag time of 30 minutes is not clear to us at this time. It should be noted that the nM concentration of the protein in this experiment is substantially lower than the experiments above, which were characterized by SDS-PAGE. To additionally confirm that the observed increase in polarization is indeed due to the click reaction between the polymer and the protein, the physical mixture of the unmodified GFP and P1 were evaluated, which gratifyingly did not exhibit any change in fluorescence polarization with time (FIG. 2d).

The kinetics experiments above were carried out at the polymer:protein ratio of 10:1. The ideal ratio at which this reaction would be complete was identified. SDS-PAGE of the polymer-protein complexes at different ratios are shown in FIG. 2a. Understandably, the extent of free protein band decreased with increase in the polymer:protein ratio. At 5:1 ratio, there was no discernible free protein in the gel, indicating quantitative complex formation at this ratio. Since the protein is completely encapsulated, no further purification might be needed to remove the free protein. To be more quantitative about the extent of complexation between the polymer and the protein, the boronic acid modified RNaseA was treated with alizarin red S (ARS) dye, which has been previously used for quantifying boronic acid functionalities. (Springsteen, et al. *Chem. Commun.* 2001, 1608-1609.)

Figure 32:
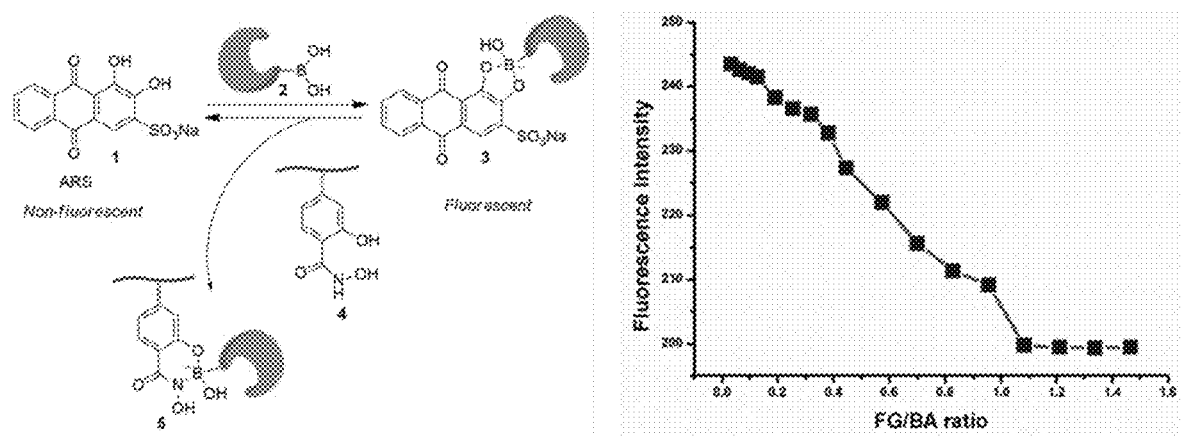
FIG. 32. Fluorescence titration through ARS assay. The left figure is the illustration of the titration process: ARS dye is complexed with boronic acid modified protein at first. Then, the polymer solution was added into the above complex. The result readout was recorded by the decrease of the fluorescence as shown in the right figure.

ARS contains a catechol moiety that complexes to the boronic acid on the protein surface. Then, the extent of complexation between the salicylhydroxamate polymer P1 and these modified proteins can be quantified, since the displacement of the catechol moiety in ARS with the salicylhydroxamate moiety would cause the liberation of the dye from the boronic acid, which can be measured by fluorescence (FIG. 32). It was found that the reaction was complete at the polymer:protein ratio of ~3, as any further increase in the ratio did not produce any change in ARS fluorescence.

Next, the possibility of ROS-responsive release of the encapsulated protein was assessed. Specifically, hydrogen peroxide ($H_2O_2$) was used as the stimulus, as this oxidant has been implicated in many ROS-producing diseases. (Stone, et al. *Antioxid. Redox Signaling* 2006, 8, 243-270; Finkel, et al. *Nature* 2007, 448, 767-774.)

The basis for the disclosed molecular design for traceless protein release is that in the presence of $H_2O_2$, the boronate esters in the complex would be oxidized to the corresponding phenol, which would cause the protein surface to be disconnected from the polymer. The p-hydroxybenzylcarbamate moiety would then rapidly self-immolate through a 1,6-benzyl elimination to liberate the lysines on the surface of the protein as illustrated in Scheme 1. (Wang, et al. *Angew. Chem., Int. Ed.* 2014, 53, 13444-13448; Jourden, et al. *Angew. Chem. Int. Ed.* 2010, 49, 6795-6797; Lux, et al. *J. Am. Chem. Soc.* 2012, 134, 15758-15764; Broaders, et al. *J. Am. Chem. Soc.* 2011, 133, 756-758.)

Figure 3:
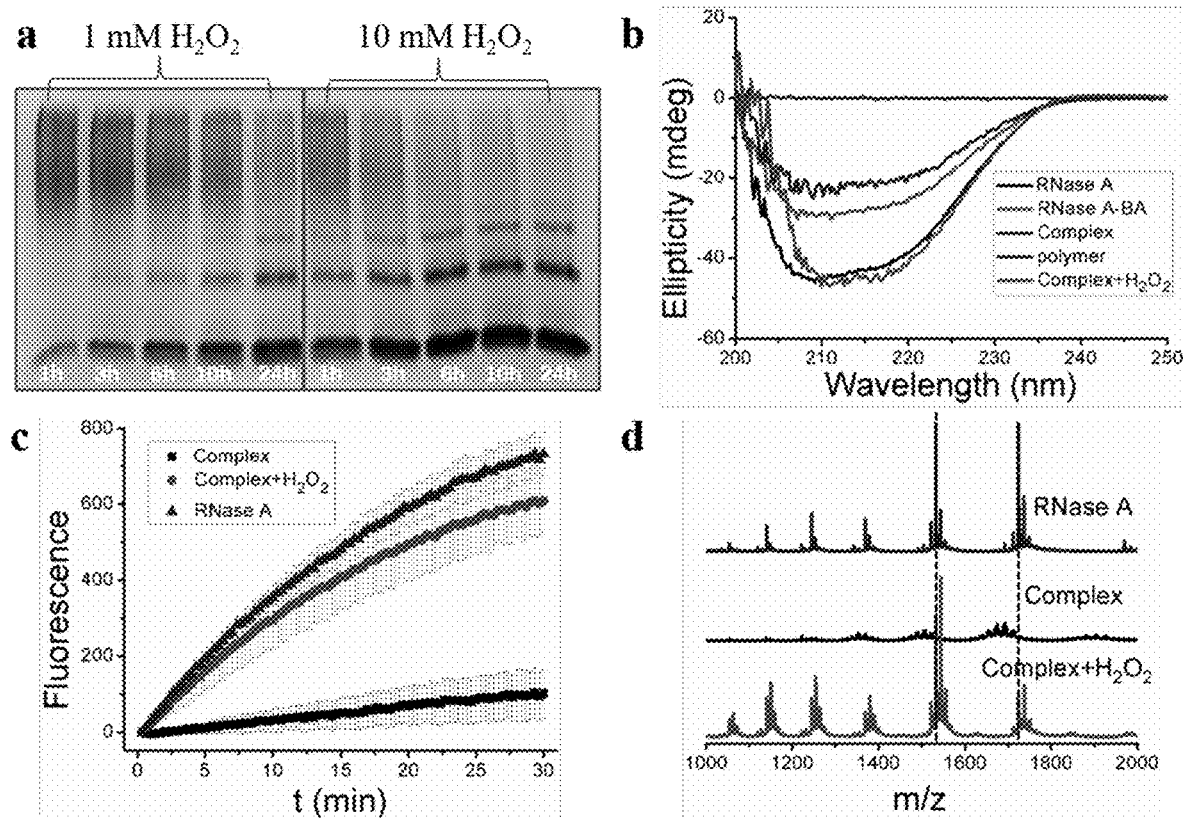
FIG. 3. Traceless release of RNaseA from the polymer-protein complex. a) release kinetics of RNaseA protein from the RNaseA-BA@P1 complex in the presence of 1 mM and 10 mM $H_2O_2$; b) circular dichroism (CD) spectra of the protein, modified protein, the polymer-protein complex, and the polymer-protein complex in the presence of $H_2O_2$; c) activity assay of RNaseA using the commercially available RNaseAlert QC system that shows that while the protein activity is suppressed in the polymer-protein complex, it is recovered in the presence of $H_2O_2$; d) ESI-MS analysis of the protein released from the polymer-protein complex, indicating a traceless protein release process.
Figure 33:
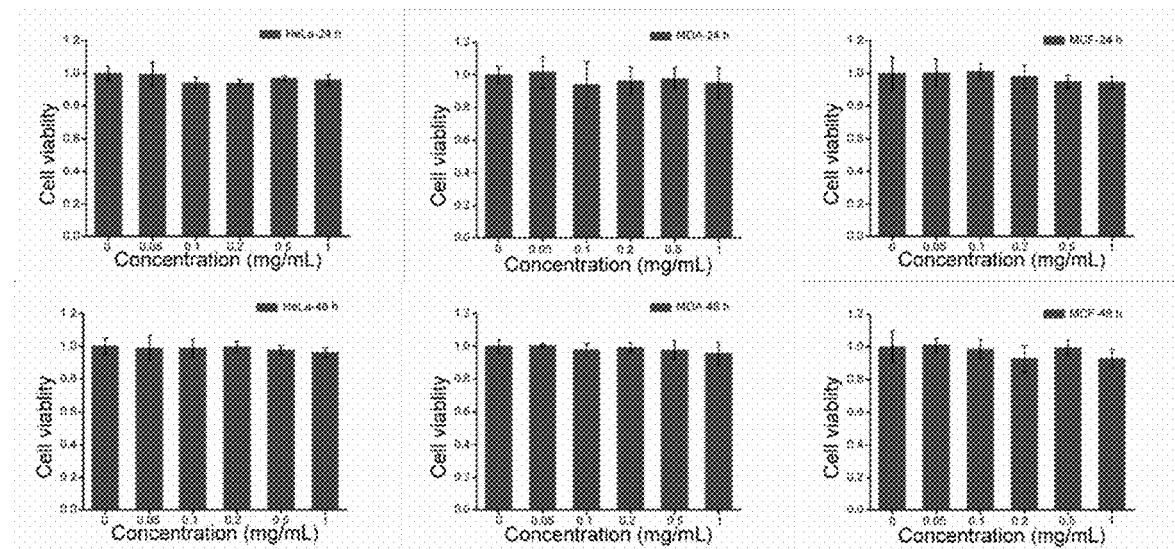
FIG. 33. Polymer toxicity from MTT assay toward different cell lines (HeLa, MDA-MB-231, MCF-7) for different incubation times (24 h and 48 h).

This possibility of protein release was studied under two $H_2O_2$ concentrations (1 mM and 10 mM). The temporal release of the protein was studied over a 24 hours period using gel electrophoresis, as shown in FIG. 3a. Indeed, in both cases the protein release was ascertained by gradual increase in the intensity of the band that corresponds to the free protein. The release kinetics was also found to be dependent on the concentration of the stimulus. Also noted was that the oxidation conditions result in protein dimerization. Further, it was found that the protein release kinetics was independent on the polymer length, as discerned from testing polymer P3 with Mw of 35 kDa for the self-assembly process (FIG. 33).

It is understood that while the SDS-PAGE studies show that the protein is released, this assay does not provide information on the post-release structure or the function of the protein. Structure of the released protein was first analyzed using circular dichroism (CD). Indeed, the intensity and shape of the CD spectrum of the released protein closely matched with that of the pristine RNaseA (FIG. 3b). A small, but discernible, shift in the band at 210 nm was noticed. While this can be attributed to the fact that the released protein contains the polymer, byproducts of the self-immolation reaction, and the oxidant, of interest was testing the fidelity of the process by testing the activity of the released protein. Thus, the released protein was subjected to a well-established fluorogenic assay for RNaseA activity. The released protein retained >90% activity of the pristine protein (FIG. 3c). To further confirm that the protein is indeed released in its traceless form, the released proteins were analyzed using mass spectrometry, as it is sensitive to subtle changes in mass and thus would be the clearest indicator of traceless release. Indeed, the released protein exhibited the same mass as the pristine RNase A (FIG. 3d).

Figure 34:
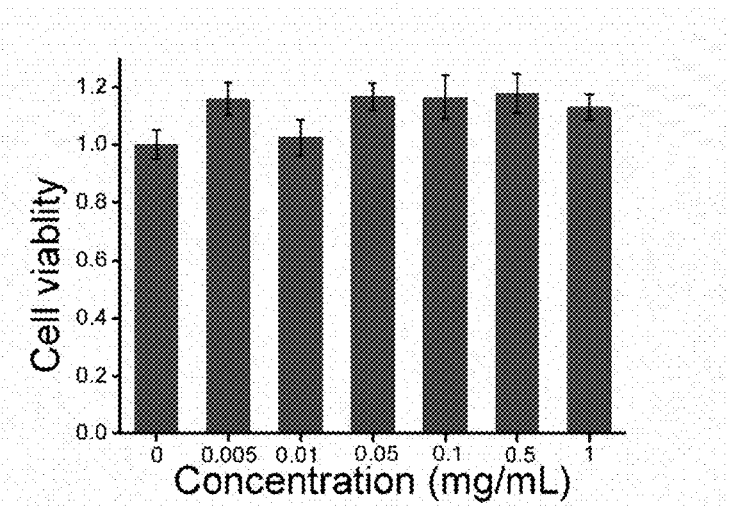
FIG. 34. Polymer toxicity from Alamar blue assay toward HeLa cell line after 24 h incubation.
Figure 35:
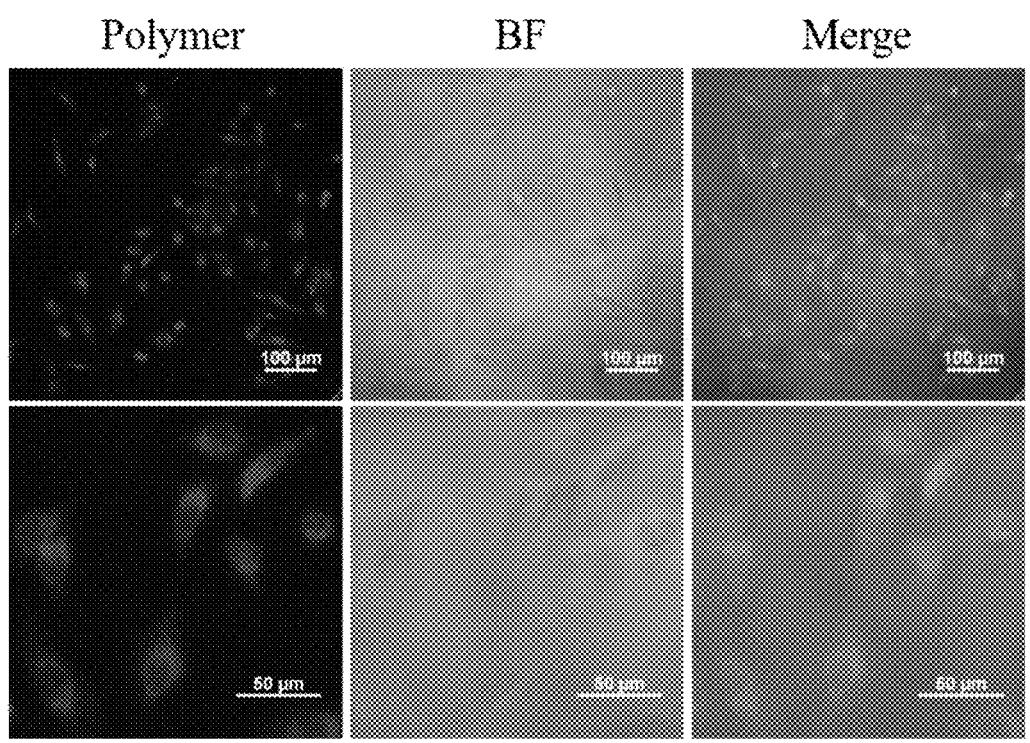
FIG. 35. Cell uptake of Rhodamine B labelled polymer (0.3 mg/mL) with CLSM imaging at different magnifications. (HeLa cell, 4 h incubation)
Figure 36:
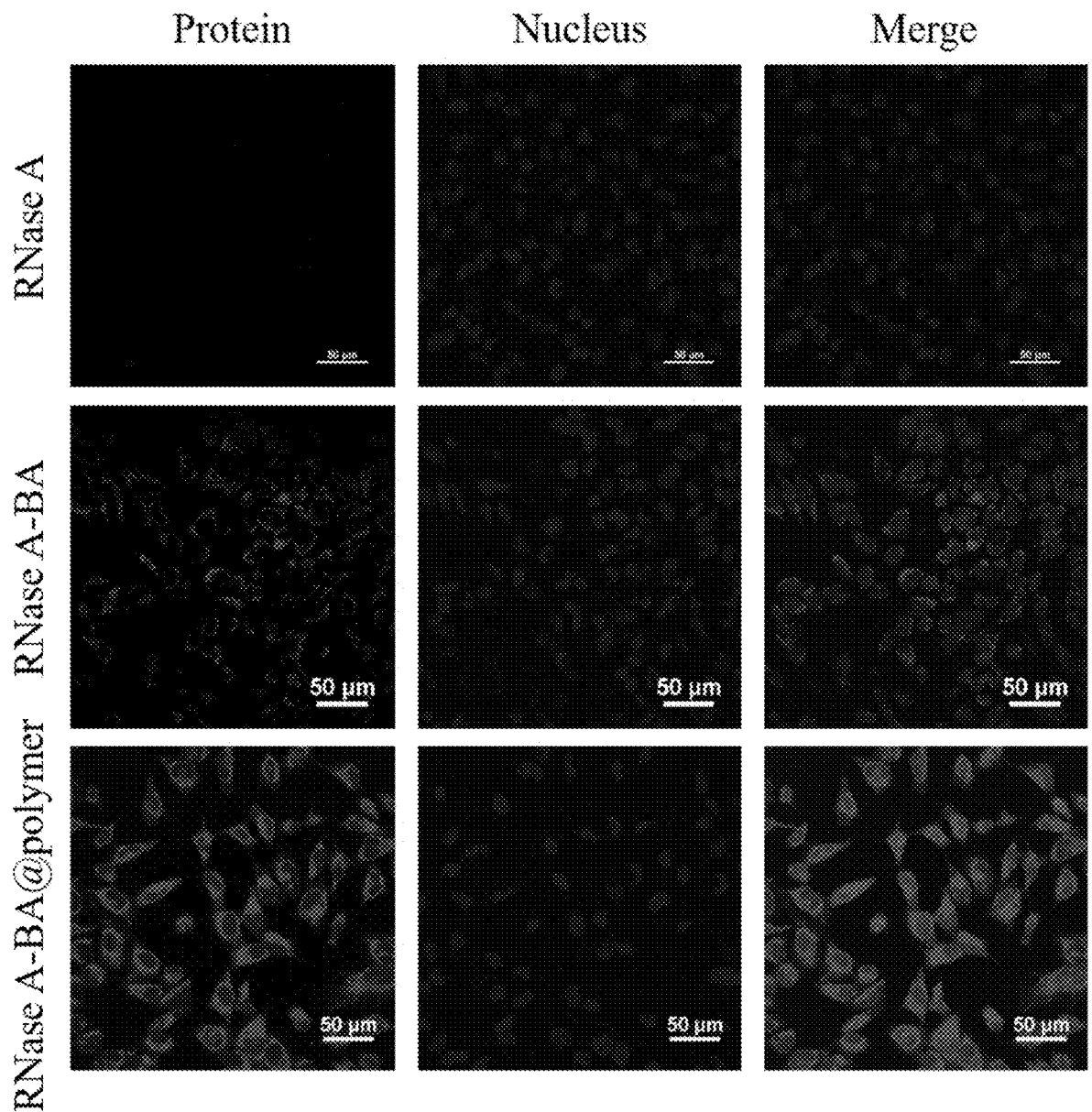
FIG. 36. Cell uptake of RNaseA, RNaseA-BA, and RNaseA-BA@polymer at the same protein concentration (30 μg/mL). (HeLa cell line, 4 h incubation)

One of the goals here is to utilize this self-assembly approach to traffic globular proteins across the cellular membrane, as the use of the polymer sheath to mask the proteins, gain access to the cellular interior, and tracelessly release the protein cargo inside the cytosol in its functionally active form. Prior to testing this possibility, it was needed to test whether the polymer exhibits any cytotoxicity. To this end, the toxicity of the polymer P1 was tested using the Alamar blue assay and MTT assay; the polymer P1 did not exhibit any toxicity toward different cell lines (HeLa, MDA-MB-231, MCF-7) after different incubation times, even at 1.0 mg/mL concentration (FIGS. 34 and 35). To ensure that the polymer is indeed gaining access into the cells and is still non-toxic, the polymer was labeled with a small percentage (~1%) of a fluorophore, rhodamine B, to generate polymer P2. When the cells were incubated with this labeled polymer for the same amount of time, the cellular uptake was found to be significantly high (FIG. 36). Overall, these results show that the polymer itself is non-toxic and thus can be used for intracellular protein delivery experiments.

Figure 37:
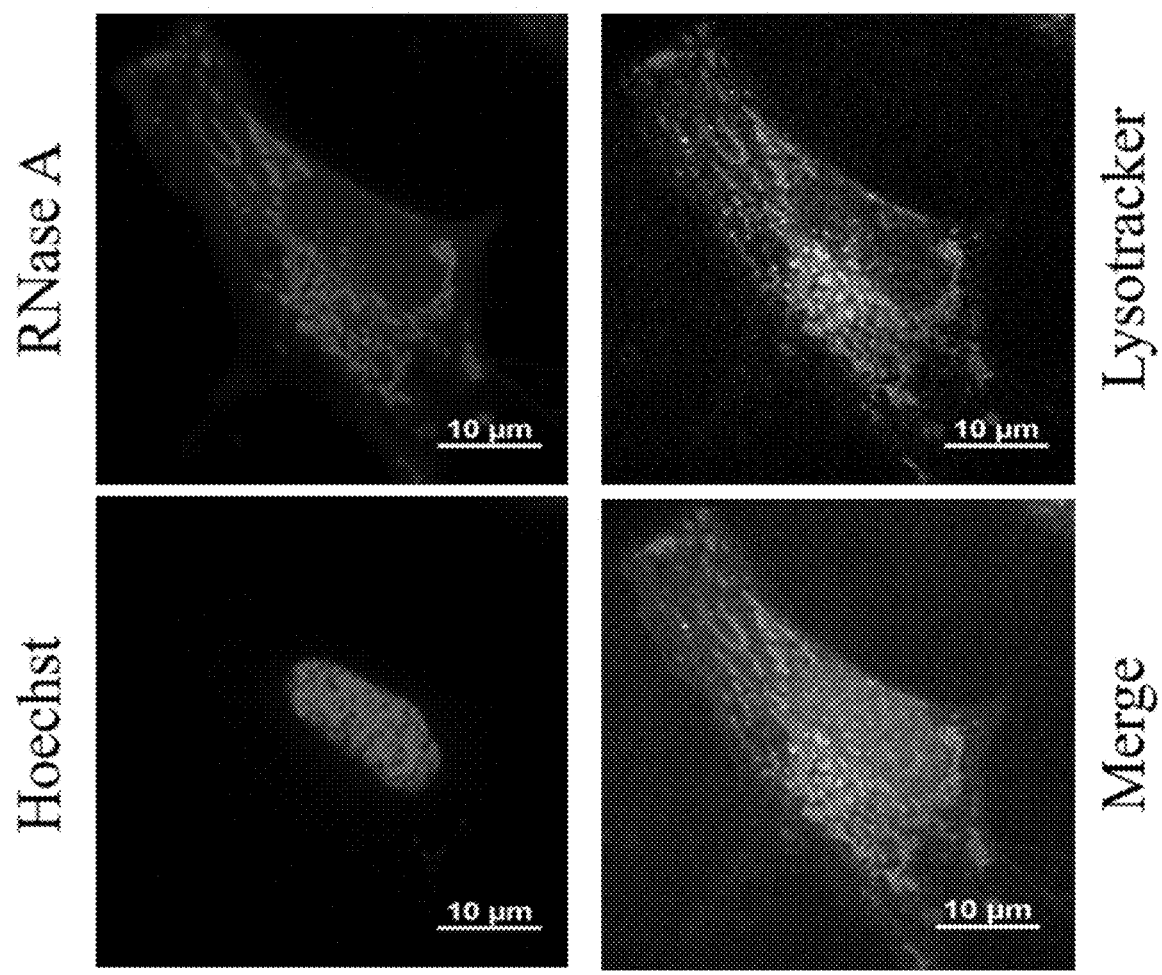
FIG. 37. Confocal imaging of cell uptake of RNaseA complex (protein concentration: 30 μg/mL) after 4 h incubation.

The possibility of intracellular delivery of proteins was tested using RNaseA as the protein in HeLa cells. Since the focus was mainly on the location of the protein in the experiments here, RNase A-BA was fluorescently labeled with rhodamine B. Upon incubating the polymer-protein conjugate with cells, the intracellular uptake was tracked using confocal laser scanning microscopy (CLSM) at different times. Concurrently, the nucleus of the cells was labeled with Hoechst 33342. After just 4 h, a well-distributed fluorescence from the labeled proteins was observed (FIG. 4a and FIG. 37), while negligible fluorescence was observed from cells that were treated with an identical concentration of naked proteins (FIG. 37). Interestingly, RNaseA-BA itself did exhibit some uptake, which is attributed to the possibility that boronic acid moieties can interact with the cell membrane to facilitate cellular uptake. (Ellis, et al. *J. Am. Chem. Soc.* 2012, 134, 3631-3634.) Nonetheless, the efficiency of this process was much lower than that of the RNaseA@P1 complex.

Figure 38:
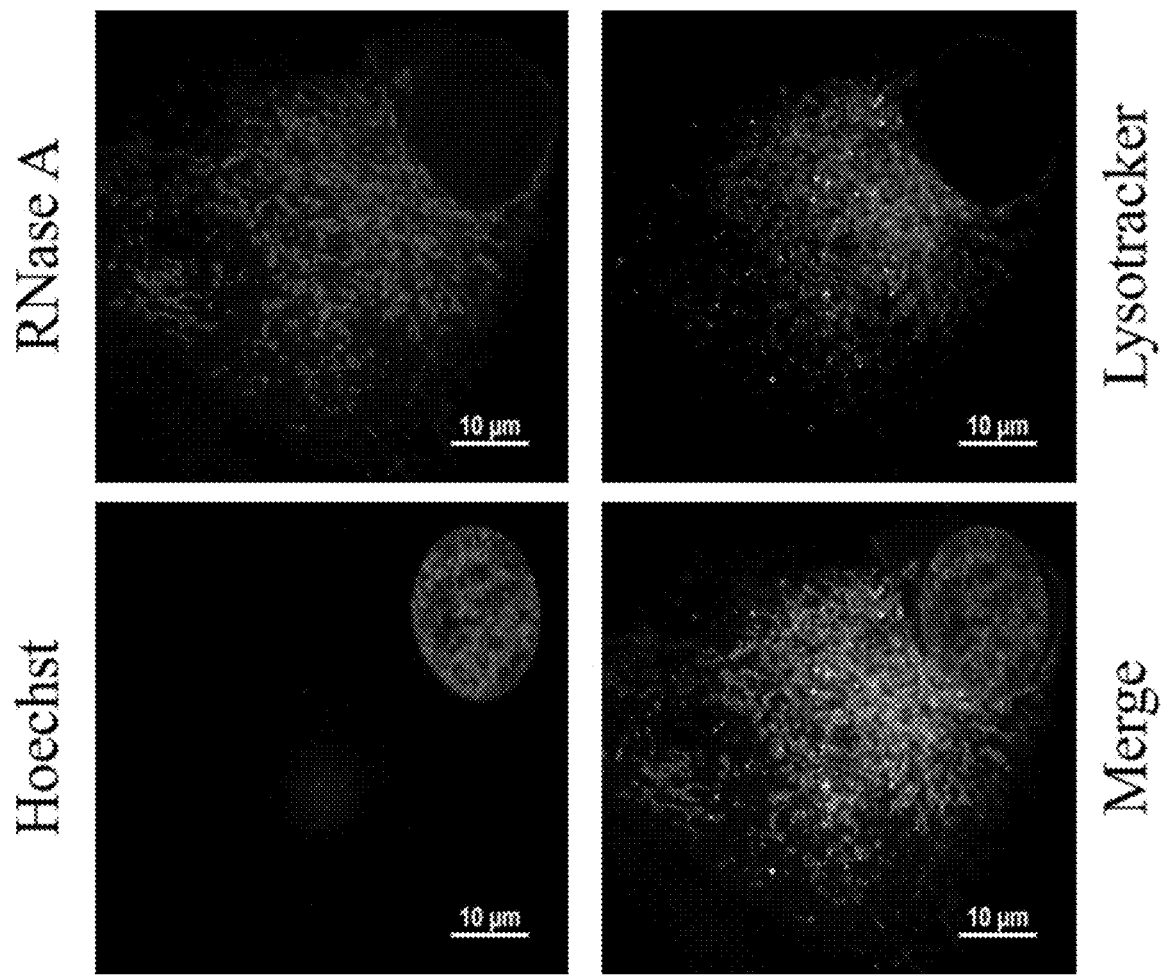
FIG. 38. Confocal imaging of cell uptake of RNaseA complex (protein concentration: 30 μg/mL) after 24 h incubation.
Figure 39:
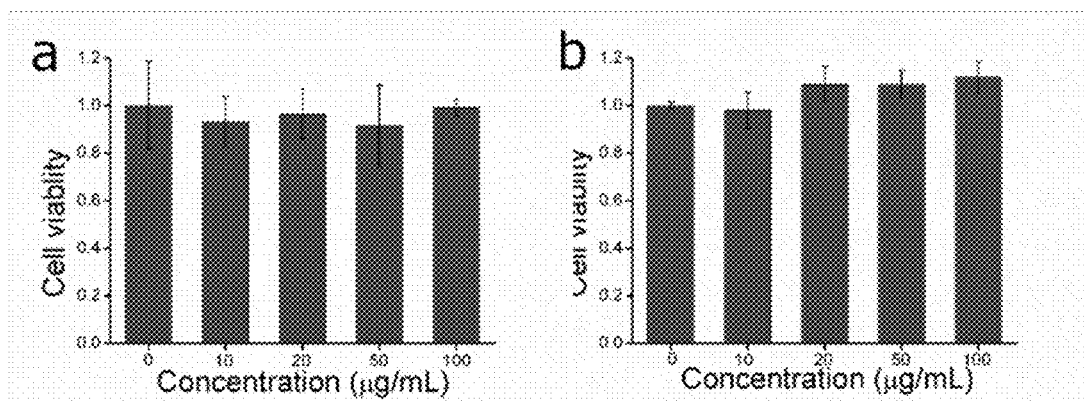
FIG. 39. Cytotoxicity (HeLa cell) study (MTT assay) after 48 h incubation. a) RNaseA-BA, b) RNaseA-BA@polymer.

It is also important to test whether the protein is in the cytosol. Because most nanoassemblies are thought to access cells through an endocytosis process, which means that the nanoassembly needs to escape the endosome in order to access the cytosol. Note that RNaseA is effective in its function, only in the cytosol. Therefore, the endosomes were incubated with lysotracker green (FIG. 38-39). The initial colocalization of green and red fluorescence did indicate that the nanoassemblies enter the cells through the endosomes, as indicated by the fluorescence image at the 4 h timeframe (FIG. 4b and FIG. 38). Interestingly however, the proteins do escape the endosomes over time, as seen by the distinct red color in the cells after 24 h (FIG. 4b and FIG. 39). The mechanism for endosomal escape is not clear to us at this time.

Figure 4:
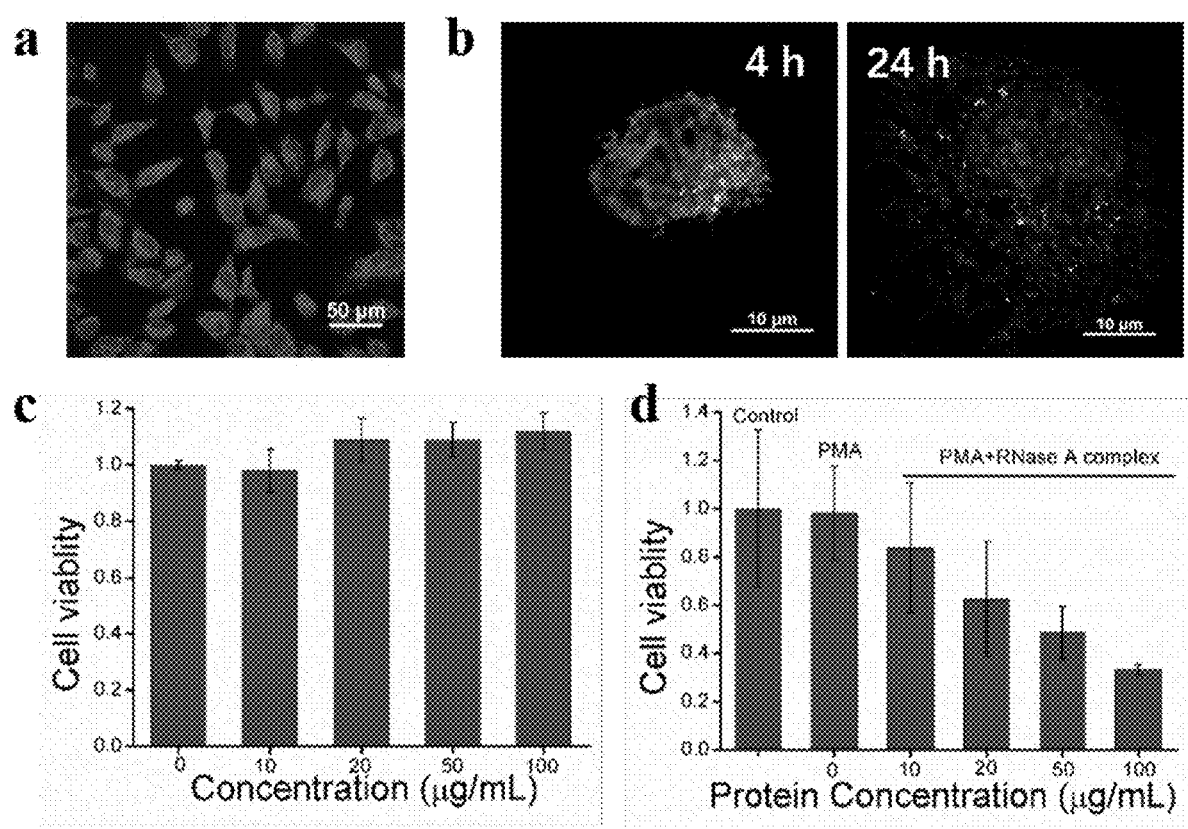
FIG. 4. Cellular uptake of the polymer-protein conjugate and ROS-responsive protein release. a) confocal microscopy image of HeLa cells incubated with the polymer-protein complex for 4 h, where the protein is labeled with a fluorophore (red color represents rhodamine b labeled RNase A, blue color represents hochest 33342 dye labeled nucleus); b) temporal evolution of co-localization of lysotracker (green) and the fluorescently-labeled protein (red) indicating endosome escape in cells (nucleus were labeled by hochest 33342 dye with blue color); c) cytotoxicity of RNaseA the protein by itself after 48 h incubation, which indicates that RNaseA does not have access to the cytosol of cells; d) cytotoxicity of RNaseA-BA@polymer after incubation with 200 nM of PMA to introduce oxidative stress (after 48 h), where the dose-dependent cytotoxicity shows protein release and activity inside cells.
Figure 40:
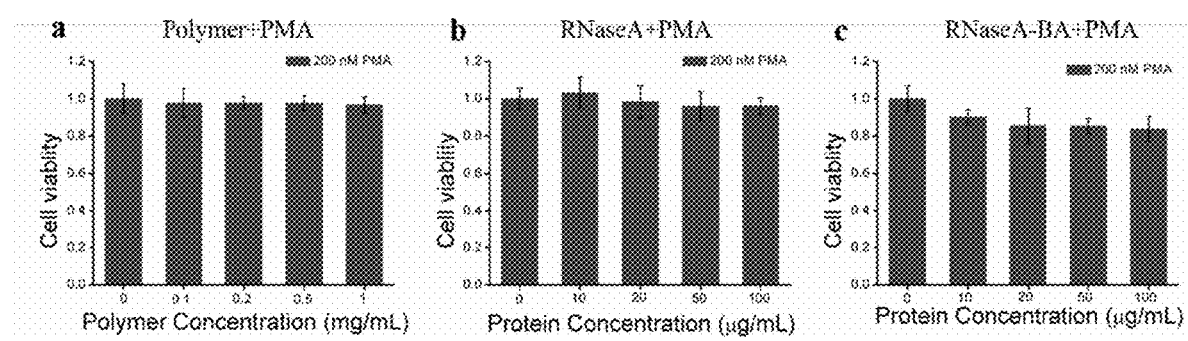
FIG. 40. Cytotoxicity (HeLa cell) study (MTT assay) in the presence of 200 nM PMA after 48 h incubation. a) Polymer P1, b) RNaseA, c) RNaseA-BA.

If the protein cargo does indeed end up in the cytosol, then the delivered RNaseA should be functional inside the cells. RNaseA, cleaves RNA molecules inside cells to induce apoptosis. This possibility of cellular apoptosis, after incubation with protein-containing nanoassemblies, was studied. Interestingly, none of the RNaseA-based formulations (bare RNaseA, RNaseA-BA and RNaseA-BA@polymer) exhibited any sign of cellular apoptosis (FIG. 4 and FIG. 40). This could be because the conjugation of the protein with the polymer causes the former to lose its activity and that the protein has not been liberated from the polymer inside the cells. This is understandable, because these nanoassemblies are programmed to liberate the protein in the presence of $H_2O_2$ as the ROS stimulus and the native ROS concentration of the HeLa cell might not be sufficient. To test this idea, cells with 200 nM concentration of phorbol-12-myristate-13-acetate (PMA) were incubated, as this molecule is known to induce ROS generation inside cells. (Kuwabara, et al. *PLoS One* 2015, 10, e0116410.)

Figure 41:
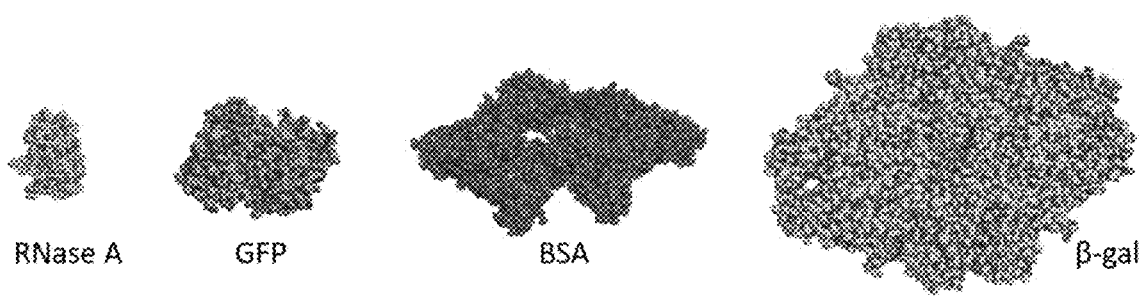
FIG. 41. Size comparison of different proteins used in this work. The PDB codes for protein structures were-RNase A: 5rsa; GFP: 1 gfl; BSA: 3v03; β-gal: 1jz8.

Now, the RNaseA-BA@P1 exhibited a clear dosage-dependent cellular toxicity, indicating that the protein is indeed causing cellular apoptosis. To further check that this is a manifestation of the polymer-protein conjugate, the cells were incubated with RNaseA, RNaseA-BA, and the polymer (each by itself) in the presence of 200 nM PMA and none of these combinations exhibited any cellular toxicity (FIG. 41).

Following the demonstration of the polymer-protein self-assembly, stimulus-induced protein release in its traceless form, and the retention of protein function including in cells, the versatility and generality of the approach were tested even further. To this end, the potential was tested for delivering proteins of different sizes and to different cell lines. Also of interest was testing the generality of the molecular design for responsive release with other stimuli.

Figure 42:
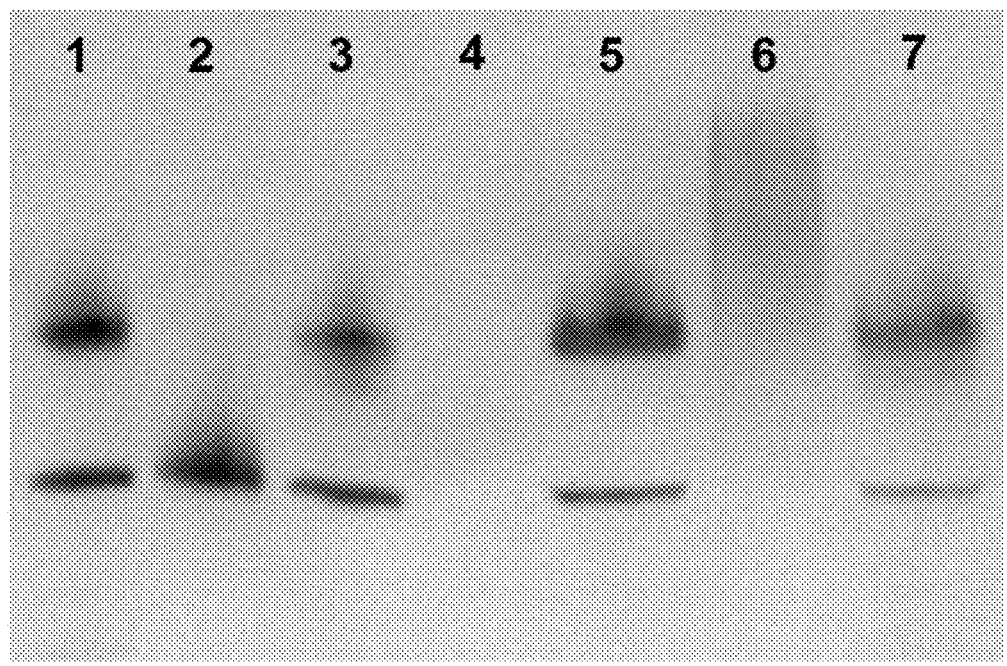
FIG. 42. SDS-PAGE gel for GFP complexation. Lane 1. GFP; Lane 2. GFP-BA; Lane 3. GFP-BA+$H_2O_2$ (10 mM), Lane 4. Polymer P1; Lane 5. GFP+polymer (1:10); Lane 6. GFP-BA+polymer (1:10); Lane 7. GFP-BA@polymer+$H_2O_2$ (10 mM concentration).
Figure 43:
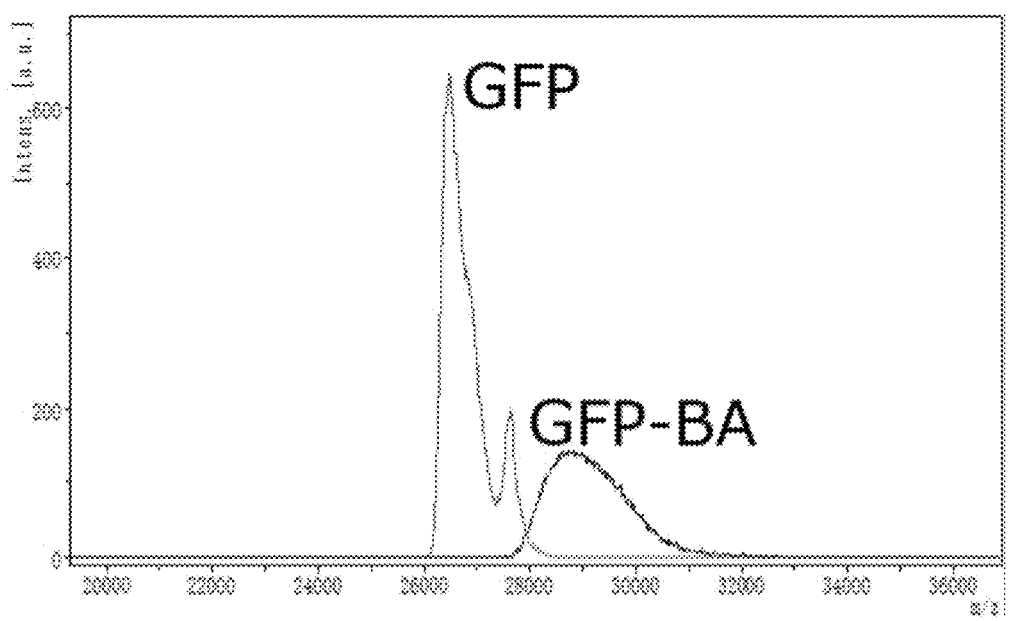
FIG. 43. MALDI-MS for GFP before and after boronic acid linker modification. The average Mw for GFP and GFP-BA are 26900 and 28793 Da. Based on the calculation, the average modification amount is 11.
Figure 44:
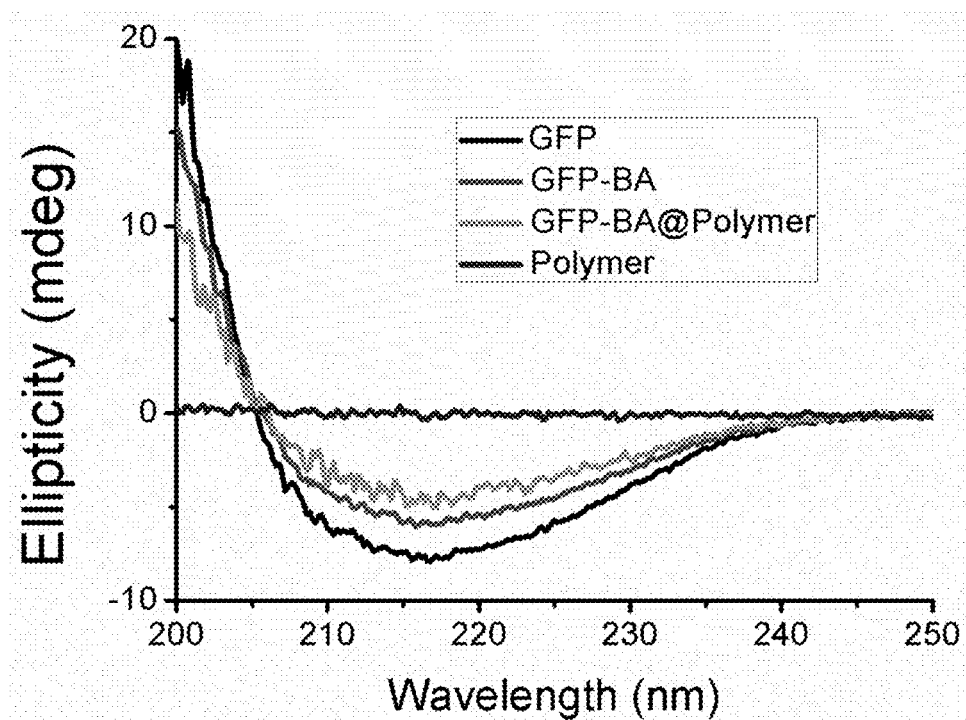
FIG. 44. CD spectra for GFP and related complex (including the protein, modified protein, the polymer-protein complex, and the polymer as control).
Figure 45:
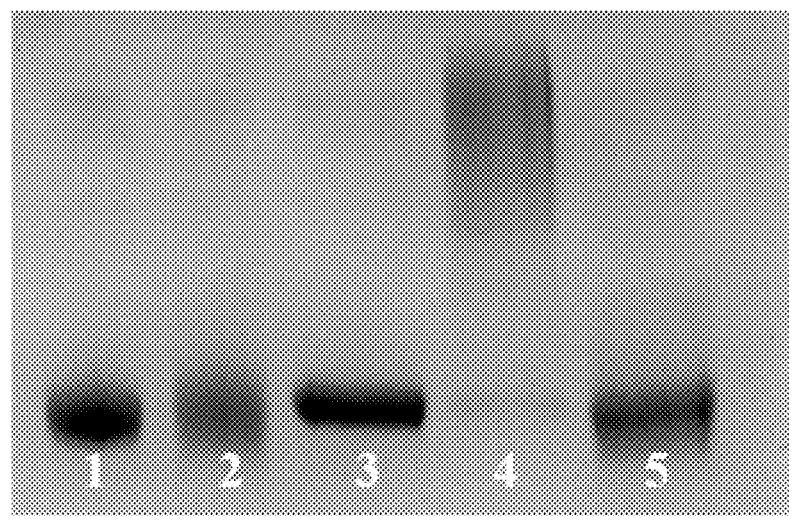
FIG. 45. Gel for BSA and related complex. Lane 1, BSA; Lane 2, BSA-BA; Lane 3, BSA-BA+$H_2O_2$(1 mM concentration); Lane 4, BSA-BA@polymer; Lane 5, BSA-BA@polymer+$H_2O_2$(1 mM concentration).
Figure 46:
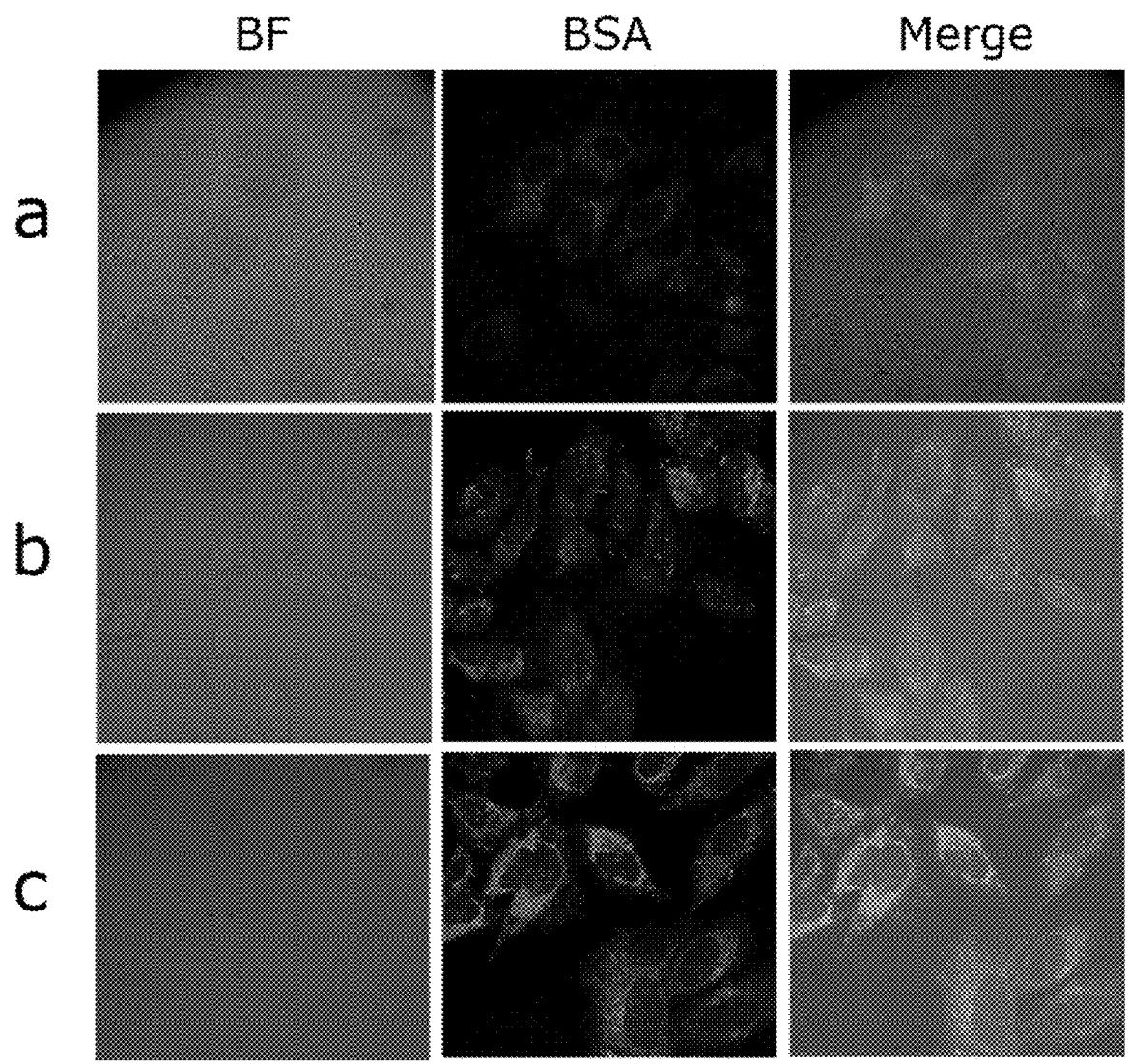
FIG. 46. Concentration dependent cell uptake of BSA-BA@polymer (at 1:10 ratio) complex (HeLa cell line, 4 h incubation). Protein concentrations: a) 12.5 μg/mL, b) 50 μg/mL, c) 100 μg/mL. BSA was labelled with rhodamine B.
Figure 47:
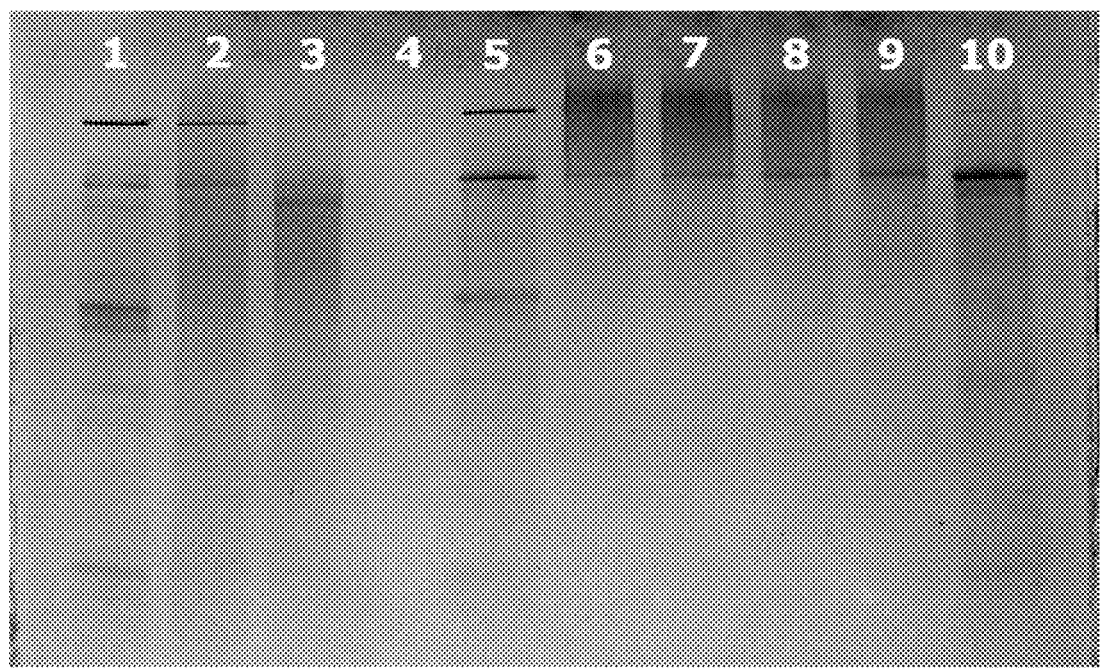
FIG. 47. Gel for β-Gal complexation and release process. 1, β-gal; 2, β-gal-BA; 3, β-gal-BA+$H_2O_2$; 4, Polymer P1; 5, β-gal+Polymer; 6-9, β-gal-BA&Polymer (1:1; 1:2; 1:5; 1:10); 10, 8+$H_2O_2$ (10 mM).
Figure 48:
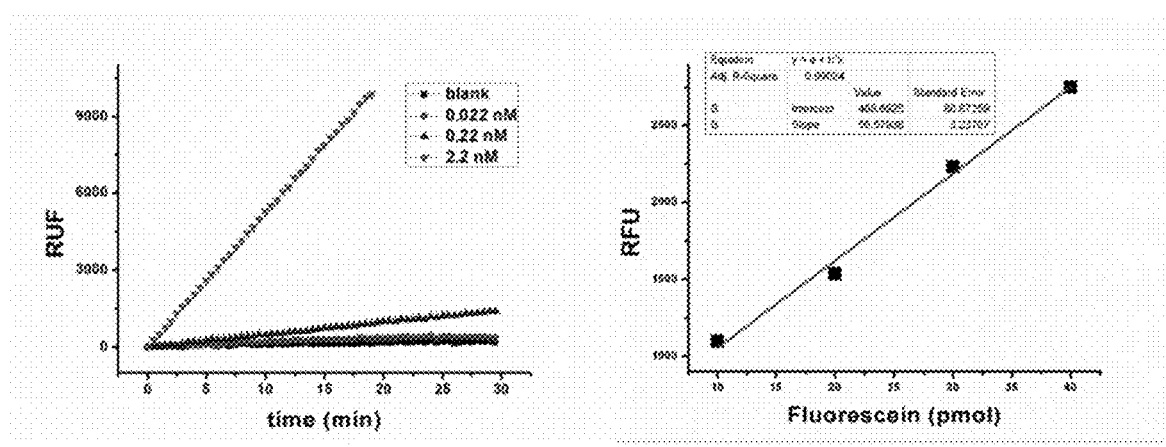
FIG. 48. Standard curve for β-Gal activity assay.
Figure 49:
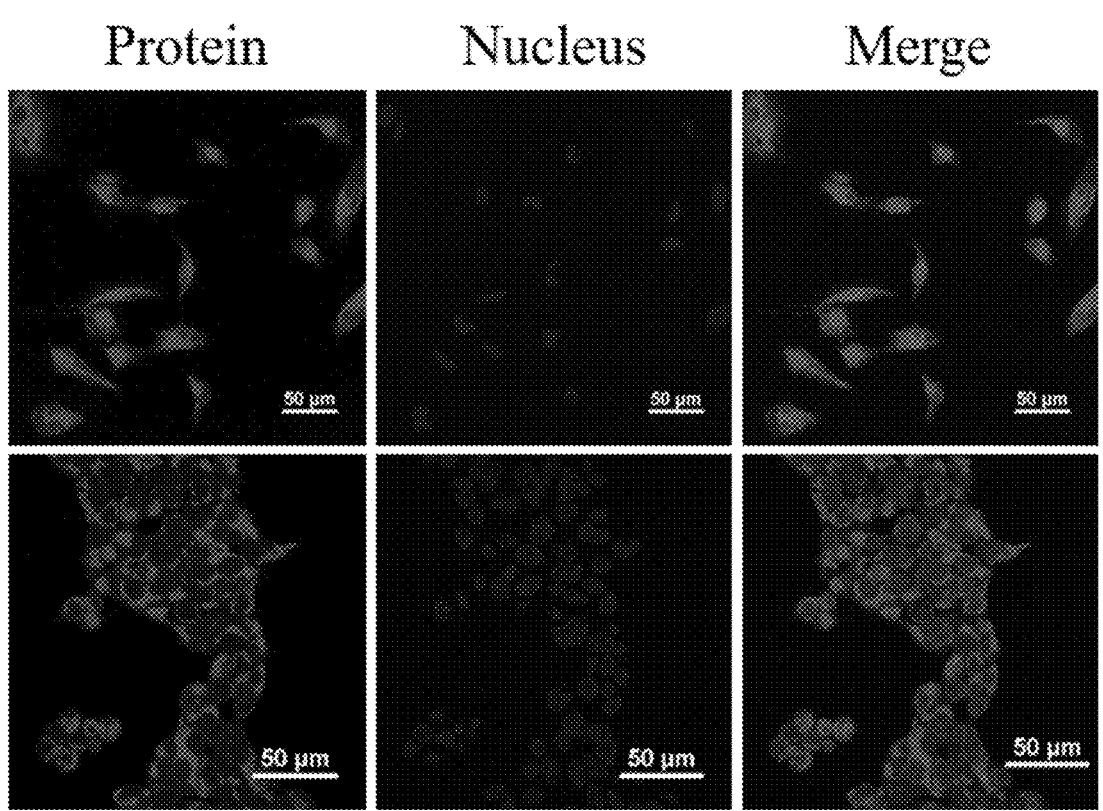
FIG. 49. Cell line variations in the cellular uptake using polymer-protein conjugates. a) confocal microscopy image of MDA-MB-231 cells incubated with RNaseA-BA@polymer complex for 4 h; b) confocal microscopy image of MCF-7 cells incubated with RNaseA-BA@polymer complex for 4 h.

RNase A is a small protein with MW of 14 kDa and an isoelectric point (pI) of 8.9. The latter feature indicates that the protein is basic, i.e., there is a relatively high number of lysine units, which were used as the handle for conjugating the proteins with the polymer. To further test the scope of this approach, the proteins chosen were not only of different sizes, but also that are in general considered to be more acidic (Table 1 and FIG. 42). Thus, three other proteins were chosen, viz., green fluorescent protein (GFP, 27 kDa, pI 5.7), bovine serum albumin (BSA, 66 kDa, pI 5.8) and β-galactosidase (β-gal, 484 kDa (tetramer MW), pI 5.3, from *Escherichia coli*). Similar to the strategy used with RNaseA, the surface lysines of these proteins were initially modified with 1 to convert these to the corresponding boronic acid moieties. These modified proteins were then treated with P1, as with RNaseA-BA, to obtain the polymer-protein conjugate (FIG. 43-49).

TABLE 1

Protein information summary

| Protein | $M_n$ | Lys (#) | PI |
|---|---|---|---|
| RNaseA | ~13,700 (150 AA) | 11 | 8.93 |
| GFP | 26,900 (238 AA) | 20 | 5.67 |
| BSA | ~66,000 (607 AA) | 60 | 5.82 |
| Beta-gal | 116,483 (1,024 AA) 464,000 (homo-tetramer) | 20 | 5.28 |

Figure 5:
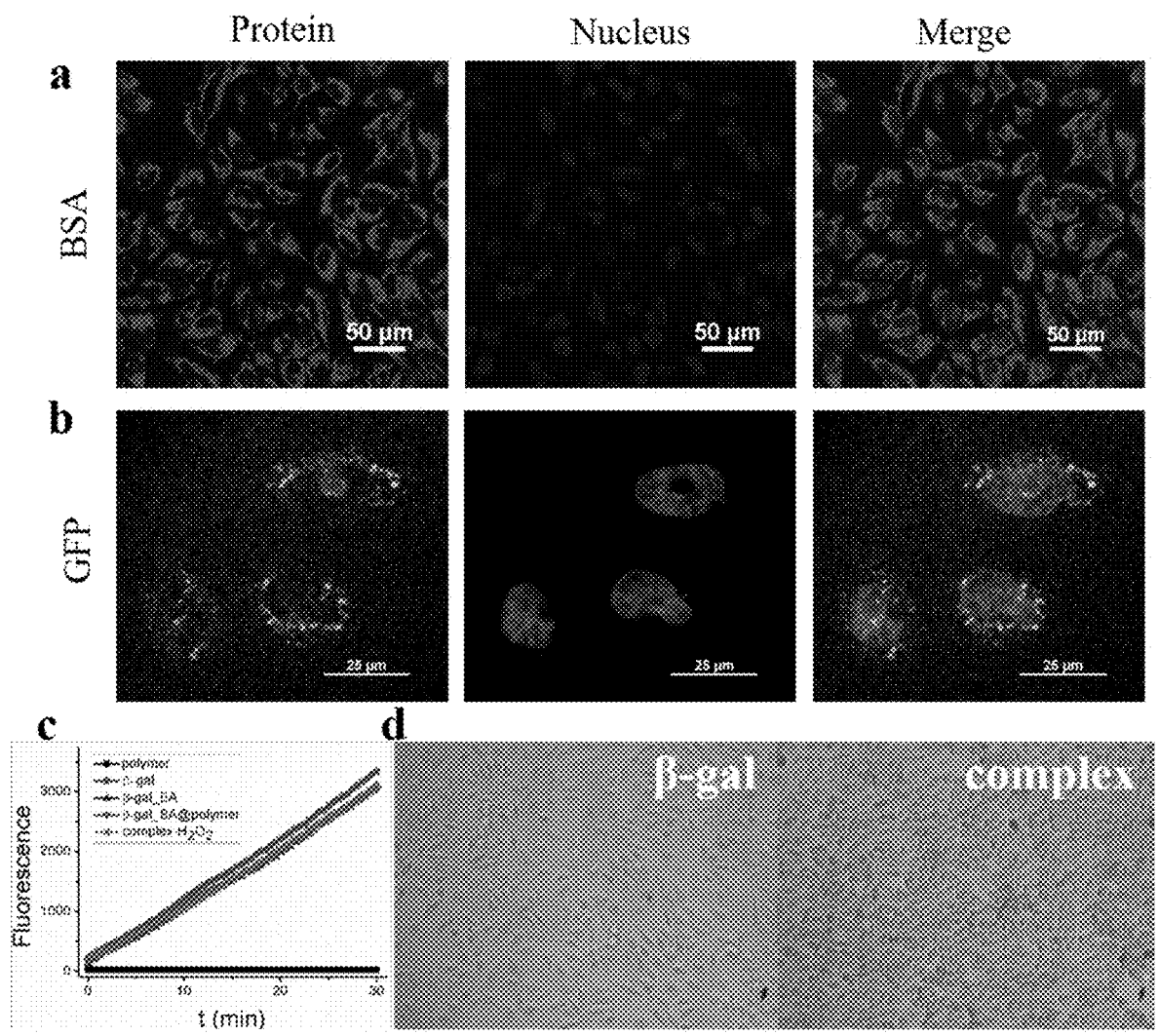
FIG. 5. Protein variations in the polymer-protein conjugates and their cellular uptake. a) confocal microscopy image of HeLa cells incubated with BSA-BA@polymer complex for 4 h, where the protein is labeled with a fluorophore; b) confocal microscopy image of HeLa cells incubated with GFP-BA@polymer complex for 4 h; c) enzyme activity assays of β-gal, β-gal-BA@polymer complex in the absence and presence of $H_2O_2$, which indicate that the protein is not deactivated upon complexation; d) X-gal cellular assay for β-gal protein and the β-gal-BA@polymer complex, showing that the complex is essential for the cellular uptake.

These conjugates were initially characterized for their cellular uptake. The inherent fluorescence of GFP was used as the cellular uptake readout, while BSA was labeled with rhodamine B to track the polymer-protein conjugate in cells. As shown in FIG. 5, both GFP-BA@P1 and BSA-BA@P1 exhibited excellent cellular uptake. Since both these proteins do not have a functional assay, the fate of the polymer-protein conjugate further inside the cells was not probed. On the other hand, β-gal activity can be readily assessed with the X-gal assay.

Interestingly, the polymer conjugation did not result in any loss of β-gal function (FIG. 5c). Note that while the conjugation of the polymer to the protein could result in loss of activity, as with RNaseA, possibly due to restricted protein mobility, it is not obvious that all proteins would lose activity because of the conjugation process. Therefore, it is not surprising that β-gal did not lose its activity upon conjugation. This feature also allowed us to probe a possibility, when delivering these conjugates inside the cells; i.e., this polymer-protein should not require activation by $H_2O_2$ in order to exhibit its activity. However, the fact that the protein is conjugated to the polymer should allow it to be taken up by the cells.

To test this idea, β-gal-BA@P1 was incubated with HeLa cells and assayed the activity of β-gal after 24 hours. The blue color of the cells showed that there is significant β-gal activity in the cells. In the control experiment, where the cells were incubated with the β-gal protein by itself, there was no discernible activity of the enzyme inside the cells (FIG. 5d). Overall, these experiments indicate that the disclosed protein conjugation and delivery strategy is broadly applicable to proteins of different sizes.

Figure 50:
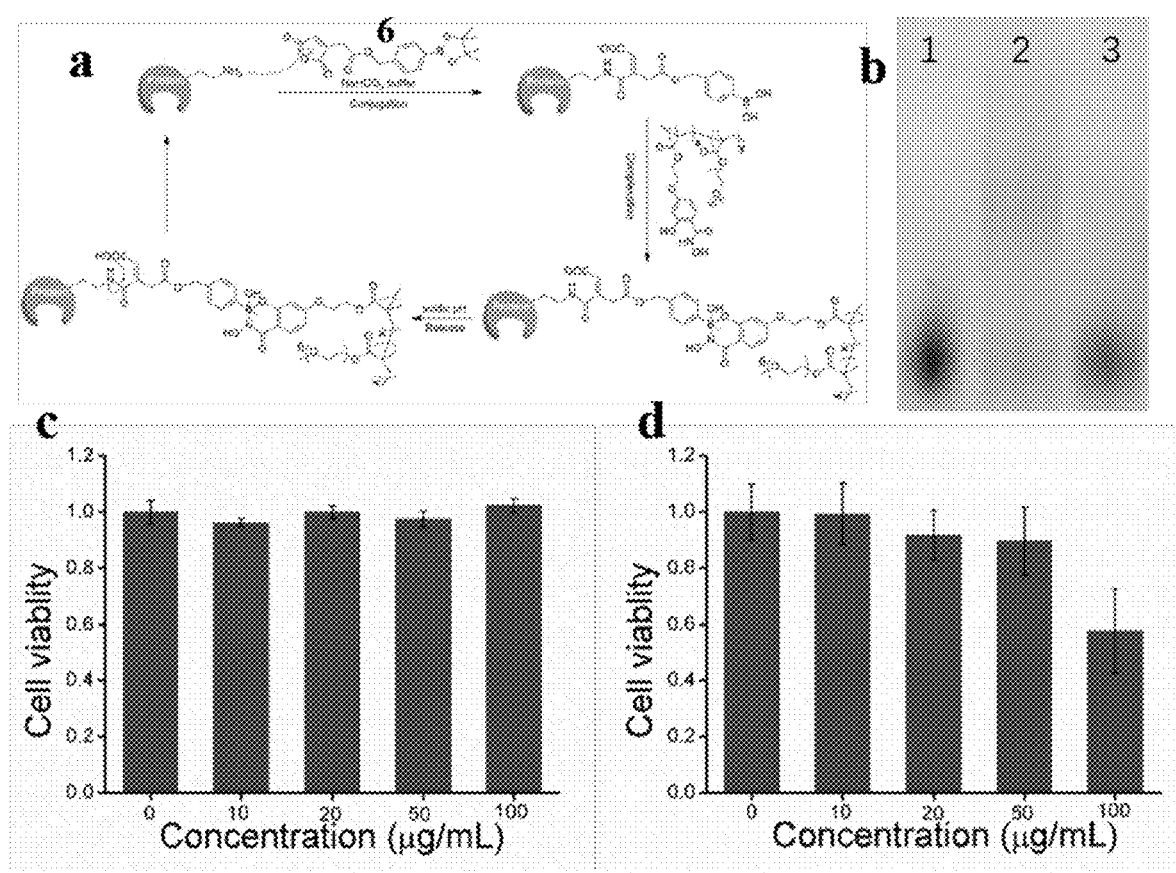
FIG. 50. Formation of the polymer-protein conjugate with the cis-aconityl linker and pH-responsive protein release. a)

Similarly, cellular uptake experiments were carried out using labeled proteins in two other cancer cell lines, viz. MDA-MB-231 and MCF-7. The cellular uptake was found to be very high in both these cases (FIG. 50), indicating that the strategy is applicable to other cell lines as well. Note also that these cellular uptake studies are being carried out without the incorporation of any surface ligand, relying on passive uptake. Opportunities do exist for cellular targeting through ligand incorporation for activated cellular uptake.

Since the salicylhydroxamate-boronic acid-based conjugate offers the opportunity for protein release only in the presence of ROS stimulus even inside cells, of interest was exploring the potential for expanding this approach to other stimuli, while still taking advantage of the very fast click reaction kinetics. Two other stimuli were targeted for this purpose; to utilize the inherently reducing conditions of the cytosol and to utilize the lower pH of cellular microenvironments such as in cancer cells and in endosomal/lysosomal compartments. (Ventura, et al. *Biomacromolecules* 2015, 16, 3161-3171; Liu, et al. *J. Am. Chem. Soc.* 2017, 139, 2306-2317; Casey, et al. *Nat. Rev. Mol. Cell Biol.* 2010, 11, 50-61; Webb, et al. *Nat. Rev. Cancer* 2011, 11, 671-677.)

In both of these cases, an appropriate functional group was introduced between the lysine moiety of the protein and the boronic acid functionality such that the specific stimulus-induced degradation of a functional group would result in the regeneration of the lysine unit.

First focused was on developing a system that would release the protein in response to lower pH at specific microenvironments. The pH-sensitive cis-aconityl linker was introduced between the lysine and the boronic acid moiety. (Lee, et al. *Angew. Chem., Int. Ed.* 2009, 48, 5309-5312.)

Accordingly, RNaseA lysines were modified with the linker 6, shown in FIG. 51. Following the modification, as with the methods outlined above, the protein was treated with P1 to generate the conjugate. When this conjugate was subjected to lower pH for a period of time, the protein was liberated from the nanoassembly as discerned by the SDS-PAGE studies. Similar to the ROS-induced release studies above, this conjugate was also incubated with cells. Compared to the controls, the conjugate indeed exhibited cellular apoptosis; but, the cellular toxicity here was found to be lower than that observed with the ROS-responsive system. This is understandable, because the protein in this case is likely to be partially or fully cleaved from the polymer in the endosome. The extent of endosomal escape for the protein by itself might be low, which is attributed to the lower cell kill.

Next targeted was a system that would respond to the reducing environment of the cells, where the linker would be processed in the cytosol instead of the endosome. To be responsive to the reducing environment, offered by higher intracellular glutathione concentrations, a disulfide linker was introduced at the β-position relative to the carbamate moiety. Reduction based cleavage and subsequent generation of a thiol moiety causes an intramolecular nucleophilic attack on the carbamate moiety to liberate the lysine unit. (Riber, et al. *Adv. Healthcare Mater.* 2015, 4, 1887-1890.)

Figure 6:
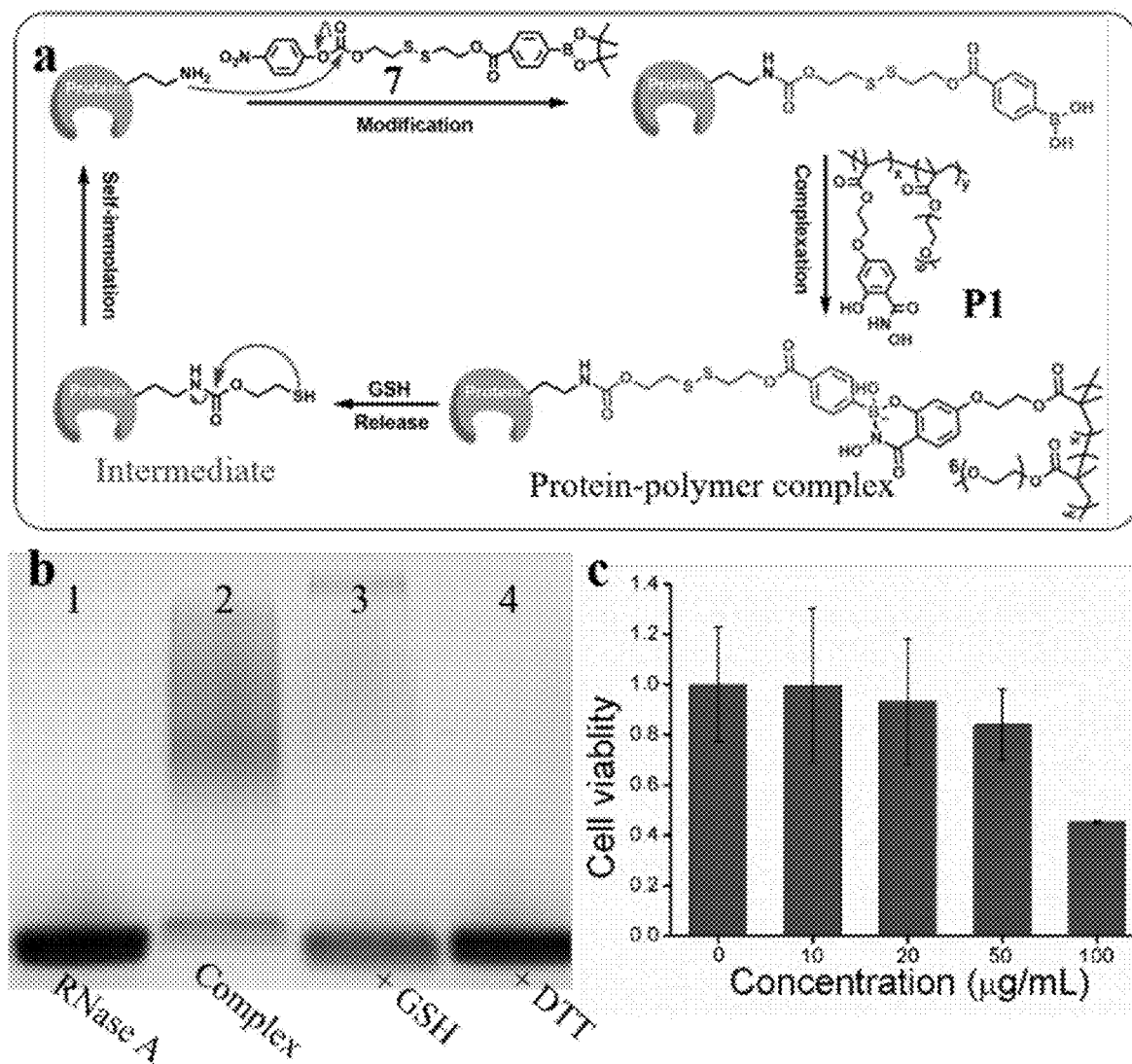
FIG. 6. Formation of the polymer-protein conjugate with a disulfide linker and thiol-responsive protein release. a) modification of lysine surface functional groups in proteins with boronic acid with a self-immolative reduction-sensitive linker, where reducing agents such as DTT and GSH would result in traceless protein release; b) SDS-PAGE gel data, illustrating the complexation and stimulus-induced disassembly of the complex (lane 1: RNaseA-SS-BA; lane 2: complex, lane 3: complex after incubation 10 mM concentration of GSH; lane 3: complex after incubation 10 mM concentration of DTT); c) cytotoxicity of the reduction-sensitive RNaseA-polymer complex after incubation with HeLa cells.
Figure 7:
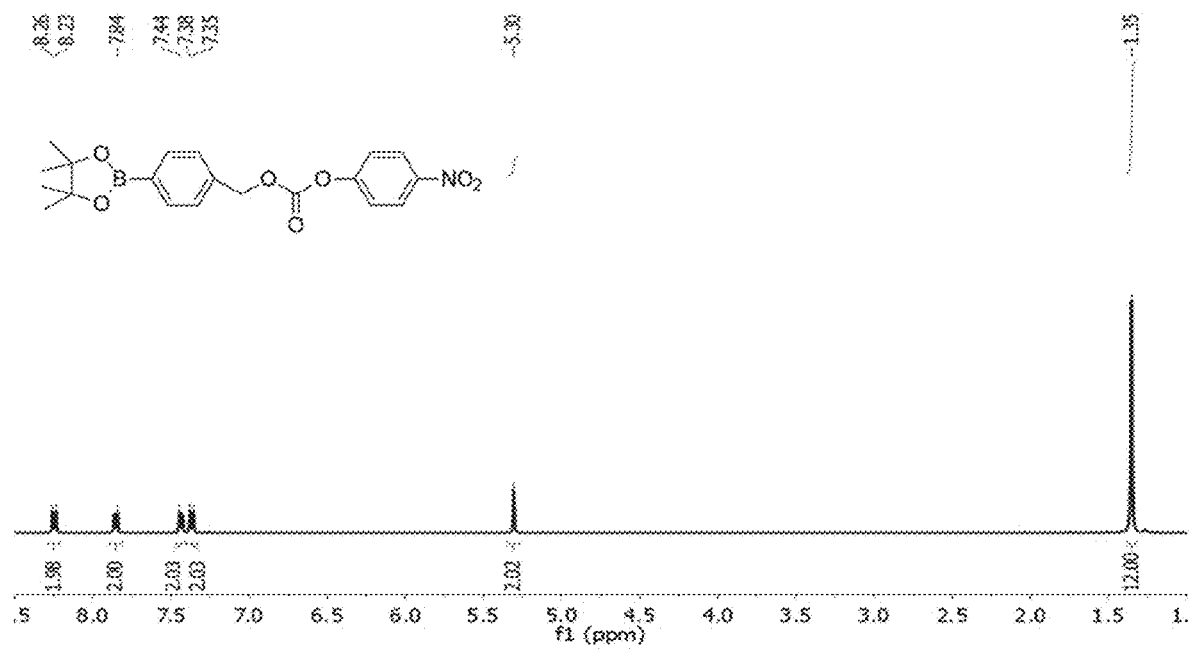
FIG. 7. $^1$H NMR spectrum of molecule 1.
Figure 8:
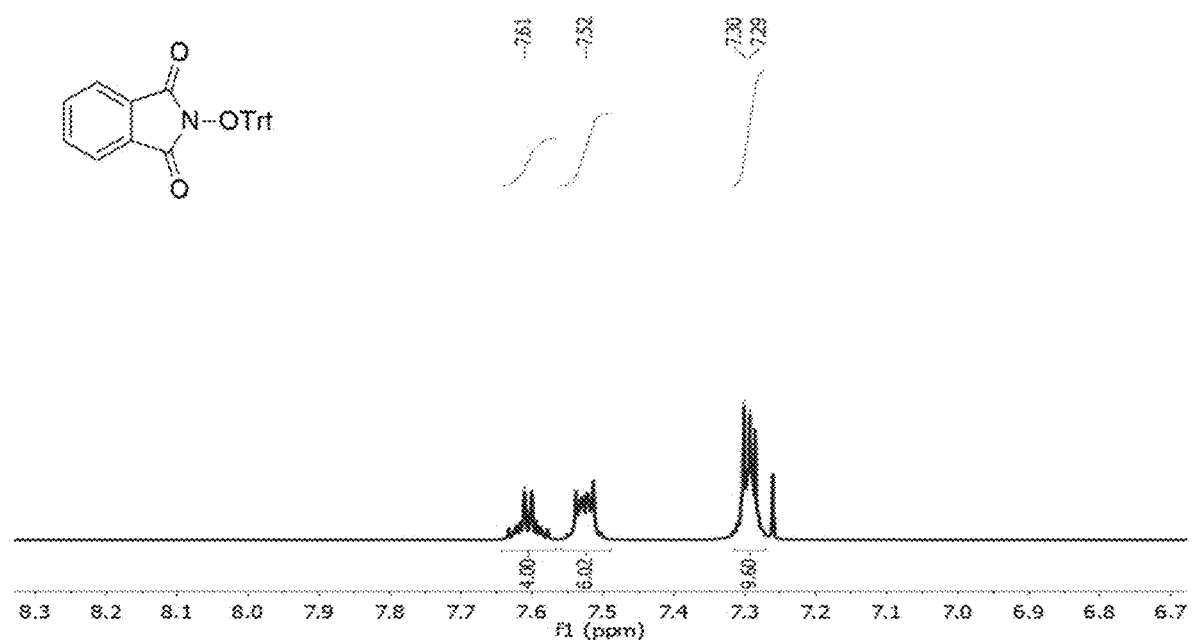
Figure 9:
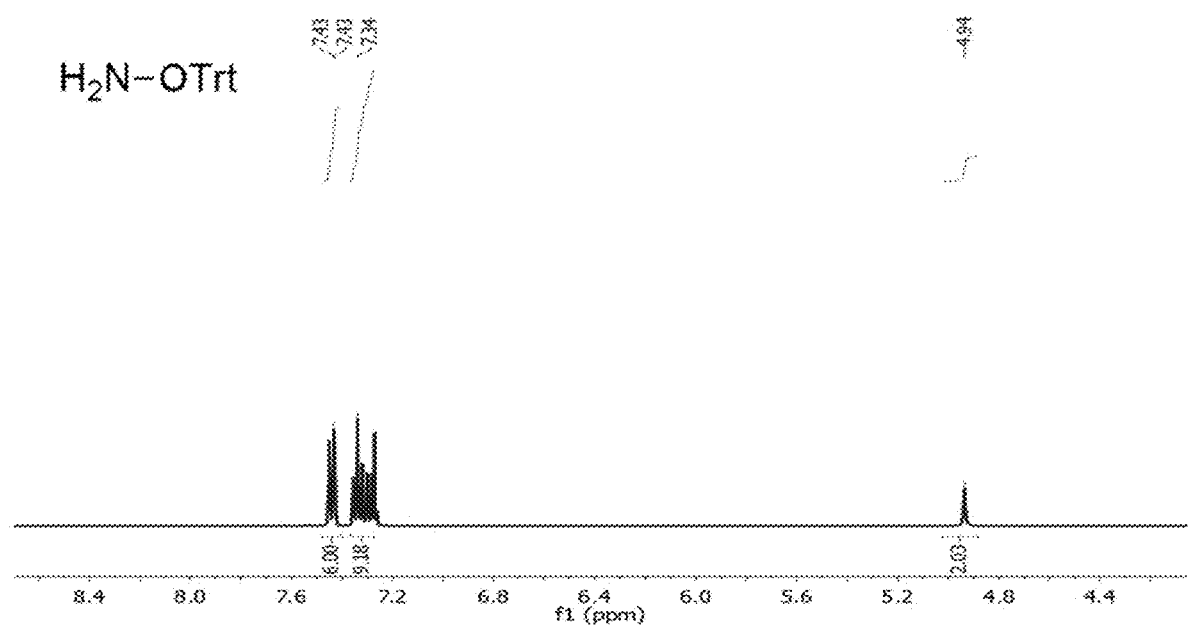
FIG. 9. $^1$H NMR spectrum of molecule 3b.
Figure 10:
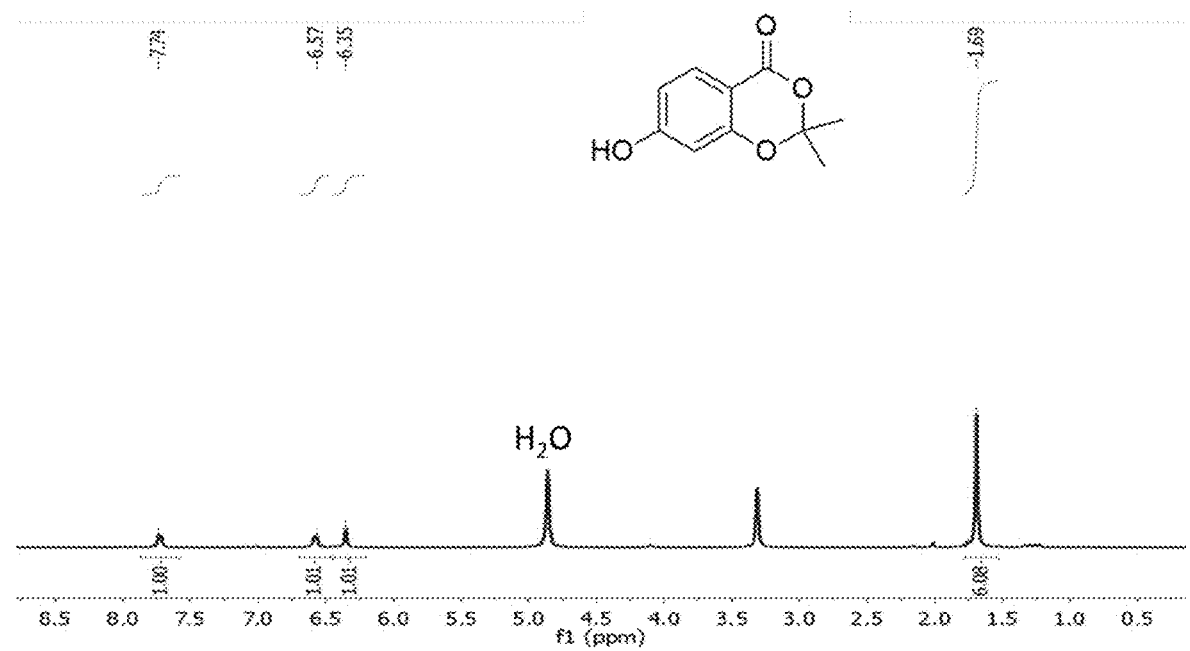
FIG. 10. $^1$H NMR spectrum of molecule 3c.
Figure 11:
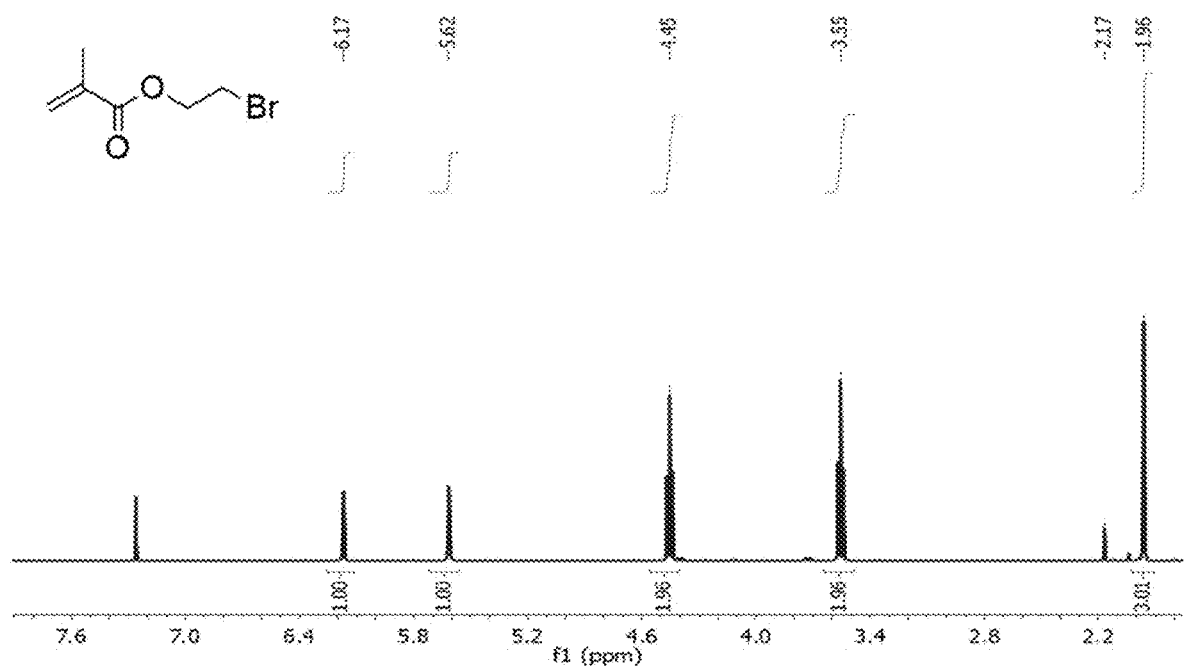
FIG. 11. $^1$H NMR spectrum of molecule 3d.
Figure 12:
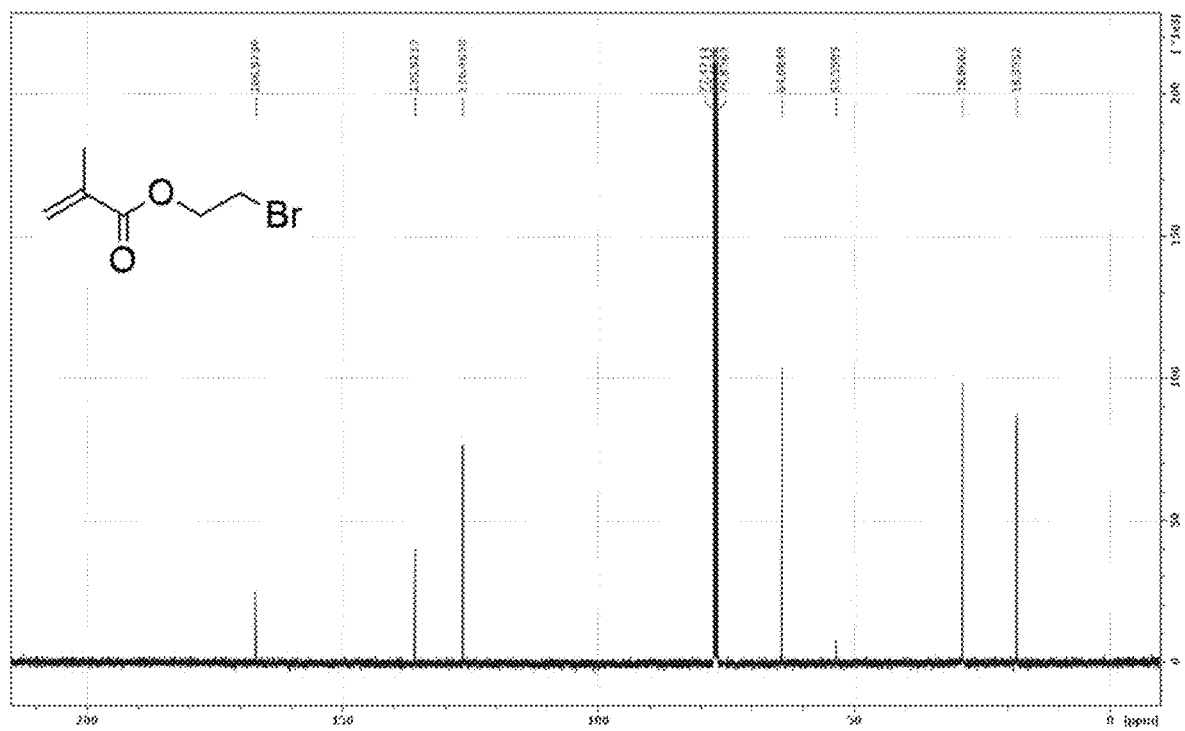
FIG. 12. $^{13}$C NMR spectrum of molecule 3d.
Figure 13:
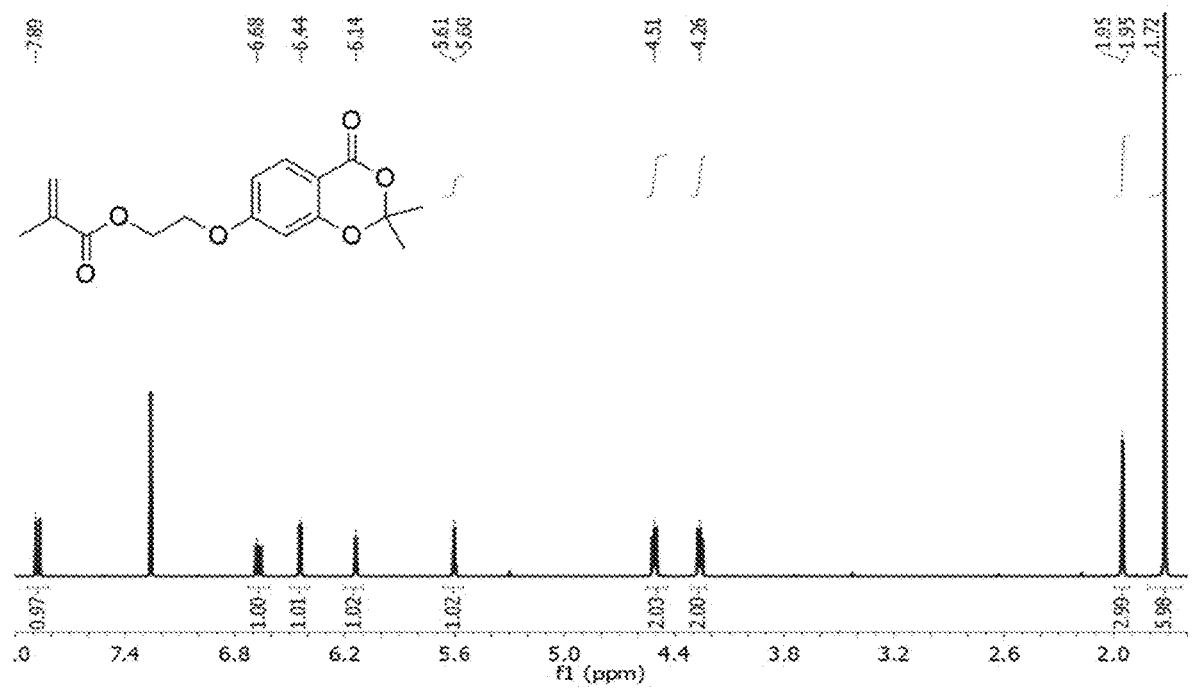
FIG. 13. NMR spectrum of molecule 3e.
Figure 14:
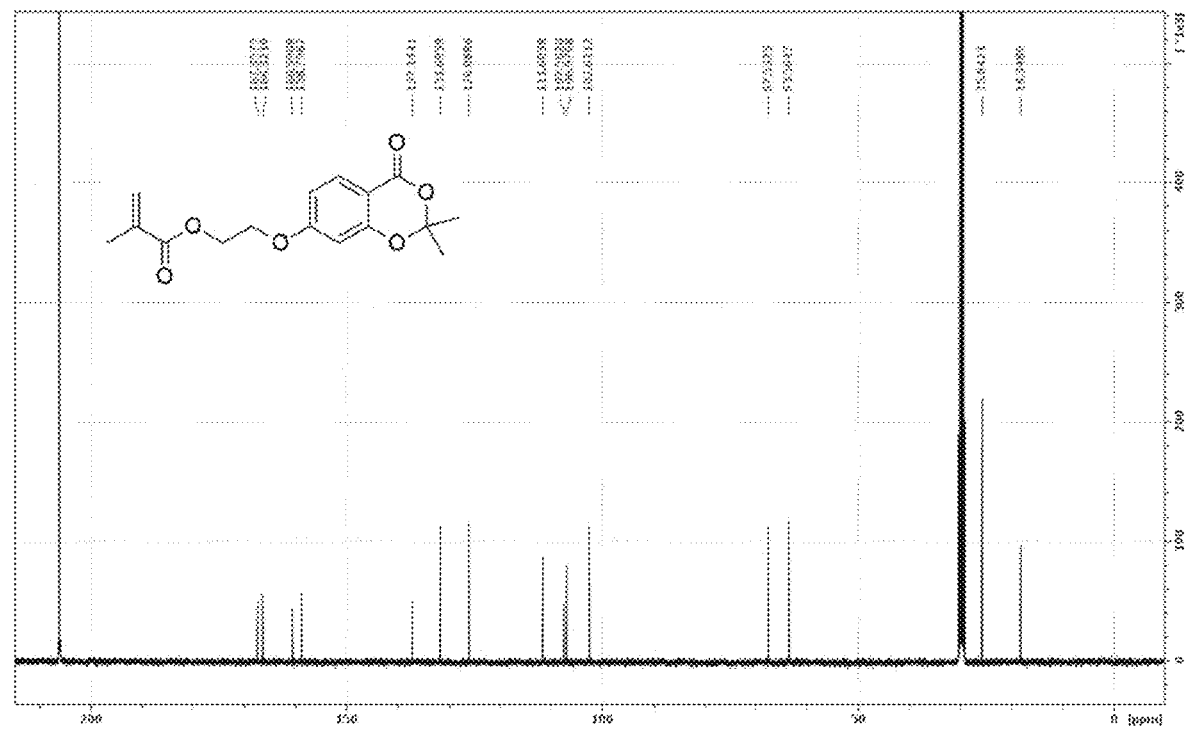
FIG. 14. $^{13}$C NMR spectrum of molecule 3e.
Figure 15:
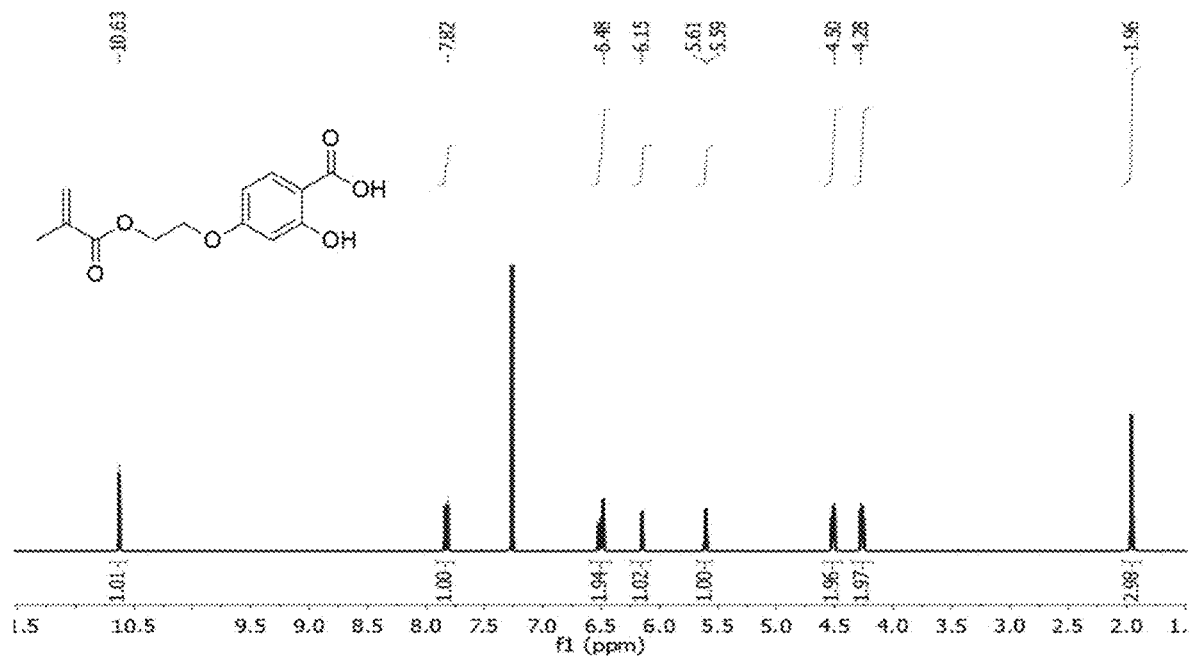
FIG. 15. NMR spectrum of molecule 3.
Figure 16:
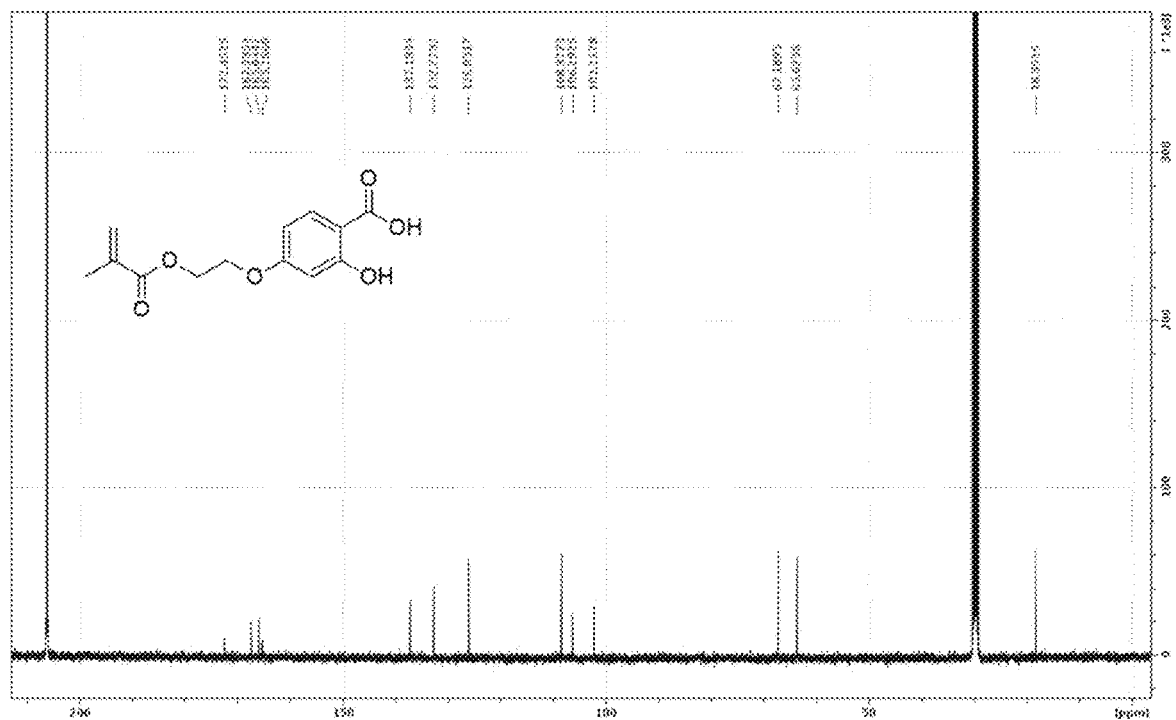
FIG. 16. 13C NMR spectrum of molecule 3.
Figure 17:
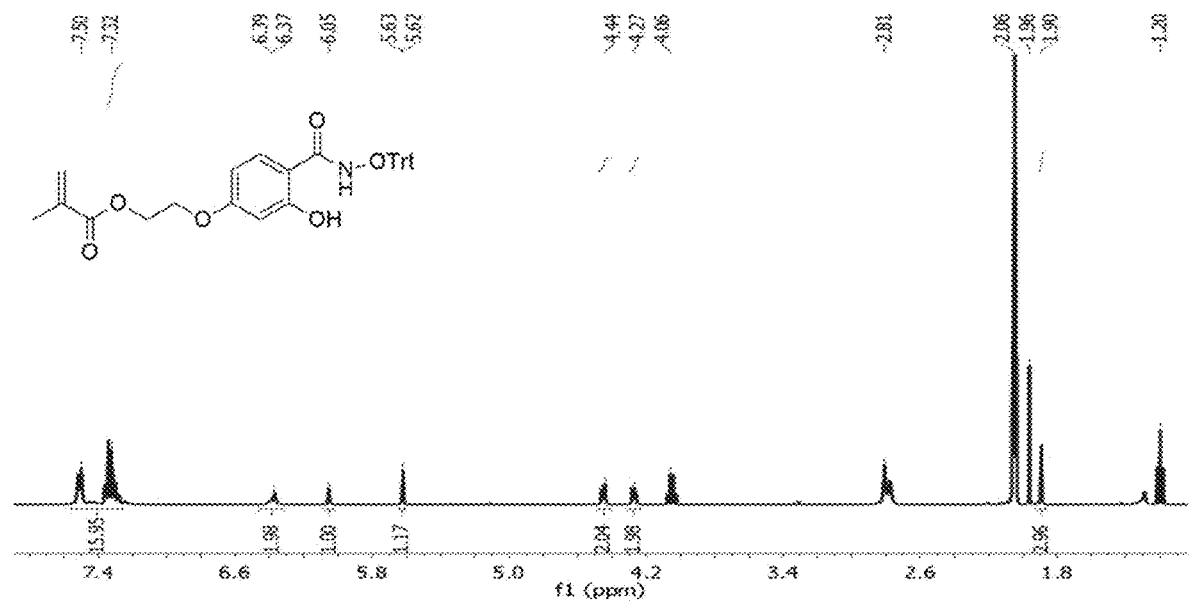
FIG. 17. $^1$H NMR spectrum of molecule 4.
Figure 18:
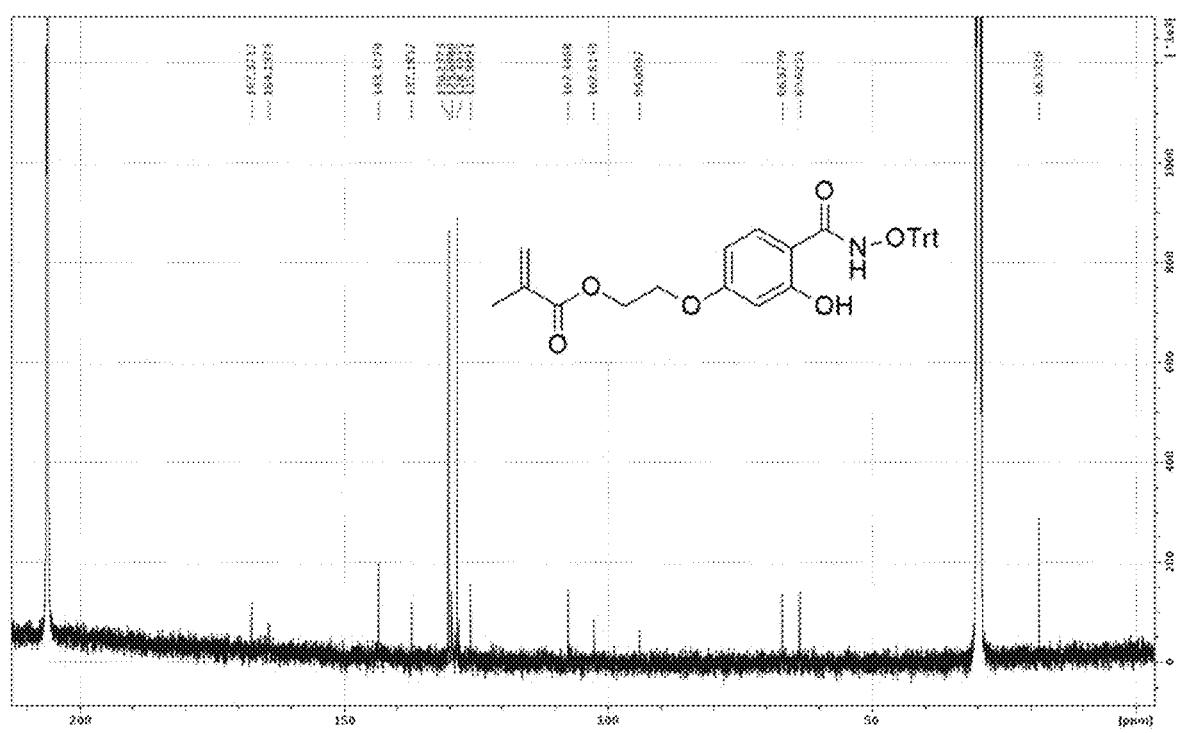
FIG. 18. $^{13}$C NMR spectrum of molecule 4.

A molecular design that offers the possibility of reduction-induced traceless release of proteins in this click chemistry based conjugate system is shown as 7 in FIG. 6. Treatment of the modified protein, RNaseA-SS-BA, with P1 affords the corresponding polymer-protein conjugate RNaseA-SS-BA@P1. The possibility of releasing the protein in the presence of physiologically relevant, intracellular concentration of GSH and the corresponding concentration of DTT was analyzed using SDS-PAGE.

Indeed, significant protein release was observed in the presence of these reducing agents, as shown FIG. 6 and FIG. 52. The true test of the fidelity of these assemblies is to test whether the functional form of protein can be delivered inside the cells, where the high native concentration of GSH would degrade the polymer-protein conjugate to cause cellular apoptosis. Indeed, a dosage-dependent cellular toxicity was noted. Since the experiment here, the PMA-induced degradation experiments, and the pH-responsive system were all carried out with respect to protein concentrations, the cellular apoptosis are comparable. It can be noted here that the reduction induced protein release is not quite as efficient as the ROS-responsive system, but is understandably better than the pH-responsive system. This is attributed to the fact that the nanoassembly is processed in the cytosol, but there is need for the diffusion of a larger GSH molecule inside the nanogels to cleave the disulfide bonds, relative to the smaller $H_2O_2$ molecules. Nonetheless, it was found that the strategy of delivering the protein to the cells using this click chemistry strategy is effective.

To further ascertain that this delivery is indeed aided by the conjugation to the polymer, also compared was the cellular apoptosis with the control, where the cells were incubated with the modified protein by itself of similar concentration. This formulation exhibited no discernible cellular apoptosis, confirming that the polymer is aiding the cellular uptake. Note also that the polymer-protein conjugate with the boronic acid moiety without any other degradable linker would release the protein inside the cells, only in the presence of oxidative stress induced by PMA (FIG. 4). In the case of the current system with an engineered disulfide bond, an intrinsic intracellular stimulus in GSH was utilized. Therefore, the protein is activated in this case without the need for PMA-based activation of the cells. This feature further supports the disclosed self-assembly and stimuli-induced disassembly mechanisms outlined here. Overall, the molecular design principle and thus the generality of the design strategy are successfully demonstrated in this system.

In order to increase the delivery efficiency, additional components were incorporated into the polymer chain through copolymerization of different functional monomers. Guanidium functionality was incorporated into the polymers for efficient delivery. P3 was synthesized though a RAFT polymerization of three monomers of trt-protected SaH (10%), PEG-MA (30%) and Boc protected guanidium monomer (60%) with subsequent acid cleavage of Trt protection group. GFP was chosen as the model protein to test the intracellular delivery efficiency, because of its intrinsic fluorescence. The surface lysines of GFP were modified by boronic acid for the complexation with polymer P3 via the same salicylhydroxamate-boronic acid reversible click reaction. The resultant nanoassembly was incubated with HeLa cells for intracellular delivery study and the efficiency was evaluated with confocal microscopy. The results showed that the cellular uptake was indeed significantly enhanced. For control, GFP lacking the boronic acid surface modification and thus cannot undergo the covalent click complexation with the polymer, was also tested for intracellular delivery in the presence of polymer. Intracellular delivery of the protein was found to be negligible, if any. These results indicate that the present strategy enhances efficiency of intracellular protein delivery. However, positively charged polymers usually reveal significant toxicity because of its electrostatic interaction with the cellular membranes. The cytotoxicity of the polymer was checked through MTT assay. Indeed, this material exhibited a very high toxicity.

Other functional groups were explored that could enhance the cellular uptake without significant toxicity. The new polymer P4 was designed by incorporation of the fluorine-component in the polymer chain, while retaining the salicylhydroxamate for efficient protein conjugation with PEG component for water solubility and compatibility. Polymer P4 was synthesized though a RAFT polymerization of the three components of trt-protected SaH (10%), PEG-MA (30%) and tri-fluoromonomer (60%) with subsequent acid cleavage of Trt protection group. The cell uptake of the GFP protein was accessed to evaluate the delivery efficiency by this polymer. However, the incorporation of the fluorine-component itself could not enhance the uptake.

It is noted that the literature works were focused on the post-modification of positive charged materials (e.g., PAMAM dendrimers and PEI) with the fluoro-component for enhanced delivery, while the polymer was a neutral one without the charge moiety. Therefore, both guanidium groups and fluorocarbon moieties were incorporated onto the polymer chain. At first, a polymer P5 was designed with 40% fluorine moiety, 20% guanidium functionality, while retaining 30% PEG and 10% of SaH for study. The intracellular delivery efficiency was also tested by confocal microscopy and flow cytometry. Incorporation of both guanidium and fluorine moieties do enhance the intracellular delivery of the proteins, compared to polymers P1 and P4. The cytotoxicity of the polymer was also tested. Interestingly, this polymer does not exhibit any discernible cytotoxicity even at the concentrations as high as 1 mg/mL. However, the delivery efficiency was much lower than P3 with very high percentage of guanidium moiety inside the chain.

Considering these results, a series of polymers were explored with systematically tuned structural features in order to achieve enhanced delivery efficiency. Factors that are considered in this structure-property relationship study include hydrophobicity of the polymers (P5-P7), charge density of the polymers (P5, P8, P9) and fluorine chain length (P10-P12). Some of the polymers (P8-P12) exhibit very high delivery efficiency, where 2-3 orders of cellular uptake enhancement was observed compared to P1.

The structures of various exemplified polymers are provided in FIG. 56.

Polymerizations were carried out under reversible-addition—fragmentation-chain-transfer (RAFT) reaction conditions. Deprotections of Boc- and Trityl-protected copolymer were performed in TFA solution. The composition of each moiety was measured by proton nuclear magnetic resonance CH NMR), which was consistent with the feed ratio of the monomers.

Polymer structures of P3'-P12' are shown in FIG. 57.

Scheme 3 shows exemplary synthetic approach to certain polymers P3'-P9' discussed herein.

Scheme 3

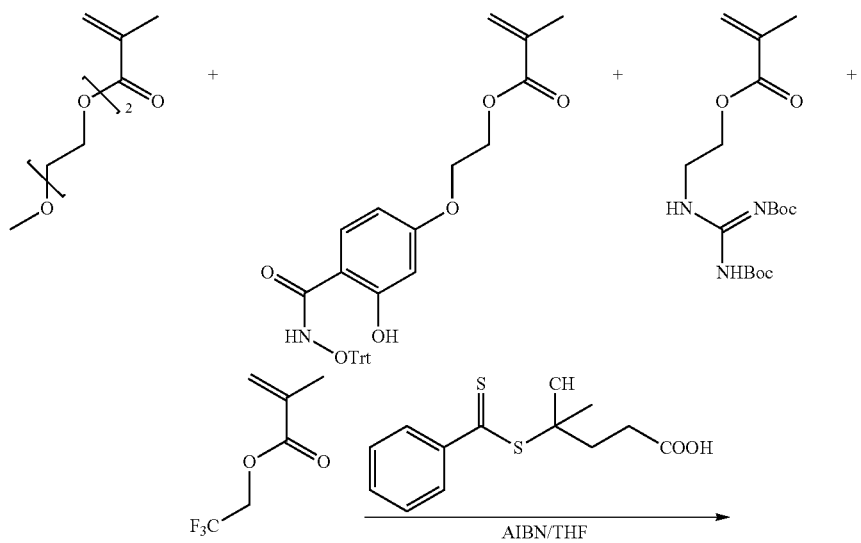

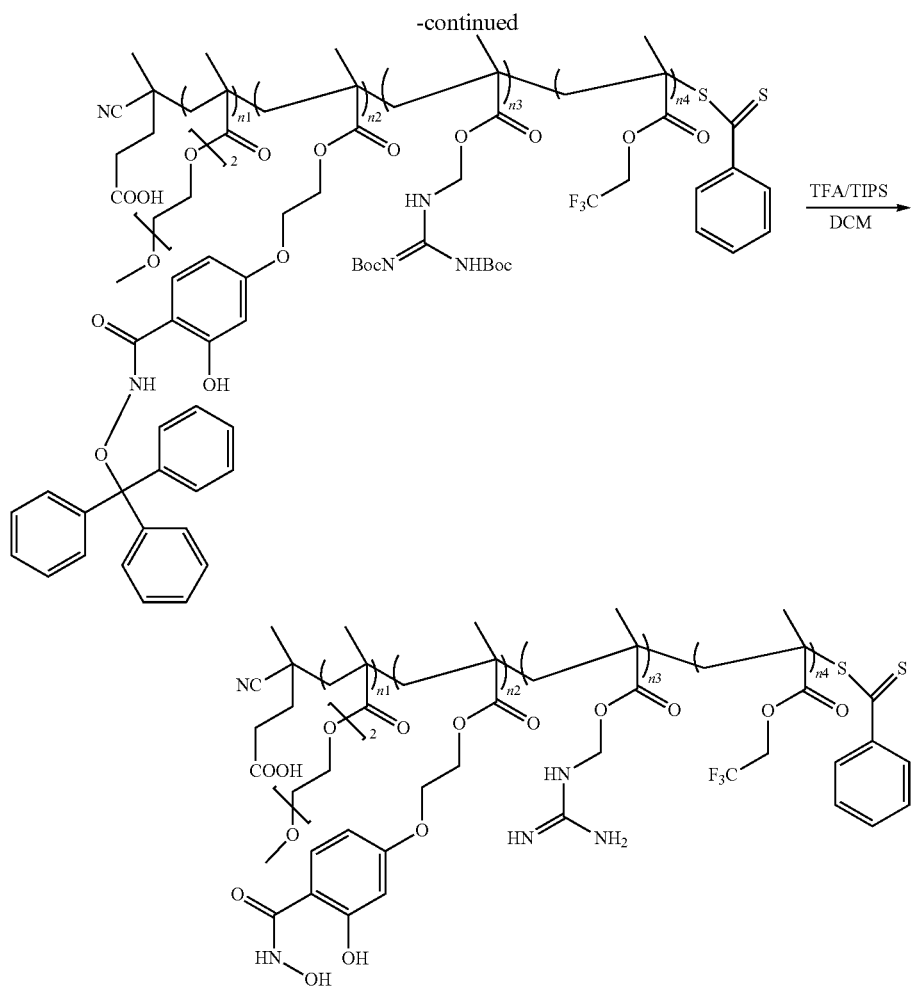

A reactive self-assembly process, based on the ultrafast click reaction between salicylhydroxamic acid and boronic acid moieties, can be utilized for generating functional polymer-protein conjugate nanoassemblies. Polymer-protein nanoconjugates can be quantitatively generated using a simple 'mix and go' approach, where boronic acid-modified proteins react with salicylhydroxamic acid side chain functionalities of a polymer. The versatility of this reactive self-assembly approach has been demonstrated through variations in protein structures, their responsive behavior to a variety of stimuli, and utility in intracellular transport of proteins. Also shown was that proteins of different sizes (from ~14 kDa to ~400 kDa) can be utilized in the self-assembly based encapsulation. Both cationic and anionic proteins can be utilized to form these nanoassemblies with practically indistinguishable efficiencies. In addition, the conjugation can be fully reversed, to cause programmed disassembly of the conjugate and thus releasing the proteins from the polymer. The linkers have been engineered such that this process results in traceless release of proteins, where there are no remnants of functional group modifications on protein surfaces. In addition to exploiting the inherent susceptibility of boronic acids to oxidants to cause this stimulus-triggered disassembly, self-immolative linkers were introduced to expand the sensitivity of the nanoassemblies to other stimuli, such as pH and reducing conditions. Overall, this work shows that reaction between polymers and proteins can be quite efficient, when the reactive functional groups are judiciously chosen to overcome the sparse functional group densities and low reaction concentration requirements. The synthetic approach and the subsequent self-assembly process, involving polymers and proteins, have implications in a variety of research areas including triggerable catalysis and biologics delivery. Also demonstrated was the direct implications of the self-assembly strategy with intracellular delivery of proteins into mammalian cells.

Experimental

Materials and instruments. Unless mentioned, all chemicals and proteins were used as received from Sigma-Aldrich. $^1$H-NMR and $^{13}$C-NMR spectra were recorded on a 400 MHz Bruker NMR spectrometer. Molecular weight of the polymers was measured by gel permeation chromatography (GPC, Waters) using a PMMA standard with a refractive index detector and THF as eluent with a flow rate of 1 mL/min. Dynamic light scattering (DLS) measurements were performed using a Malvern Nanozetasizer. UV-visible absorption spectra were recorded on a Varian (model EL 01125047) spectrophotometer. The fluorescence spectra were obtained using a JASCO FP-6500 spectrofluorimeter. Fluorescent images were recorded on Nikon with Yokogawa spinning disk (SD) and Nikon A1 spectral detector confocal with FLIM module.

Protein modification by ROS sensitive linker. 3 mg of RNase A was dissolved in 0.5 mL of 0.1 M NaHCO$_3$buffer solution (pH=8.5). To the above solution was added 150 μL of DMSO solution containing 4.8 mg compound 1. The reaction mixture was then stirred at ambient temperature for an additional 10 h, followed by filtration with a 220 μM filter and an ultrafiltration purification using Amicon® Ultra Centrifugal Filters (MWCO=3,000). The final protein was dissolved in 300 μL of DI water (10 mg/mL) and stored at 4° C. The modification of the boronic acid linker was quantified by MADLI-MS. Other proteins such as GFP, BSA, and β-gal were prepared using the similar method and also stored at 4° C. with the concentration of 10 mg/mL. The boronic acid modified proteins with ROS responsiveness (RNase A, GFP, BSA, β-gal) are denoted as RNaseA-BA, GFP-BA, BSA-BA, β-gal-BA.

Protein modification by redox and pH sensitive linker. The method for modification of proteins with redox and pH sensitive linkers is similar to that for ROS sensitive linker by using compound 6 and 7 for reaction. For instance, 3 mg of RNase A was dissolved in 0.5 mL of 0.1 M NaHCO$_3$buffer solution (pH=8.5). To the above solution was added a 150 μL of DMSO solution containing 6 mg of compound 6 or 4 mg of compound 7. The reaction mixture was then stirred at room temperature for additional 10 h, followed by filtration on 220 filter and ultrafiltration purification using Amicon® Ultra Centrifugal Filters (MWCO=3,000). The final protein was dissolved in 300 μL DI water (10 mg/mL) and stored at 4° C. The modification was quantified by MADLI-MS. The modified RNase A with redox sensitive linker is referred to RNase A-SS-BA. The pH sensitive linker modified RNase A is referred to RNase A-BA_pH.

Labeling of proteins with Rhodamine B. To perform the cellular uptake studies, fluorescently-labelled proteins (RNase A, BSA, RNase A-BA and BSA-BA) were prepared by reaction with rhodamine B (RB) isothiocyanate. In a typical labelling procedure, proteins (3 mg) were dissolved separately in 2 mL of 0.1 M NaHCO$_3$buffer (pH 8.5) under stirring. RB isothiocyanate (5 eq. of each protein, 10 mg/mL in DMSO) was added dropwise to the protein solution and stirred at ambient temperature for 2 h in dark. The RB-labelled-proteins were purified by extensive ultrafiltration purification using Amicon® Ultra Centrifugal Filters (MWCO=3,000) to remove excess RB.

MALDI-MS for quantification of the modification. The surface functional boronic acid modification of the proteins was quantified by MALDI-MS. MALDI-MS analyses were performed with Bruker Autoflex III time-of-flight mass spectrometer. All mass spectra were acquired in reflectron mode with an average of 500 laser shots at ~60% optimized power.

Preparation of protein-polymer nanoassemblies. Protein-polymer nanoassemblies were prepared by mixture of the boronic acid modified protein and polymer with different mass ratios at ambient temperature for 12 h.

Fluorescence polarization measurement. Fluorescence polarization was used to monitor the complexation kinetics of the polymer and boronic acid modified protein. GFP was chosen to study the fluorescent polarization because of its intrinsically strong fluorescence. Fluorescence polarization was monitored using a SpectraMax M5 plate reader with a fixed excitation wavelength set to 480 nm and an emission wavelength set to 520 nm. Samples (GFP, GFP-BA, GFP+polymer, and GFP-BA+polymer) were incubated in 96-well plate and the fluorescence polarization was measured immediately after placing all the components together with an interval of 30 s. The process lasted for 2 h at ambient temperature. The ratio between the protein and polymer was 1:10.

Fluorescence titration by Alizarin Red S (ARS) assay. To further monitor the protein-polymer complexation, 0.0025% w/v ARS solution was incubated with 0.25 mg/mL of RNase A-BA for 2 h. This solution was further titrated with different amounts of polymer. In all processes, the concentrations of the RNase A-BA and ARS were kept constant. After the polymer was incubated for another 15 min, ARS fluorescence was monitored at 600 nm with excitation at 490 nm.

ROS-responsive study of RNaseA-BA and related nanoassemblies. RNase A-BA and RNase A-BA@polymer (protein and polymer ratio was 1:10) were incubated with 10 mM of $H_2O_2$ at ambient temperature for 12 h, followed by ultrafiltration purification using Amicon® ultracentrifugal filters (MWCO=3,000). The proteins were then subjected to ESI-MS characterization or enzyme activity assay and compared to modified proteins without $H_2O_2$ treatment or native RNase A.

SDS-PAGE gel for protein-polymer complexation and release studies. 20 μL of different samples were mixed with 5 μL of loading buffer and 20 μL of each sample was loaded on acrylamide gel. The protein-polymer mixture was prepared by incubation of the polymer and boronic acid modified protein for 12 h.

For complexation kinetics, the polymer and the protein were mixed in a centrifuge tube for different times. At the desired time, the complex was mixed with loading buffer and was characterized with a run in the gel immediately.

For ROS responsive release experiment, identical protein-polymer conjugate samples (after incubation for 12 h) were treated with different amounts of $H_2O_2$ (1 mM or 10 mM) and incubated at room temperature for different time intervals, before subjecting to acrylamide gel electrophoresis. To calculate the amount of released protein from each sample, standard curves were generated from the known concentrations of pure protein samples loaded into the gel lanes. The gel image analysis and quantification were performed with Bio-Rad Image Lab™ software.

For redox and pH responsive release experiment, the protein-polymer complexes were treated with DTT (or GSH, 10 mM) and pH=5.0 for 12 h, before subjecting to acrylamide gel electrophoresis.

Activity assay. For RNase A: RNaseAlert® activity kit (Thermo-Fisher Scientific) was used to check the activity of RNase A based samples. RNase A cleaves the oligonucleotide substrate consisting a fluorophore and a quencher present at two ends, thus releasing the fluorophore which can be detected and quantified with a fluorimeter. For a typical kinetics experiment, 5 μL of RNaseAlert® substrate and 10 μL of assay buffer (10×, provided by the assay kit) were placed in a black 96-well plate. To the above assay substrate, 85 μL of RNase A containing samples (2 ng/mL of final proteins) were added. The fluorescence intensity at 520 nm (Excitation 490 nm) was monitored with SpectraMax® M5 spectrophotometer over 30 mM time.

For ß-gal: Beta-galactosidase (β-gal) activity assay kit (BioVision) was used to measure the activity of β-gal based samples.\, where the fluorescence (Ex/Em=480/520 nm) was monitored in kinetic mode for 30 min. For a typical kinetics experiment, 2 μL of RNaseAlert®Substrate and 97 pit of assay buffer (provided by the assay kit) were placed in a black 96-well plate. To the above assay substrate, 1 μL of β-gal containing samples (0.5 nM of final proteins for β-Gal, β-Gal-BA, β-Gal-BA@polymer) were added.

Circular dichroism (CD) spectra. CD spectra of the protein complex, released protein and native protein samples were recorded on JASCO J-1500 spectrophotometer. The protein complex was prepared through the typical complexation method by mixture of the boronic acid modified protein and polymer with the ratio of 1:10 for 12 h. The released protein sample was prepared by incubation of the protein-polymer sample in 10 mM $H_2O_2$ for 24 h. It was further purified by ultracentrifuge with Amicon Ultra Centrifugal Filters MWCO 3k for 5 times. For recording the spectra, 200 μL of protein solution was injected into a quartz cuvette of 1-mm path length, equilibrated at 25° C. for 10 min and scanned from 190 to 250 nm (scan rate: 20 nm/min, interval: 0.2 nm, average of three spectra).

Cell culture. Different cell lines (including human cervical carcinoma HeLa cells, MDA-MB-231 cells and MCF-7 cells) were cultured in T75 cell culture flask containing Dulbecco's Modified Eagle Medium/Nutrient Mixture F-12 (DMEM/F12) in a humidified S26 incubator with 5% $CO_2$ at 37° C. Culture media was supplemented with 10% fetal bovine serum (FBS), 1% L-glutamine and 1% antibiotic-antimycotic (100 units/mL of penicillin, 100 μg/mL of streptomycin, and 0.25 μg/mL of amphotericin B).

Cellular uptake studies and endosomal escape experiment. Cell internalization studies were performed with HeLa cells, seeded at 150,000 cells/mL in glass-bottomed petri-dishes and cultured for 24 h at 37° C. in a 5% $CO_2$ incubator. Prior to delivery, cells were washed three times with PBS buffer and incubated with 1 mL media containing polymer-rhodamine B-protein conjugate or rhodamine B-protein conjugate (protein concentration 30 μg/mL) at 37° C. for 6 h. After that, cell nucleus was stained with Hoechst 33342 (8 μM) and finally the media was replaced with fresh stock and incubated for another 1 h before subjecting to CLSM analysis. In addition, to studying the endosomal escape of the labelled proteins, HeLa cells were incubated with labelled nanoassemblies for 4 and 24 h. After that, it was stained with LysoTracker® Green to label endosomes/lysosomes and studied the co-localization of red and green fluorescence channels. Live cell imaging was performed using Nikon Spectral A1 confocal microscope.

Cell viability by MTT assay. Different cells (including HeLa cells, MDA-MB-231, MCF-7) were seeded into 96-well tissue culture plates at a density of 10, 000 cells/well/100 μL sample and incubated at 37° C. After 24 h, culture media was replaced and cells were treated with different concentrations of protein-polymer complex and control protein samples (0.1 mg/mL to 2 mg/mL protein-polymer complex; naked protein and modified protein concentrations were matched with the protein-polymer complex) in 100 μL media (10 μL protein containing solution with different concentrations+90 μL medium). At the desired time interval, the medium was removed and the cells were cultured by 100 μL 10% MTT (5 mg/mL) in medium solution for another 4 h. Then, the solution was discarded and the remaining crystal was dissolved by 100 μL DMSO. The solution was subjected to absorbance measurement with SpectraMax® M5 at 590 nm. Cell death was measured by the MTT assay in triplicate.

Cell viability after PMA treatment for ROS sensitive nanoassembly. HeLa cells were seeded in a 96-well plate for 24 h, before the delivery experiment was performed at a density of 10,000 cells per well (100 μL). On the day of the experiment, cells were pre-treated with RNase A-BA@polymer nanoparticles with varied concentrations for 24 h. After nanoparticle removal, cells were then treated with 200 nM PMA in DMEM (or DMEM only as a control) for 1 h. After removing PMA and washing the cells with DMEM, cells were maintained for another 24 h with fresh culture medium before cell viability measurement using the MTT assay. The toxicity of PMA was excluded by treating cells with 200 nM PMA in the absence of RNase A complex.

Additional Experimental
Synthesis of the ROS Responsive Linker

Scheme 4. Synthesis of the ROS responsive linker.

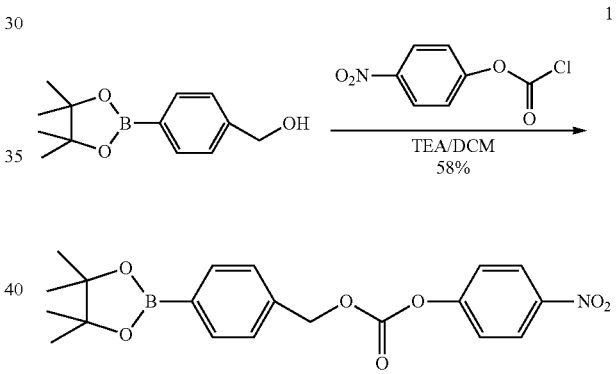

Molecule 1 was synthesized according the reported method. (Jourden, et al. *Angew. Chem. Int. Ed.* 2010, 49, 6795-6797.)

Molecule 1: $^1$H NMR (400 MHz, CDCl$_3$) (δ ppm): 8.25 (d, J=9.1 Hz, 2H), 7.85 (d, J=7.9 Hz, 2H), 7.43 (d, J=7.8 Hz, 2H), 7.36 (d, J=9.1 Hz, 2H), 5.30 (s, 2H), 1.35 (s, 12H).

Synthesis of the Salicylhydromate Functional Monomer

Scheme 5. Synthesis of the salicylhydromate functional monomer.

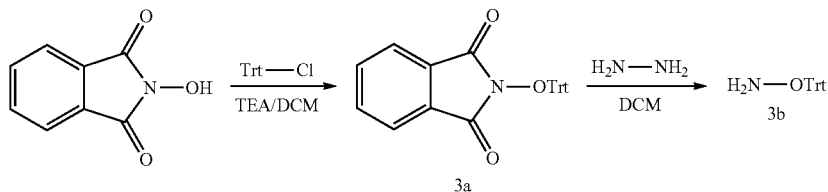

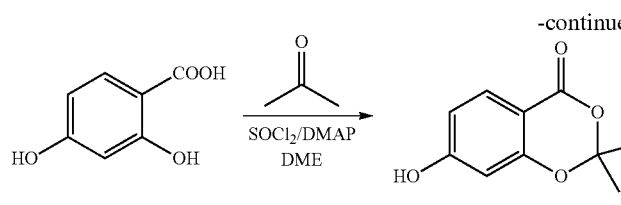

-continued

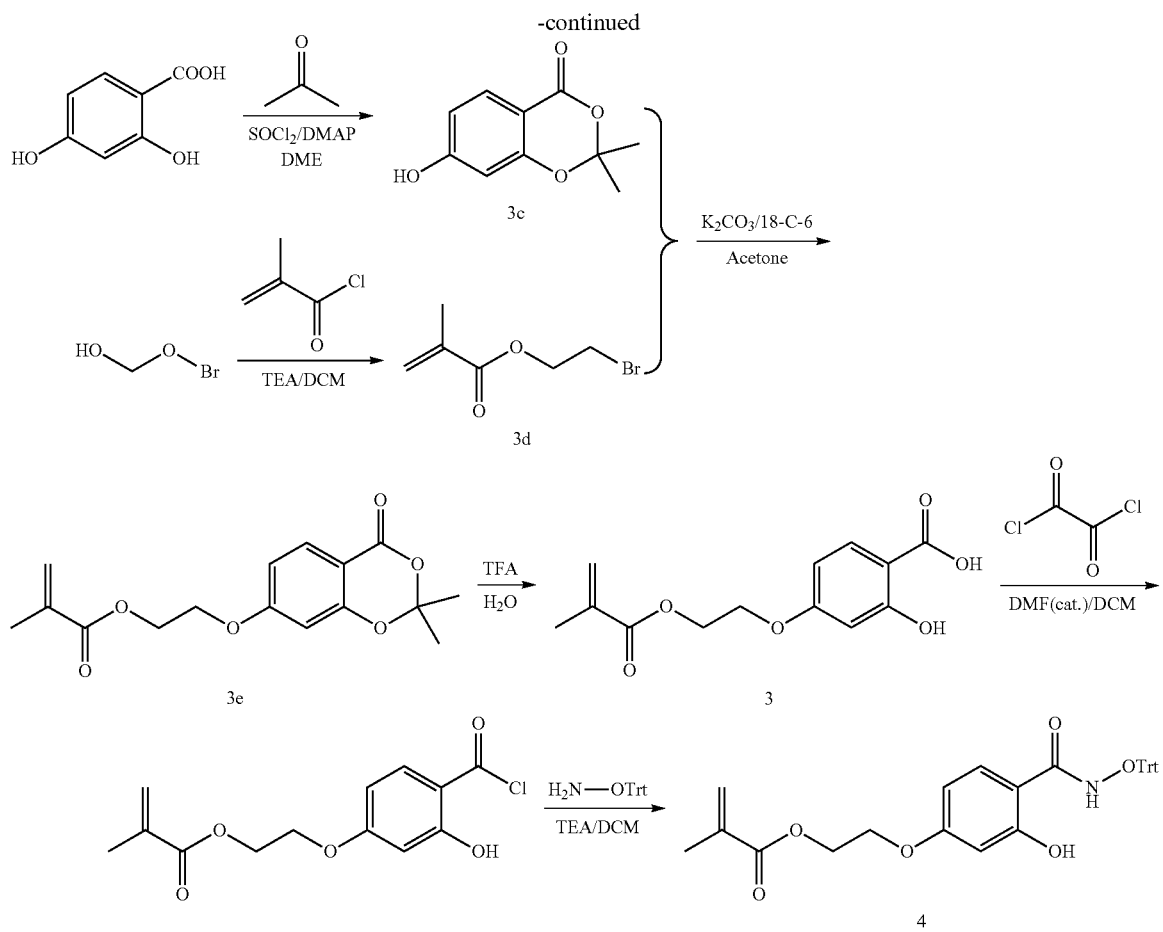

Molecule 3a and 3b were synthesized according to the literature, and the ¹H NMR spectra were consistent with the reported results. (Ng, et al. *Angew. Chem. Int. Ed.* 2014, 53, 324-328.)

Molecule 3a: ¹H NMR (400 MHz, CDCl$_3$) (δ ppm): 7.65-7.55 (m, 4H), 7.56-7.52 (m, 6H), 7.31-7.27 (m, 9H).

Molecule 3b: ¹H NMR (400 MHz, CDCl$_3$) (δ ppm): 7.48-7.40 (m, 6H), 7.38-7.24 (m, 9H), 4.94 (s, 2H).

Molecule 3c was also synthesized according to the reported method. (Wisastra, et al. *Bioorganic & Medicinal Chemistry*, 2012, 20, 5027-5032.)

Molecule 3c: ¹H NMR (400 MHz, MeOD) (δ ppm): 7.73 (d, J=8.4 Hz, 1H), 6.58 (d, J=8.1 Hz, 1H), 6.35 (s, 1H), 1.69 (s, 6H).

Synthesis of Molecule 3d

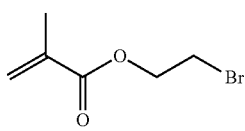

To a solution of 2-bromoethanol (8.0 g, 4.54 mL, 64.0 mmol) in 50 mL of dry dichloromethane was added 8.42 g (11.6 mL, 83.2 mmol) of triethylamine and the mixture was cooled in an ice-bath. To this cold mixture, a solution of methacryloyl chloride (8.03 g, 7.51 mL, 76.8 mmol) in 10 mL dichloromethane was added drop-wise with continuous stirring. After the addition was over the reaction mixture was stirred at room temperature for overnight. The stirring was stopped and the reaction mixture was washed with saturated NaHCO$_3$ solution (twice), distilled water and finally with brine. The organic layer was collected, dried over anhydrous Na$_2$SO$_4$ and concentrated to get the crude product. It was further purified by combiflash using silica gel as stationary phase and mixture of ethyl acetate/hexane as eluent. (7.2 g, Yield: 60%)

¹H NMR (400 MHz, CDCl$_3$) (δ ppm): 6.17 (p, J=1.4 Hz, 1H), 5.62 (p, J=1.5 Hz, 1H), 4.45 (t, J=6.1 Hz, 2H), 3.55 (t, J=6.1 Hz, 2H), 1.98-1.94 (m, 3H).

¹³C NMR (100 MHz, CDCl$_3$) (δ ppm): 169.97, 135.92, 126.47, 64.08, 28.86, 18.36.

Synthesis of Molecule 3e

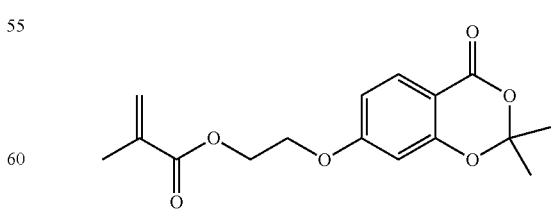

Compound 3c (2.0 g, 10.3 mmol, 1 equiv), compound 3d (2.0 g, 10.3 mmol, 1 equiv), K$_2$CO$_3$ (7.12 g, 51.5 mmol, 5 equiv) and 18-Crown-6 (0.27 g, 1.0 mmol, 0.1 equiv) were mixed together in acetone (60 mL) and refluxed for 20 h.

The reaction mixture was concentrated in vacuo and residue was dissolved in water and the product was extracted 3 times with ethyl acetate. The organic layer was collected, dried over anhydrous $Na_2SO_4$ and concentrated to get the crude product. It was further purified by combiflash using silica gel as stationary phase with ethyl acetate/hexane as eluent. (2.46 g, Yield: 78%)

$^1$H NMR (400 MHz, $CDCl_3$) (δ ppm): 7.88 (d, J=8.7 Hz, 1H), 6.67 (dd, J=8.8, 2.4 Hz, 1H), 6.44 (d, J=2.4 Hz, 1H), 6.14 (dd, J=1.5, 1.0 Hz, 1H), 5.60 (p, J=1.5 Hz, 1H), 4.51 (dd, J=5.4, 4.2 Hz, 2H), 4.26 (dd, J=5.3, 4.2 Hz, 2H), 1.95 (dd, J=1.5, 1.0 Hz, 3H), 1.72 (s, 6H).

$^{13}$C NMR (100 MHz, Acetone-$d_6$) (δ ppm): 167.36, 166.32, 160.59, 158.80, 137.14, 131. 126.09, 111.60, 107.50, 106.98, 102.61, 67.53, 63.56, 25.84, 18.35.

Synthesis of Molecule 3

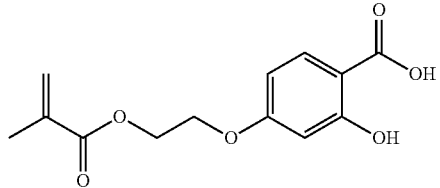

1.0 g compound 3e was dissolved in 5 mL TFA/$H_2O$ (9:1) mix solvent. The mixture was stirred overnight at room temperature. Then, TFA was removed and 5 mL ice cold water was added. The white precipitate was formed and filtrated, which was further washed with 5 mL ice old water twice. The solid product was dried by lyophilizer. (0.84 g, Yield: 96%)

$^1$H NMR (400 MHz, $CDCl_3$) (δ ppm): 10.63 (s, 1H), 7.83 (d, J=8.8 Hz, 1H), 6.67-6.36 (m, 2H), 6.15 (s, 1H), 5.61 (dd, J=3.1, 1.5 Hz, 1H), 4.51 (dd, J=6.0, 3.5 Hz, 2H), 4.39-4.16 (m, 2H), 1.96 (m, 3H).

$^{13}$C NMR (100 MHz, Acetone-$d_6$) (δ ppm): 172.45, 167.49, 165.84, 165.27, 137.19, 132.73, 126.03, 108.38, 106.29, 102.22, 67.19, 63.63, 18.35.

Synthesis of Molecule 4

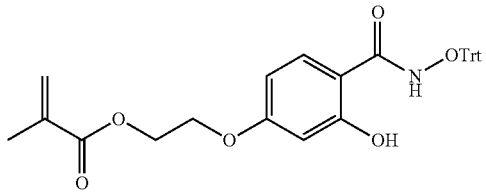

Molecule 4 was prepared through a two-step reaction as shown in Scheme 4. 0.5 g compound 3 was dispersed in 20 mL dry DCM under ice bath. Then, 0.5 mL oxalyl dichloride was added under stirring. Catalytic amount of DMF (3 drops) was added into the above mixture for reaction. The reaction was performed at room temperature for 3 h. The reaction mixture was concentrated in vacuo to remove the solvent and excess oxalyl chloride. The residue was re-dissolved in 10 mL dry DCM. 0.9 g of compound 3b was added into the above solution under ice bath. 1.5 mL TEA was added for reaction. The mixture was allowed to warm up to room temperature and reacted for another 1 week. The organic solvent was removed and purified by combiflash using silica gel as stationary phase with ethyl acetate/hexane as eluent. (0.31 g, Yield: 31%)

$^1$H NMR (400 MHz, Acetone-$d_6$) (δ ppm): 11.75 (s, 1H), 10.10 (s, 1H), 7.55-7.20 (m, 16H), 6.46-6.32 (m, 2H), 6.05 (dd, J=1.7, 1.0 Hz, 1H), 5.65-5.48 (m, 1H), 4.55-4.36 (m, 2H), 4.30-4.24 (m, 2H), 1.91-1.88 (m, 3H).

$^{13}$C NMR (100 MHz, Acetone-$d_6$) (δ ppm): 167.37, 164.20, 143.43, 137.19, 130.24, 129.69, 128.49 (m), 125.99, 107.45, 102.61, 94.01, 66.98, 63.63, 18.33.

Synthesis of the Trityl Protected Polymer (P1'):

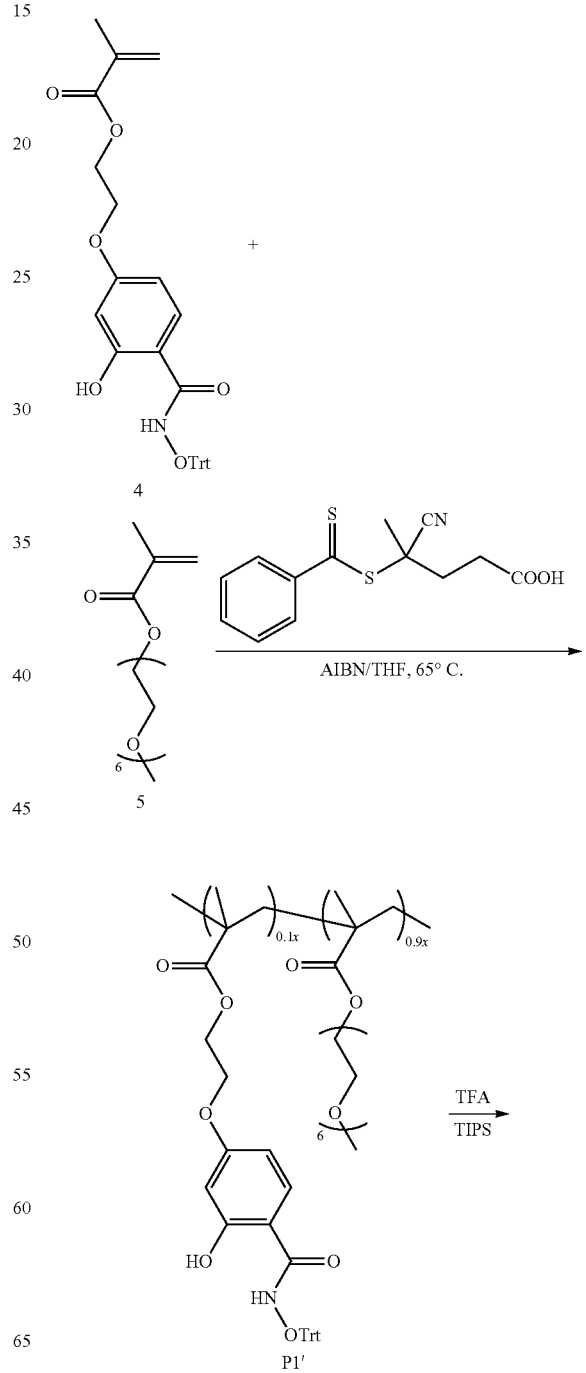

Scheme 6. Synthesis of the polymer.

Synthesis of the Rhodamine B Dye Labelled Polymer (P2):

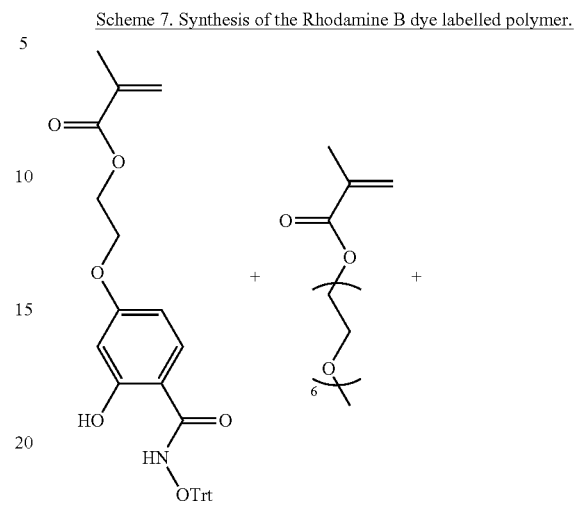

Scheme 7. Synthesis of the Rhodamine B dye labelled polymer.

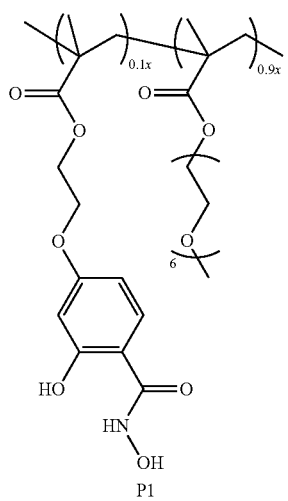

P1

Figure 19:
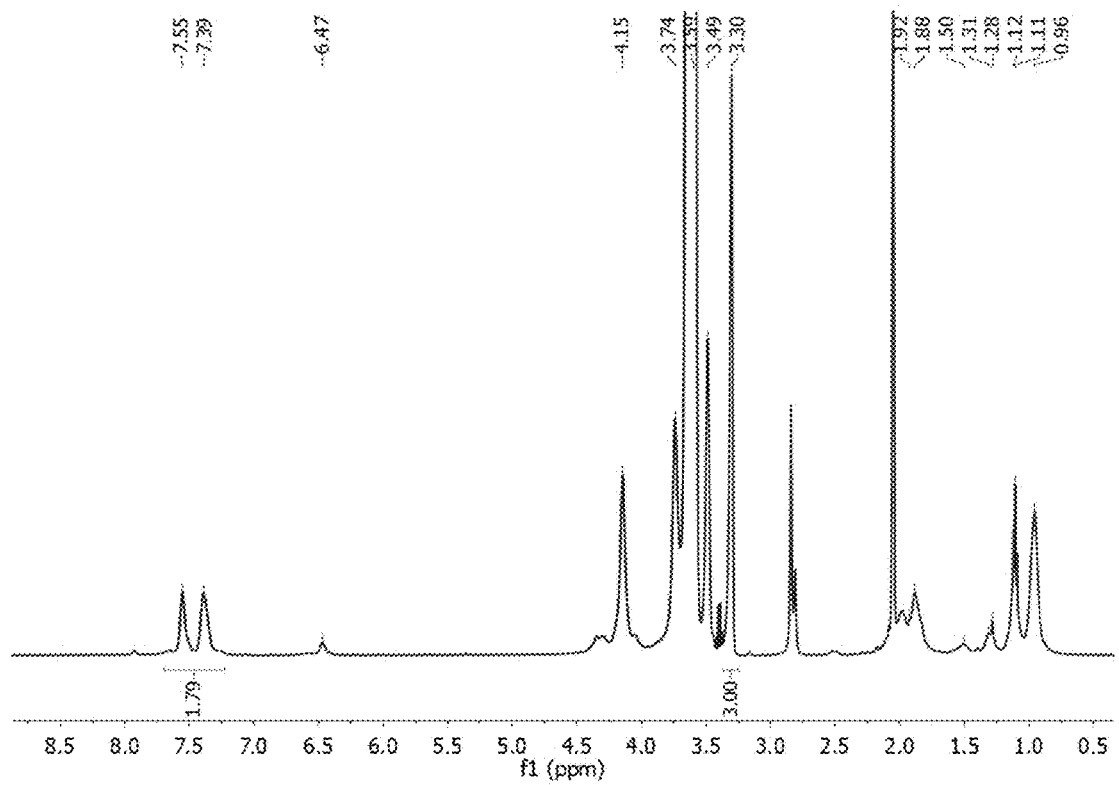
FIG. 19. $^1$H NMR spectrum of P1'.
Figure 21:
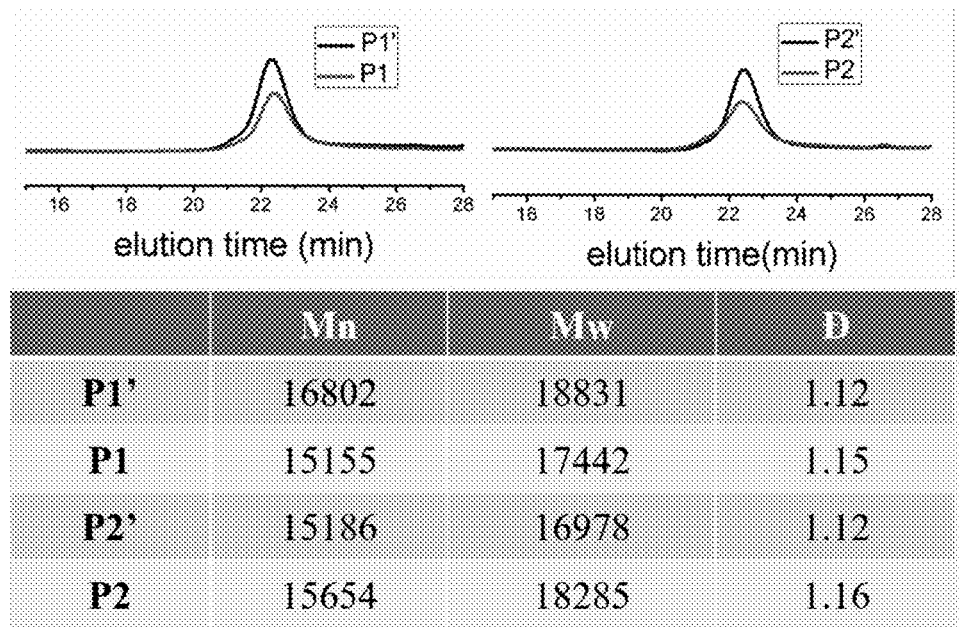
FIG. 21. Molecular weight information for different polymers.
Figure 22:
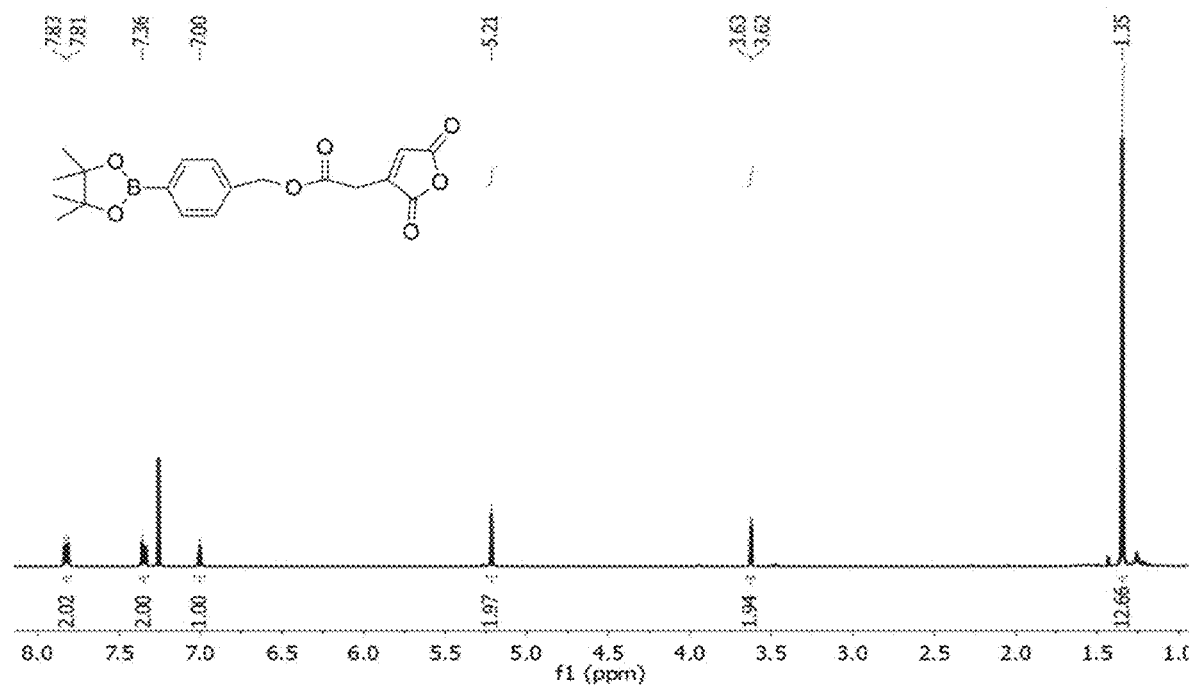
FIG. 22. $^1$H NMR spectrum of molecule 6.
Figure 23:
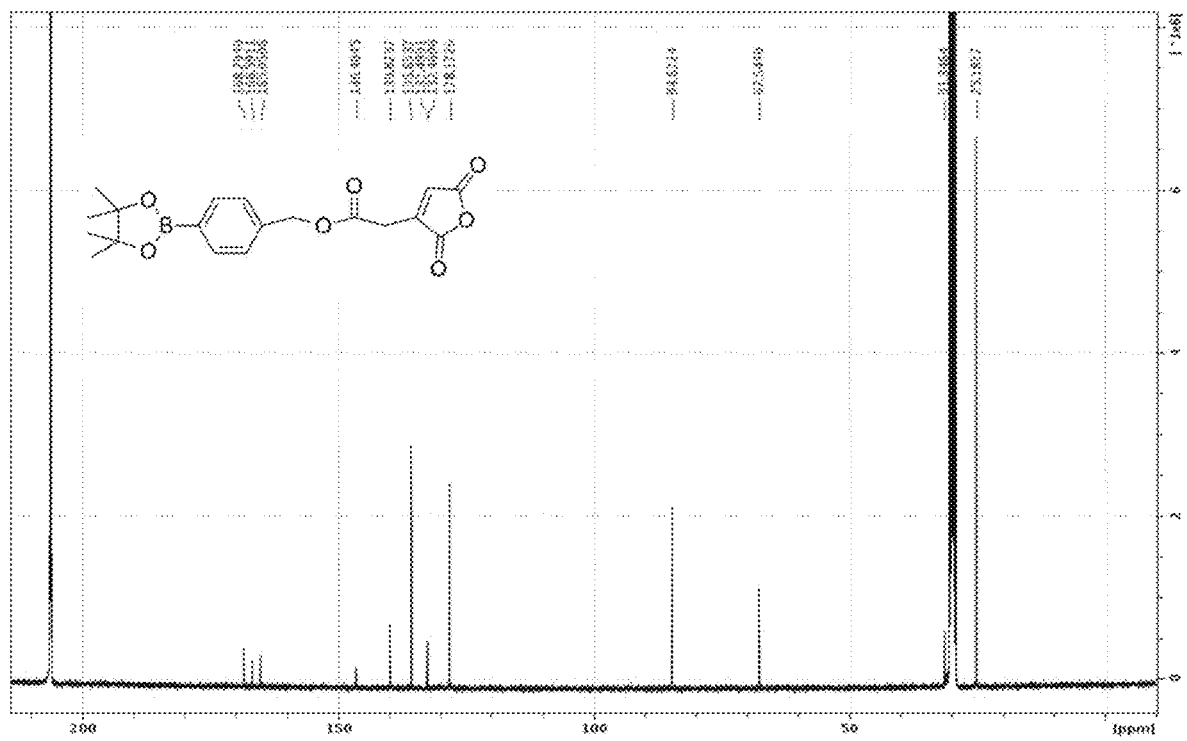
FIG. 23. 13C NMR spectrum of molecule 6.
Figure 24:
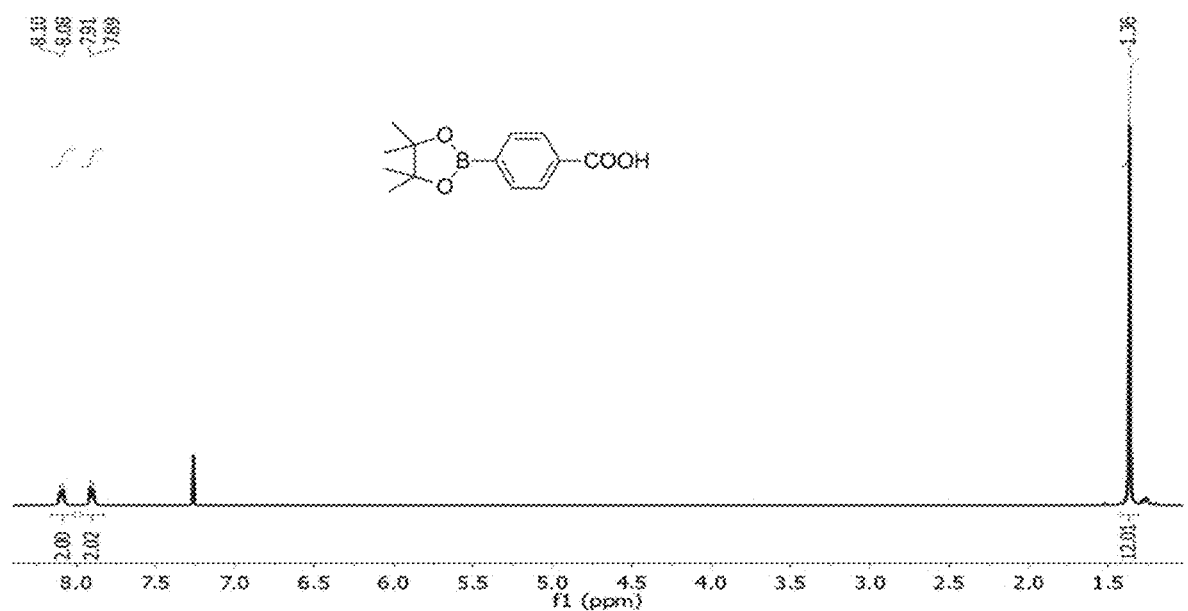
Figure 25:
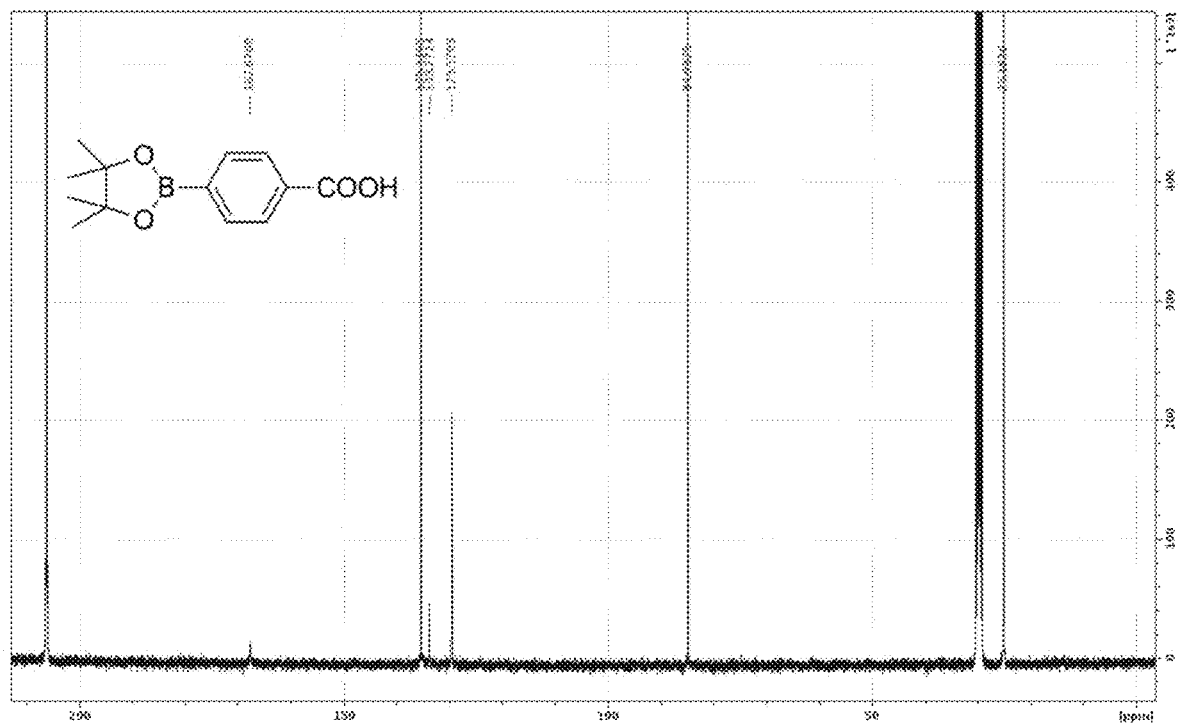
Figure 26:
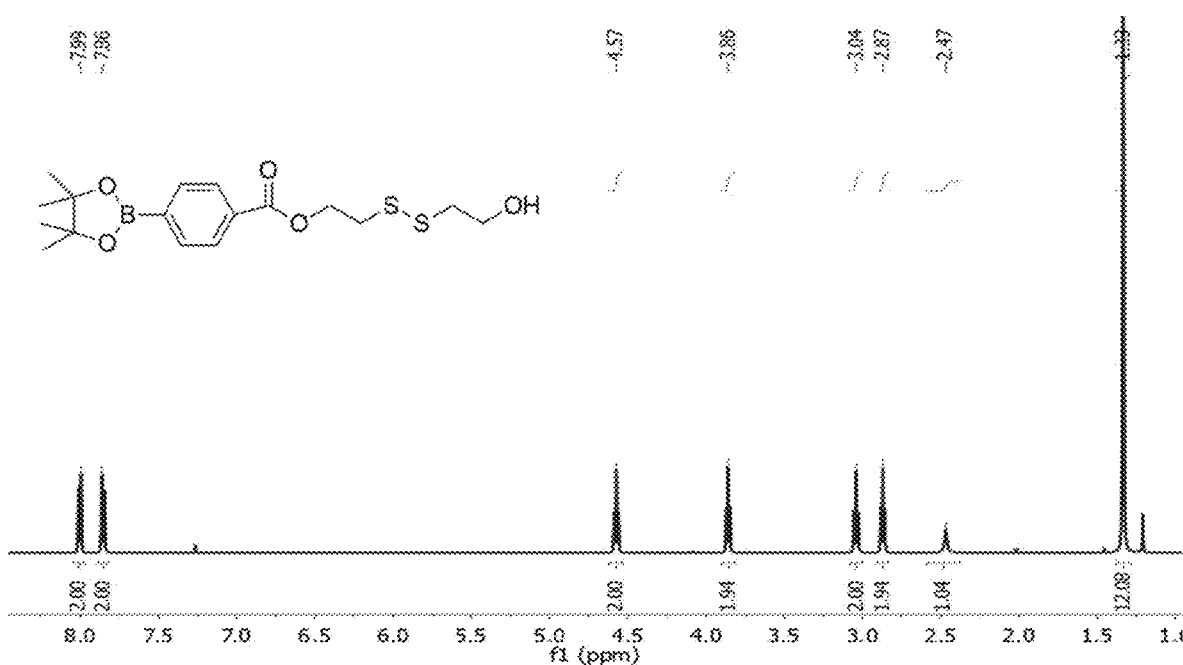
FIG. 26. $^1$H NMR spectrum of molecule 7b.
Figure 27:
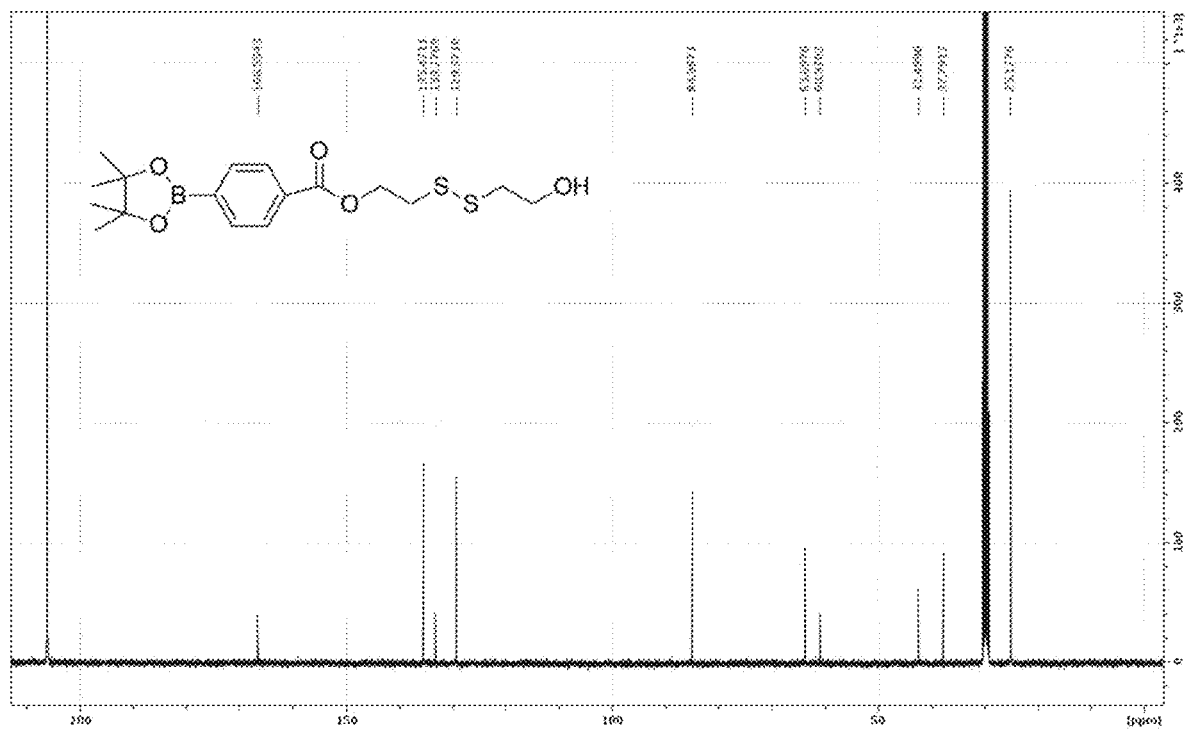
FIG. 27. $^{13}$C NMR spectrum of molecule 7b.
Figure 28:
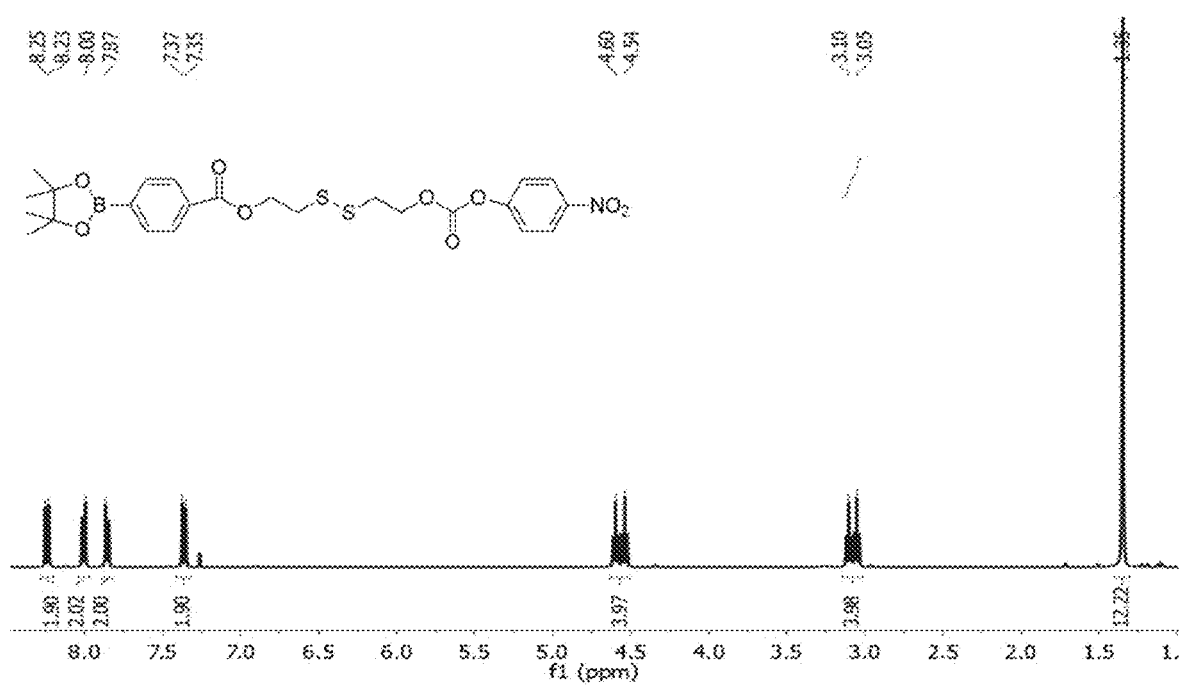
FIG. 28. $^1$H NMR spectrum of molecule 7.
Figure 29:
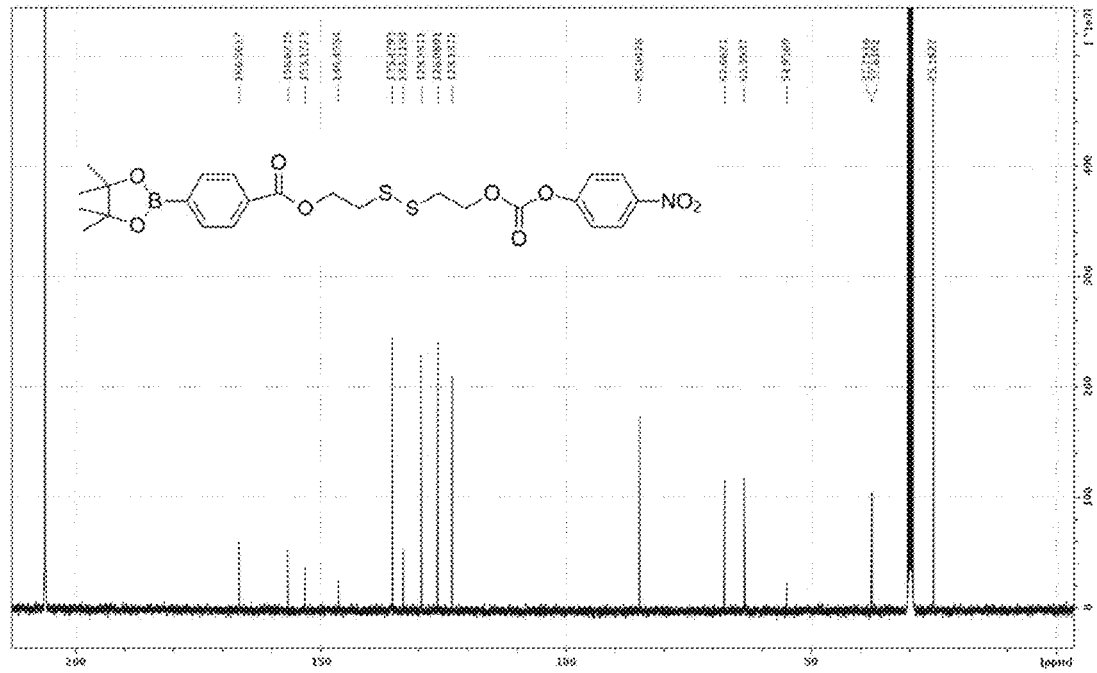
FIG. 29. $^{13}$C NMR spectrum of molecule 7.

A mixture of 4-cyano-4-(phenylcarbonothioylthio)pentanoic acid (6.2 mg, 0.022 mmol), monomer 4 (46.5 mg, 0.089 mmol), monomer 5 (polyethylene glycol monomethyl ether methacrylate, average $M_w$: 500, 400 mg, 0.8 mmol) and AIBN (1.46 mg, 0.006 mmol) were dissolved in 0.8 mL THF and degassed with three freeze-pump-thaw cycles. Then the reaction was transferred to a pre-heated oil bath (65° C.) and stirred for 36 hours under argon atmosphere. The resultant polymer was precipitated in cold diethylether and washed with the cold ether for several times to remove unreacted monomers. $^1$H NMR spectrum of the resulting polymer is shown in FIG. 19. Based on the NMR spectrum, the ratio between 4 and 5 was calculated based on the integration of peaks at 7.70-7.20 ppm (compound 4, 16H) and 3.31 ppm (monomer 5, PEG methoxy group, 3H). The monomer ratio in polymer was calculated to be 1:9, which was the same as the feed ratio. The molecular weight of the polymer was determined by GPC and the results are shown in FIG. 21. (Mw=18.8 k, PDI=1.12)

Figure 20:
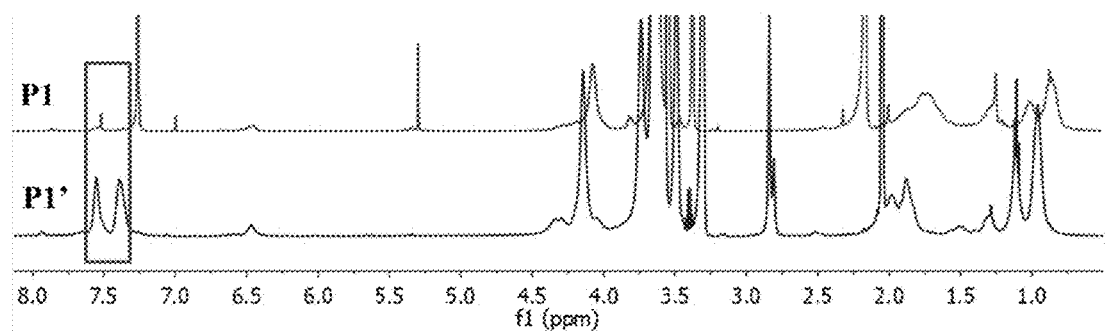
FIG. 20. $^1$H NMR spectra comparison for P1' and P1. NMR solvent for P1' is Acetone-$d_6$ and P1 is $CDCl_3$.

Deprotection of the Polymer (P1):

The polymer was further deprotected under TFA to remove the Trt protection group. 100 mg of the above synthesized polymer P1' was dissolved in 1 mL DCM. Then, 0.5 mL TFA and 0.05 mL triisopropylsilane (TIPS) was added under stirring at room temperature overnight. Then, the deprotected polymer was precipitated in cold diethylether and the product was collected by centrifuge. Further, the polymer was washed with cold ether for several times and dried under vacuum. The disappearance of the aromatic ring peak in the $^1$H NMR spectrum at 7.70-7.20 ppm for Trt group demonstrated the successful deprotection (FIG. 20). The molecular weight of the polymer was determined by GPC and the results were shown in FIG. 21. (Mw=17.4 k, PDI=1.15)

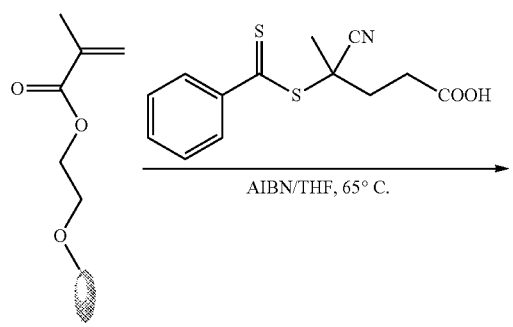

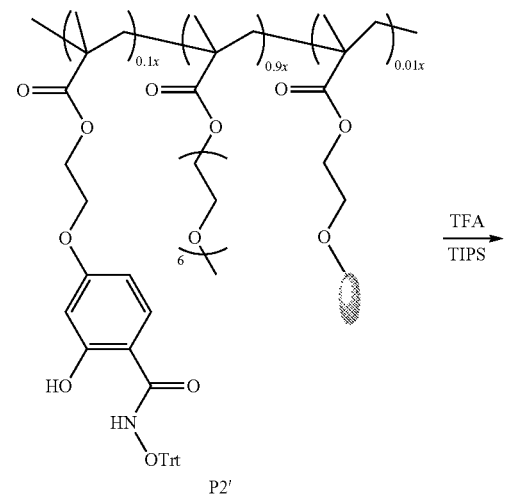

P2'

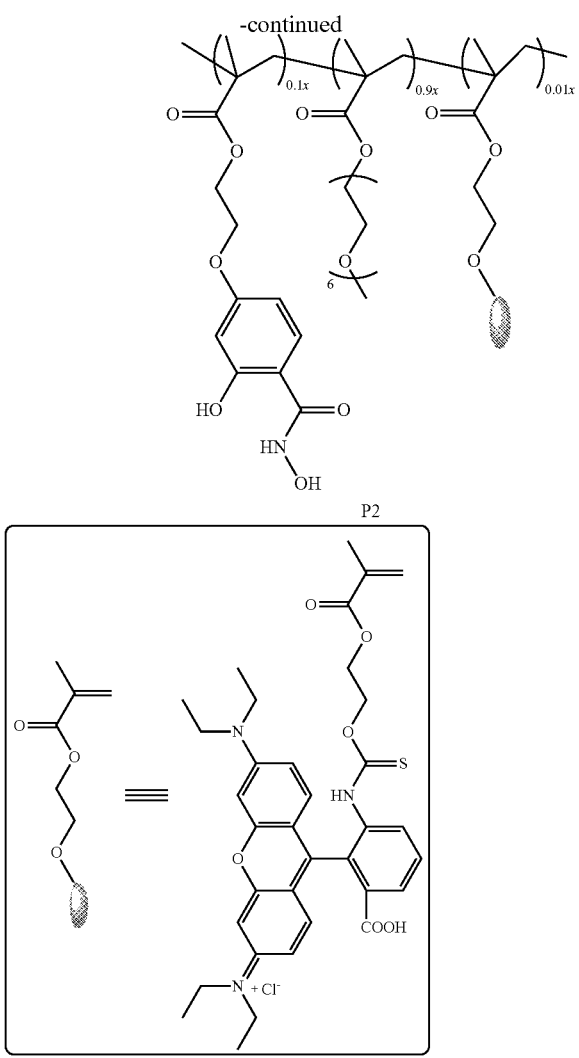

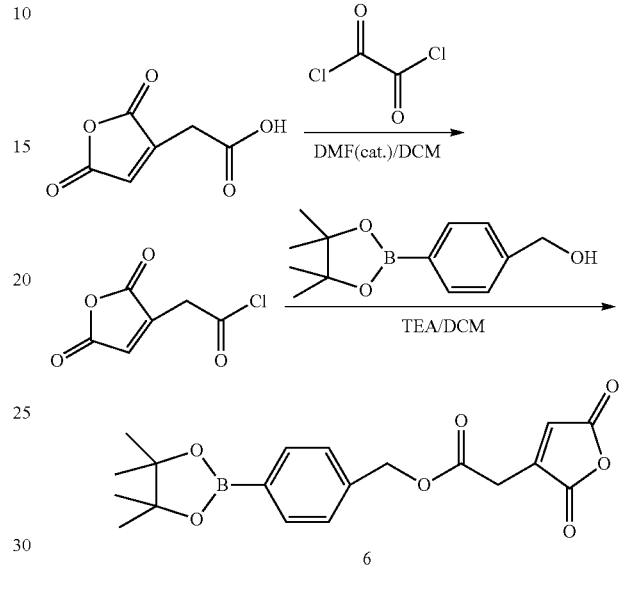

Scheme 8. Synthesis of the pH responsive linker.

Synthesis of Molecule 6

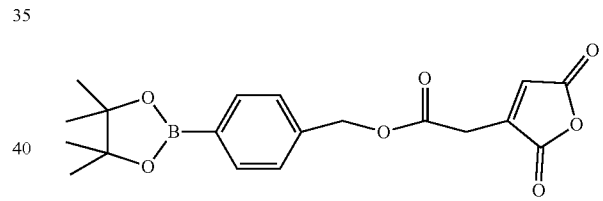

Further, the polymer was washed with cold ether for several times and dried under vacuum. The molecular weight of the polymer was determined by GPC and the results were shown in FIG. 21. (Mw=18.3 k, PDI=1.16)

Synthesis of the pH Responsive Linker:

Molecule 6 was prepared through a two-step reaction as shown in Scheme 8. 0.334 g cis-aconitic anhydride (2.1 mmol) was dissolved in 10 mL dry DCM under ice bath. Then, 0.4 mL oxalyl dichloride was added under stirring. Catalytic amount of DMF (3 drops) was added into the above mixture for reaction. The reaction was performed at room temperature for 3 h. The reaction mixture was concentrated in vacuo to remove the solvent and excess oxalyl chloride. The residue was redissolved in 10 mL dry DCM. 0.5 g of 4-(Hydroxymethyl)phenylboronic acid pinacol ester (2.1 mmol) was added into the above solution under ice bath. 1 mL TEA was added for reaction. The mixture was allowed to warm up to room temperature and reacted for another 24 h. The organic solvent was removed and purified by combiflash using silica gel as stationary phase with ethyl acetate/hexane as eluent. (0.16 g, Yield: 20%)

$^1$H NMR (400 MHz, CDCl$_3$) ($\delta$ ppm): 7.82 (d, J=8.0 Hz, 2H), 7.35 (d, J=8.0 Hz, 2H), 7.00 (t, J=1.7 Hz, 1H), 5.21 (s, 2H), 3.63 (d, J=1.7 Hz, 2H), 1.35 (s, 12H).

$^{13}$C NMR (100 MHz, Acetone-d$_6$) ($\delta$ ppm): 168.29, 166.59, 165.05, 146.40, 139.82, 135.65, 132.50, 132.46, 128.17, 84.62, 67.54, 31.35, 25.18.

A mixture of 4-cyano-4-(phenylcarbonothioylthio)pentanoic acid (6.2 mg, 0.022 mmol), monomer 4 (46.5 mg, 0.089 mmol), monomer 5 (polyethylene glycol monomethyl ether methacrylate, average M$_w$: 500, 400 mg, 0.8 mmol), Rhodamine B monomer (6.1 mg, 0.0089 mmol) and AIBN (1.46 mg, 0.006 mmol) was dissolved in 0.8 mL THF and degassed with three freeze-pump-thaw cycles. Then the reaction was transferred to a pre-heated oil bath (65° C.) and stirred for 36 hours under argon. The resultant polymer was precipitated in cold diethylether and washed with the cold ether for several times to remove unreacted monomers. The $^1$H NMR of P2' was almost the same as P1 as shown in FIG. 19. The ratio between 4 and 5 was in polymer was also calculated to be 1:9, which was the same as the feed ratio. The molecular weight of the polymer was determined by GPC and the results were shown in FIG. 21, which was very similar to P1. (Mw=17.0 k, PDI=1.12)

Deprotection of the Rhodamine B Dye Labelled Polymer (P2):

Further, the rhodamine B labelled polymer was also deprotected under TFA to remove the Trt protection group. 100 mg of the above synthesized polymer P2' was dissolved in 1 mL DCM. Then, 0.5 mL TFA and 0.05 mL triisopropylsilane (TIPS) was added under stirring at room temperature overnight. Then, the polymer was precipitated in cold diethylether and the product was collected by centrifuge.

Synthesis of the Redox Responsive Linker:

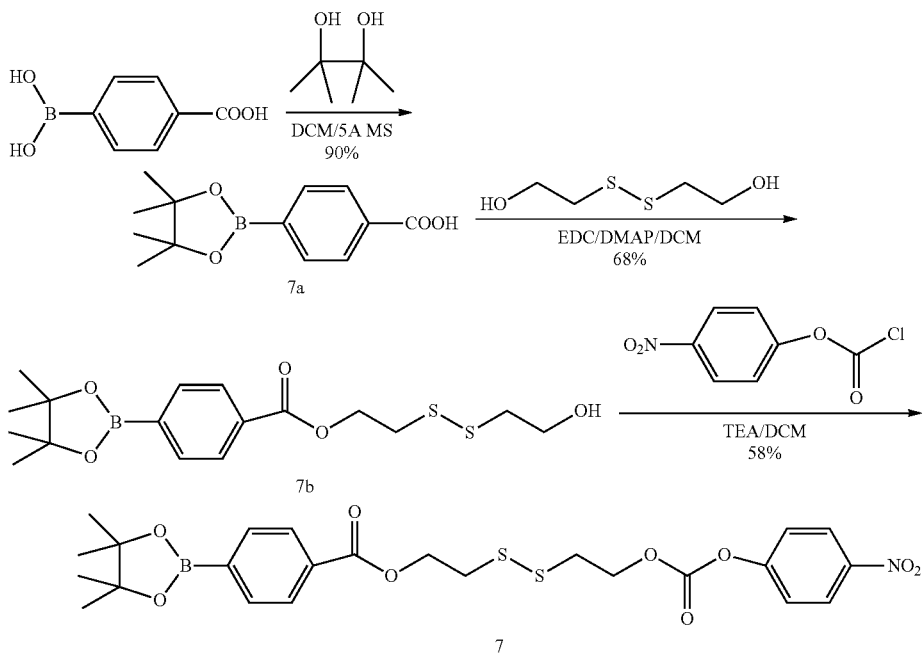

Scheme 9. Synthesis of the redox responsive linker.

Synthesis of Molecule 7a

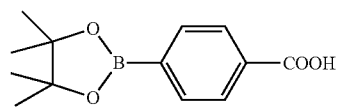

3.32 g 4-boronobenzoic acid (20.1 mmol), 2.37 g pinacol (20.1 mmol) and 10 g 5 Å molecular sieve were dispersed in 40 mL dry DCM. The reaction mixture was stirred at room temperature for overnight. Then, the reaction solution was filtered to remove molecular sieves and all solid impurities. The solid was rinsed by DCM 3 times. The combined solution was concentrated to get the product. (Yield: quantitative)

$^1$H NMR (400 MHz, CDCl$_3$) (δ ppm): 8.09 (d, J=7.7 Hz, 2H), 7.90 (d, J=7.6 Hz, 2H), 1.36 (s, 12H).

$^{13}$C NMR (100 MHz, Acetone-d$_6$) (δ ppm): 167.67, 135.42, 133.77, 129.57, 84.94, 25.18.

Synthesis of Molecule 7b

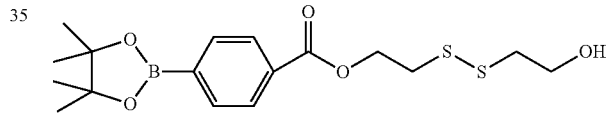

1 g compound 7a (4.0 mmol), 1.244 g 2-Hydroxyethyl disulfide (8.0 mmol) and 0.049 g DMAP (0.4 mmol) were dissolved in 100 mL DCM under ice bath. 1.0 g EDC·HCl 5.2 mmol) was added. The reaction was warmed up to room temperature and stirred for 24 h. Then, the reaction mixture was washed by 1 M HCl, saturated NaHCO$_3$ solution (twice) and brine. The organic layer was collected, dried over anhydrous Na$_2$SO$_4$ and concentrated to get the crude product. It was further purified by combiflash using silica gel as stationary phase and mixture of ethyl acetate/hexane as eluent. (0.99 g, Yield: 64%)

$^1$H NMR (400 MHz, CDCl$_3$) (δ ppm): 8.00 (d, J=8.1 Hz, 2H), 7.85 (d, J=8.0 Hz, 2H), 4.57 (t, J=6.7 Hz, 2H), 3.86 (t, J=5.9 Hz, 2H), 3.04 (t, J=6.7 Hz, 2H), 2.87 (t, J=5.9 Hz, 2H), 1.33 (s, 12H).

$^{13}$C NMR (100 MHz, Acetone-d$_6$) (δ ppm): 166.55, 135.47, 133.28, 129.37, 84.99, 63.70, 60.97, 42.50, 37.79, 25.18.

Synthesis of Molecule 7

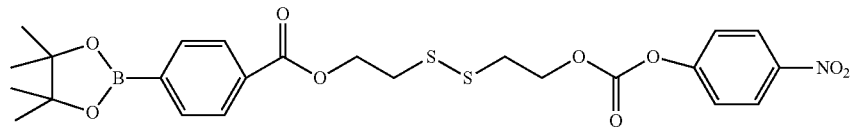

0.5 g compound 7b (1.3 mmol) and 0.263 g TEA (0.363 mL, 2.6 mmol) were dissolved in 5 mL dry DCM under ice bath. 0.278 g 4-nitrochloroformate (1.4 mmol) was added for reaction. The reaction was stirred under room temperature for overnight. Then, the reaction mixture was washed with saturated NaHCO$_3$ solution (twice) and brine. The organic layer was collected, dried over anhydrous Na$_2$SO$_4$ and concentrated to get the crude product. It was further purified by combiflash using silica gel as stationary phase and mixture of ethyl acetate/hexane as eluent. (0.404 g, Yield: 57%)

$^1$H NMR (400 MHz, CDCl$_3$) (δ ppm): 8.28-8.20 (m, 2H), 8.01 (d, J=8.2 Hz, 2H), 7.86 (d, J=8.1 Hz, 2H), 7.39-7.33 (m, 2H), 4.60 (t, J=6.6 Hz, 2H), 4.54 (t, J=6.5 Hz, 2H), 3.10 (t, J=6.6 Hz, 2H), 3.05 (t, J=6.5 Hz, 2H), 1.35 (s, 12H).

$^{13}$C NMR (100 MHz, Acetone-d$_6$) (δ ppm): 166.56, 156.62, 153.17, 146.46, 135.48, 133.21, 129.39, 126.08, 123.14, 85.01, 67.66, 54.96, 37.79, 37.61, 25.18.

Synthesis of P6'

A mixture of 4-cyano-4-(phenylcarbonothioylthio) pentanoic acid (4.18 mg, 0.015 mmol), AIBN (0.99 mg, 0.006 mmol), monomer M1 (polyethylene glycol monomethyl ether methacrylate, average MW: 500, 375 mg, 0.75 mmol), monomer M2 (78.54 mg, 0.15 mmol), Boc-protected guanidium monomer M3 (111.42 mg, 0.3 mmol) and 2,2,2-Trifluoroethyl methacrylate M4 (50.43 mg, 0.3 mmol) were dissolved in 1.5 mL THF and degassed with three freeze-pump-thaw cycles. Then the reaction was transferred to a pre-heated oil bath (65° C.) and stirred for 20 hours under argon. The resultant polymer P6' was precipitated in cold hexanes and washed with hexanes for several times to remove unreacted monomers.

Synthesis of P3'-P9'

The procedures of P3'-P9' were similar to the one used for the synthesis of P6'. The dosage and ratios of monomers were according to Table 2, and other feed reagents and the synthetic routes were same with P6'.

TABLE 2

|     | M1/ mg | M1/ mmol | M2/ mg | M2/ mmol | M3/ mg | M3/ mmol | M4/ mg | M4/ mmol |
|-----|--------|----------|--------|----------|--------|----------|--------|----------|
| P3' | 225    | 0.45     | 78.5   | 0.15     | 334.2  | 0.9      | 0      | 0        |
| P4' | 225    | 0.45     | 78.5   | 0.15     | 0      | 0        | 151.2  | 0.9      |
| P5' | 225    | 0.45     | 78.5   | 0.15     | 111.4  | 0.3      | 100.8  | 0.6      |
| P6' | 375    | 0.75     | 78.5   | 0.15     | 111.4  | 0.3      | 50.4   | 0.3      |
| P7' | 150    | 0.3      | 78.5   | 0.15     | 111.4  | 0.3      | 126    | 0.75     |
| P8' | 150    | 0.3      | 78.5   | 0.15     | 167.1  | 0.45     | 100.8  | 0.6      |
| P9' | 75     | 0.15     | 78.5   | 0.15     | 222.8  | 0.6      | 100.8  | 0.6      |

Scheme 10. Synthesis of P10'-P12'.

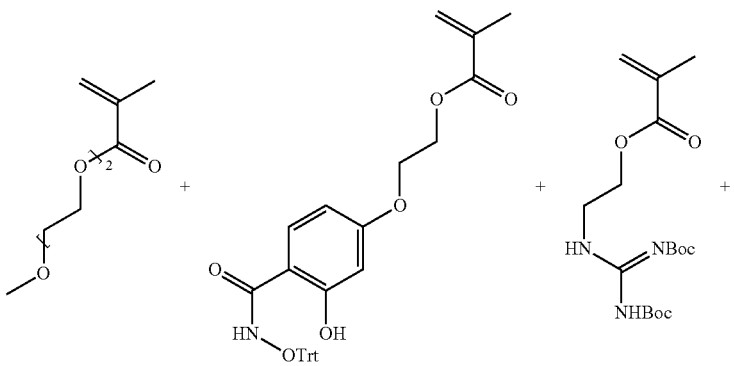

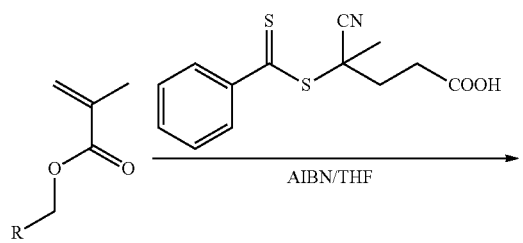

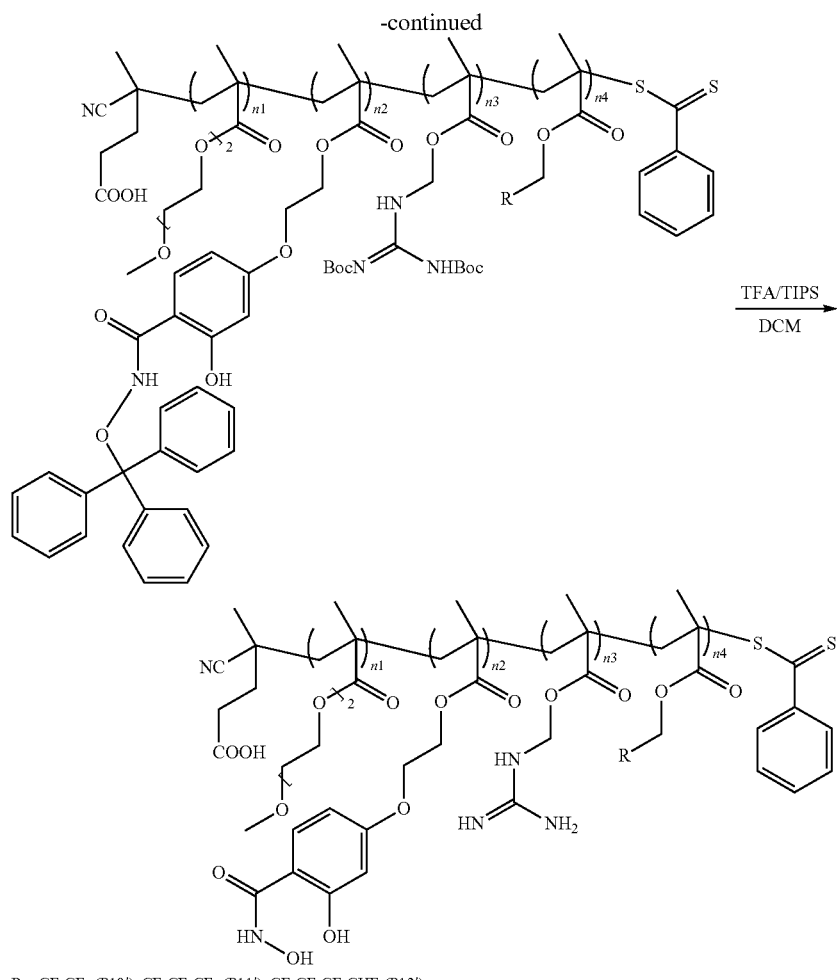

R = CF$_2$CF$_3$ (P10′), CF$_2$CF$_2$CF$_3$ (P11′), CF$_2$CF$_2$CF$_2$CHF$_2$ (P12′)

Synthesis of P10′-P12′

The procedure used for synthesis of P10′, P11′, P12′ was similar to that for P6′. M1 (150 mg, 0.3 mmol), M2 (78.5 mg, 0.15 mmol) and M3 (167.1 mg, 0.45 mmol) were mixed with M5 (2,2,3,3,3-Pentafluoropropyl methacrylate, 130.7 mg, 0.6 mmol), M6 (2,2,3,3,4,4,4-Heptafluorobutyl methacrylate, 168.8 mg, 0.6 mmol) and M7 (2,2,3,3,4,4,5,5-Octafluoropentyl methacrylate, 190.0 mg, 0.6 mmol), for synthesis of P10′, P11′ and P12′ respectively. Other reagents (AIBN and RAFT reagent) and synthetic procedures were the same as P6′ described above.

Deprotection of the Polymers to Make P3-P12

The polymers were further deprotected under TFA to remove the Trt and Boc protection groups. 200 mg of the above synthesized polymer (P3′-P12′) was dissolved in 2 mL DCM. Then, 2 mL TFA and 0.15 mL triisopropylsilane (TIPS) was added under stirring at room temperature. The reaction was stirred for overnight. Then, the deprotected polymer was dried by air flow. The residue was dissolved in THF. The resultant solution was precipitated in hexanes and the product was collected by centrifuge. Further, the obtained polymer was washed with hexanes for several times and dried under vacuum.

Protein Modification by ROS Sensitive Linker 3 mg RNase A was dissolved in 0.5 mL 0.1 M NaHCO$_3$ buffer solution (pH=8.5). To above solution was added 150 μL DMSO solution containing 4.8 mg compound 8. The reaction mixture was then stirred at room temperature for additional 10 h, followed by filtration with a 220 μm filter and ultrafiltration purification using Amicon® Ultra Centrifugal Filters (MWCO=3,000). The final protein was dissolved in 300 μL DI water (10 mg/mL) and stored at 4° C. The modification of the boronic acid linker was quantified by MADLI-MS.

Other proteins such as GFP, BSA, β-gal were prepared using the similar method and also stored at 4° C. with the concentration of 10 mg/mL. The boronic acid modified proteins with ROS responsiveness (RNase A, GFP, BSA, β-gal) are denoted as RNase A-BA, GFP-BA, BSA-BA, β-gal-BA.

Labeling of Proteins with Rhodamine B

To perform the cellular uptake studies, fluorescently-labelled proteins (RNase A, BSA, RNase A-BA and BSA-BA) were prepared by reaction with rhodamine B isothiocyanate (RB). In a typical labelling procedure, proteins (3 mg) were dissolved separately in 2 mL of 0.1 M NaHCO$_3$ buffer (pH 8.5) under stirring. RB (5 eq. of each protein, 10 mg/mL in DMSO) was added dropwise to each protein solution and stirred at room temperature for 2 h under the protection from light. The RB-labelled-proteins were purified by extensive ultrafiltration purification using Amicon® Ultra Centrifugal Filters (MWCO=3,000) to remove excess RB.

Redox and pH Sensitive Linker Modification

The method for modification of protein with redox sensitive and pH sensitive linker is the same as that for ROS sensitive linker by using compound 11 and 12 for reaction. 3 mg RNase A was dissolved in 0.5 mL of 0.1 M NaHCO$_3$ buffer solution (pH=8.5). To above solution was added to a 150 fit DMSO solution containing 6 mg compound 11 or 4 mg compound 12. The reaction mixture was then stirred at room temperature for additional 10 h, followed by filtration on 220 pun filter and ultrafiltration purification using Amicon® Ultra Centrifugal Filters (MWCO=3,000). The final protein was dissolved in 300 µl DI water (10 mg/mL) and stored at 4° C. The modification was quantified by MADLI-MS. The modified RNase A with redox sensitive linker is referred to as RNase A-SS-BA. The pH sensitive linker modified RNase A is referred to as RNase A-BA_pH.

MALDI-MS for Quantification of the Modification

The surface functional boronic acid modification of the proteins was quantified by MALDI-MS. MALDI-MS analyses were performed with Bruker Autoflex III time-of-flight mass spectrometer. All mass spectra were acquired in the reflectron mode with an average of 500 laser shots at ~60% optimized power.

Protein-Polymer Complex

Protein polymer complexes were prepared by mixture of the boronic acid modified protein and polymer with different mass ratios at room temperature for 12 h.

Fluorescence Polarization Measurement

Fluorescence polarization was used to monitor the complexation kinetics of the polymer and boronic acid modified protein. GFP was chosen to study the fluorescent polarization as its intrinsic strong fluorescence. Fluorescence polarization was monitored using a SpectraMax M5 plate reader with a fixed excitation wavelength set to 480 nm and an emission wavelength set to 520 nm. Samples (GFP, GFP-BA, GFP+polymer, and GFP-BA+polymer) were incubated in 96-well plate and the FP was measured immediately after placing all the components together with an interval of 30 s. The process lasted for 2 h at room temperature. The ratio between the protein and polymer was 1:10.

Fluorescence Titration by Alizarin Red S (ARS) Assay:

To further monitor the protein polymer complexation, 0.0025% w/v ARS solution was incubated with 0.25 mg/mL of RNase A-BA for 2 h. This solution was further titrated by different amounts of polymer. In all processes, the concentrations of the RNase A-BA and ARS were kept constant. After the polymer was incubated inside the solution for another 15 min, ARS emission measurement was performed by fluorometer. Emission was monitored at 600 nm with excitation at 490 nm.

ROS-Responsive Study of Modified RNase A:

RNase A-BA and RNase A-BA@polymer (protein and polymer ratio is 1:10) were incubated with 10 mM H$_2$O$_2$ at room temperature for 12 h, followed by ultrafiltration purification using Amicon® Ultra Centrifugal Filters (MWCO=3,000). The proteins were then subjected to ESI-MS characterization or enzyme activity assay and compared to modified proteins without H$_2$O$_2$ treatment or native RNase A.

SDS-PAGE for Protein-Polymer Complexation and Release Studies:

20 µL of different samples were mixed with 5 µL of loading buffer and 20 µL of each sample was loaded on acrylamide gel. The protein-polymer mixture was prepared by incubation of the polymer and boronic acid modified protein for 12 h.

For complexation kinetics, the polymer and the protein were mixed in a centrifuge tube for different times. At the desired time, the complex was mixed with loading buffer and run the gel immediately.

For ROS responsive release experiment, identical protein-polymer conjugate samples (after incubation for 12 h) were treated with different amounts of H$_2$O$_2$ (1 mM or 10 mM) and incubated at room temperature for different time intervals before subjecting to acrylamide gel electrophoresis. To calculate the amount of released protein from each sample, standard curves were generated from the known concentrations of pure protein samples loaded into the gel lanes. The gel image analysis and quantification were performed with Bio-Rad Image Lab™ software.

For redox and pH responsive release experiment, the protein-polymer complexes were treated with DTT (or GSH, 10 mM) and pH=5.0 for 12 h before subjecting to acrylamide gel electrophoresis.

Activity Assay:

For RNase A

RNaseAlert® activity kit (Thermo-Fisher Scientific) was used to check the activity of RNase A based samples. RNase A cleaves the oligonucleotide substrate of the assay consisting a fluorophore and a quencher present at two extreme ends, thus releasing the fluorophore which can be detected and quantified with a fluorometer. For a typical kinetics experiment, 5 µL RNaseAlert®Substrate and 10 µL assay buffer (10×, provided by the assay kit) were placed in a black 96-well plate. To the above assay substrate, 85 µL of RNase A containing samples (2 ng/mL of final proteins) were added. The fluorescence intensity at 520 nm (Excitation 490 nm) was monitored with SpectraMax® M5 spectrophotometer over 30 min time.

For β-gal

Beta galactosidase (β-Gal) activity assay kit (BioVision) was used to measure the activity of β-Gal based samples. Measure fluorescence (Ex/Em=480/520 nm) immediately in kinetic mode for 30 min. For a typical kinetics experiment, 2 µL RNaseAlert®Substrate and 97 µL assay buffer (provided by the assay kit) were placed in a black 96-well plate. To the above assay substrate, 1 µL of β-Gal containing samples (0.5 nM of final proteins for β-Gal, β-Gal-BA, β-Gal-BA@polymer) were added.

Circular Dichroism (CD) Spectra:

CD spectra of the protein complex, released protein and native protein samples were recorded on JASCO J-1500 spectrophotometer. The protein complex was prepared through the typical complexation method by mixture of the boronic acid modified protein and polymer with the ratio of 1:10 for 12 h. The released protein sample was prepared by incubation of the protein-polymer sample with 10 mM 11202 for 24 h. It was further purified by ultracentrifuge with Amicon Ultra Centrifugal Filters MWCO 3K for 5 times. For recording the spectra, 200 µL protein solution was injected into a quartz cuvette of 1-mm path length, equilibrated at 25° C. for 10 min and scanned from 190 to 250 nm (scan rate: 20 nm/min, interval: 0.2 nm, average of three spectra).

Cell Culture:

Different cell lines (including Human cervical carcinoma (HeLa) cells, MDA-MB-231 cells and MCF-7 cells) were cultured in T75 cell culture flask containing Dulbecco's Modified Eagle Medium/Nutrient Mixture F-12 (DMEM/F12) in a humidified S26 incubator with 5% CO$_2$ at 37° C. Culture media was supplemented with 10% fetal bovine serum (FBS), 1% L-glutamine and 1% antibiotic-antimycotic (100 units/mL of penicillin, 100 μg/mL of streptomycin, and 0.25 μg/mL of amphotericin B).

Cellular Uptake Studies for Protein Delivery and Endosomal Escape:

Cell internalization studies were performed with HeLa cells seeded at 150,000 cells/mL in glass-bottomed petri-dishes and cultured for 24 h at 37° C. in a 5% $CO_2$ incubator. Prior to delivery, cells were washed three times with PBS buffer and incubated with 1 mL media containing polymer-rhodamine B-protein conjugate or rhodamine B-protein conjugate (protein concentration 30 μg/mL) at 37° C. for 6 h. After that, cell nucleus was stained with Hoechst 33342 (8 μM) and finally the media was replaced with fresh stock and incubated for another 1 h before subjecting to CLSM analysis. In addition, to study the endosomal escape of the labelled proteins, HeLa cells were incubated with labelled nanoassemblies for 4 and 24 h. After that it was stained with LysoTracker® Green to label endosomes/lysosomes and studied the co-localization of red and green fluorescence channels. Live cell imaging was performed using Nikon Spectral AI confocal microscope.

Cell Viability with MTT Assay:

Different cells (including HeLa cells, MDA-MB-231, MCF-7) were seeded into 96-well tissue culture plates at a density of 10, 000 cells/well/100 μL sample and incubated at 37° C. After 24 h, culture media was replaced and cells were treated with different concentrations of protein-polymer complex and control protein samples (0.1 mg/mL to 2 mg/mL protein-polymer complex; for naked protein and modified protein concentration were matched with the protein-polymer complex) in 100 μL media (10 μL protein containing solution with different concentrations+90 μL medium). At the desired time interval, medium was removed and the cells were cultured by 100 μL 10% MTT (5 mg/mL) in medium solution for another 4 h. Then, the solution was discarded and the remaining crystal was dissolved by 100 μL DMSO. The solution was subjected to absorbance measurement with SpectraMax® M5 at 590 nm. Cell death was measured by the MTT assay in triplicate.

For ROS Sensitive PMA Treatment Enhanced Cytotoxicity

HeLa cells were seeded in a 96-well plate 24 h before the delivery experiment at a density of 10,000 cells per well (100 μL). On the day of the experiment, cells were pre-treated with RNase A-BA@polymer nanoparticles with varied concentrations for 24 h. After nanoparticle removal, cells were then treated with 200 nM PMA in DMEM or DMEM only as a control for 1 h. After removing PMA and washing the cells with DMEM, cells were maintained for another 24 h with fresh culture medium before viability measurement using the MTT assay. The toxicity of PMA was excluded by treating cells with 200 nM PMA only in the absence of RNase A complex.

Materials, compositions, and components disclosed herein can be used for, can be used in conjunction with, can be used in preparation for, or are products of the disclosed methods and compositions. It is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compounds or compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Unless defined otherwise, all technical and scientific terms used herein have the same meaning as commonly understood by one of ordinary skill in the art to which this invention belongs. General principles of organic chemistry, as well as specific functional moieties and reactivity, are described in "Organic Chemistry", Thomas Sorrell, University Science Books, Sausalito: 2006.

Definitions of specific functional groups and chemical terms are described in more detail below. When a range of values is listed, it is intended to encompass each value and sub-range within the range. For example, "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

Where substituent groups are specified by their conventional chemical formulae, written from left to right, they equally encompass the chemically identical substituents that would result from writing the structure from right to left, e.g., —C(=O)—O— is equivalent to —O—C(=O)—.

Structures of compounds of the invention are limited by principles of chemical bonding known to those skilled in the art. Accordingly, where a group may be substituted by one or more of a number of substituents, such substitutions are selected so as to comply with principles of chemical bonding and to give compounds that are not inherently unstable and/or would be known to one of ordinary skill in the art as likely to be unstable under ambient conditions (e.g., aqueous, neutral, and several known physiological conditions).

Applicant's disclosure is described herein in preferred embodiments with reference to the figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

The invention claimed is:

1. A functionalized copolymer, comprising:
a first monomer of PEG-methacrylate (PEG-MA); and
a second monomer of methacrylate having a side chain modified with a salicylhydroxamate moiety.

2. The functionalized copolymer of claim 1, wherein the first monomer is the majority monomer and the second monomer is the minority monomer.

3. The functionalized copolymer of claim 1, wherein the first monomer comprises a side chain comprising from about 1 to about 20 ethylene-oxide units.

4. The functionalized copolymer of claim 1, wherein the first monomer has the structure of:

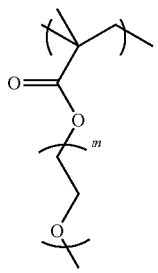

where m is an integer in the range of 1 to 20.

5. The functionalized copolymer of claim 1, wherein the second monomer comprises:

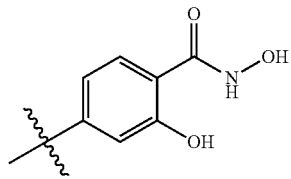

or a protected form thereof.

6. The functionalized copolymer of claim 1, wherein the second monomer has the structure of:

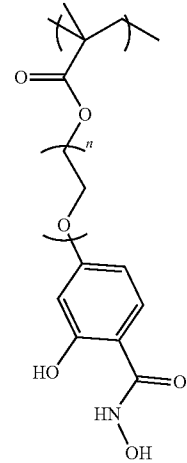

or a protected form thereof, where n is an integer in the range of 1 to 20.

7. The functionalized copolymer of claim 1, having the structural formula:

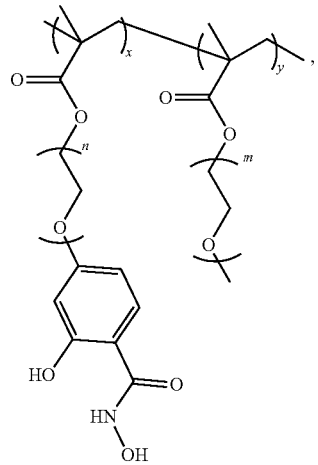

wherein
each of m and n is independently an integer in the range of 1 to 20, and
x:y is in the range from about 5:95 to about 70:30.

8. The functionalized copolymer of claim 1, having a molecular weight (MW) in the range of about 1 k to about 200 k.

9. The functionalized copolymer of claim 1, consisting of a first monomer of PEG-methacrylate (PEG-MA) and a second monomer of methacrylate having a side chain modified with a salicylhydroxamate moiety.

10. A method for delivering a protein, comprising:
surface functionalizing the protein with arylboronic acid modifications of one or more lysine residues on the protein;
forming a polymer-protein conjugate by reacting the surface functionalized protein with a copolymer comprising a first monomer of PEG-methacrylate (PEG-MA) and a second monomer of methacrylate having a side chain modified by a salicylhydroxamate moiety thereby forming a molecular assembly comprising the polymer-protein conjugate, wherein the polymer-protein conjugate comprises a degradable linker;
transporting the molecular assembly to a target site to degrade the linker thereby releasing the protein at the target site.

* * * * *